(12) United States Patent
Chao-Shern

(10) Patent No.: US 9,856,516 B2
(45) Date of Patent: Jan. 2, 2018

(54) METHODS FOR IMPROVED ISOLATION OF GENOMIC DNA TEMPLATES FOR ALLELE DETECTION

(71) Applicant: AVELLINO LAB USA, INC., Menlo Park, CA (US)

(72) Inventor: Connie Chao-Shern, Menlo Park, CA (US)

(73) Assignee: AVELLINO LABS USA, INC., Menlo Park, CA (US)

(*) Notice: Subject to any disclaimer, the term of this patent is extended or adjusted under 35 U.S.C. 154(b) by 0 days.

(21) Appl. No.: 14/788,572

(22) Filed: Jun. 30, 2015

(65) Prior Publication Data

US 2015/0299773 A1 Oct. 22, 2015

Related U.S. Application Data

(63) Continuation of application No. PCT/US2014/029466, filed on Mar. 14, 2014.

(60) Provisional application No. 61/852,357, filed on Mar. 15, 2013, provisional application No. 61/852,358, filed on Mar. 15, 2013.

(51) Int. Cl.
  *C12Q 1/68* (2006.01)
  *C12N 15/10* (2006.01)

(52) U.S. Cl.
  CPC ....... *C12Q 1/6806* (2013.01); *C12N 15/1003* (2013.01)

(58) Field of Classification Search
  CPC ....... C12Q 1/686; C12Q 1/6844; C12P 19/34; C12N 15/1003; C07H 21/00
  See application file for complete search history.

(56) References Cited

U.S. PATENT DOCUMENTS

| | | | |
|---|---|---|---|
| 6,018,713 A | 1/2000 | Coli et al. | |
| 6,171,112 B1 | 1/2001 | Clark et al. | |
| 6,331,276 B1 | 12/2001 | Takei et al. | |
| 2003/0176650 A1 | 9/2003 | Grosse et al. | |
| 2003/0204418 A1 | 10/2003 | Ledley | |
| 2003/0211500 A1* | 11/2003 | Woosley | C12Q 1/6883 435/6.17 |
| 2004/0217345 A1 | 11/2004 | Boland et al. | |
| 2004/0263853 A1 | 12/2004 | Hill et al. | |
| 2005/0019757 A1* | 1/2005 | Stolarchuk | B01L 3/502 435/5 |
| 2006/0038990 A1 | 2/2006 | Habib et al. | |
| 2006/0057604 A1 | 3/2006 | Chen et al. | |
| 2006/0066249 A1 | 3/2006 | Wark et al. | |
| 2007/0254296 A1 | 11/2007 | Jiang et al. | |
| 2007/0274895 A1 | 11/2007 | Jesih et al. | |
| 2008/0113344 A1 | 5/2008 | Wirtz et al. | |
| 2008/0174775 A1 | 7/2008 | Moskovits et al. | |
| 2008/0267946 A1 | 10/2008 | Kim et al. | |
| 2009/0073447 A1 | 3/2009 | Dahint et al. | |
| 2009/0305394 A1 | 12/2009 | Lee et al. | |
| 2010/0190158 A1* | 7/2010 | Peitz | C12Q 1/6841 435/5 |
| 2011/0053794 A1 | 3/2011 | Zhang | |
| 2012/0231537 A1 | 9/2012 | Templeton et al. | |
| 2013/0302811 A1* | 11/2013 | Lee | C12Q 1/6883 435/6.12 |

FOREIGN PATENT DOCUMENTS

| | | |
|---|---|---|
| CN | 101144812 A | 3/2008 |
| CN | 101374850 A | 2/2009 |
| EP | 1715326 A1 | 10/2006 |
| EP | 1964606 A1 | 9/2008 |
| EP | 2019309 A2 | 1/2009 |
| JP | 2006-250668 A | 9/2006 |
| JP | 2009-045057 A | 3/2009 |
| JP | 2009-523442 A | 6/2009 |
| KR | 1020070076532 A | 7/2007 |
| WO | WO 00/58509 A2 | 10/2000 |
| WO | WO 2005/015198 A | 2/2005 |
| WO | WO 2005/040756 A2 | 5/2005 |
| WO | WO 2005/114298 A2 | 12/2005 |
| WO | WO 2007/002567 A2 | 1/2007 |
| WO | WO 2007/083928 A1 | 7/2007 |
| WO | WO 2008/089280 A2 | 7/2008 |
| WO | WO 2012/044121 A2 | 4/2012 |
| WO | WO 2015/073978 A2 | 5/2015 |

OTHER PUBLICATIONS

Beer et al., On-Chip, Real-Time, Single-Copy Polymerase Chain Reaction in Picoliter Droplets. Analytical Chemistry 79 (22) : 8471 (2007).*
Richards et al.Multiplex PCR amplification from the CFTR gene using DNA prepared from buccal brushes/swabs. Human Molecular Genetics 2 (2) : 159-163 (1993).*
Walker et al., Collection of genomic DNA by buccal swabs for polymerase chain reaction-based biomarker assays. Enviromental Health Perspectives 107 (7) :517 (1999).*
Avellino Co. Ltd., Certificate of Patent, JP 2014-000571, dated Apr. 1, 2016, 5 pgs.

(Continued)

*Primary Examiner* — Ethan Whisenant

(74) *Attorney, Agent, or Firm* — Morgan, Lewis & Bockius LLP

(57) ABSTRACT

The present disclosure relates to improved methods for the isolation of genomic material and detection of disease related single nucleotide polymorphisms. In some aspects, these methods increase the total recovery of genomic DNA from buccal cell samples by improving cell lysis conditions. In other aspects, these methods allow for the reuse of patient buccal swab samples, reducing the likelihood of having to collect additional patient samples for re-testing. Finally, in some aspects, these methods increase the sensitivity of SNP detection using an improved real-time PCR assay protocol.

21 Claims, 8 Drawing Sheets

(56) References Cited

OTHER PUBLICATIONS

Avellino Co. Ltd., Patent Examination Report No. 1, AU2009344501, dated Sep. 24, 2012, 3 pgs.
Avellino Co. Ltd., Patent Examination Rpt—No. 3—AU2009344501, dated Nov. 25, 2013, 4 pgs.
Avellino Co. Ltd., Decision to Grant, EP09843403.8, dated Feb. 10, 2014, 1 pg.
Avellino Co. Ltd., Patent Certificate, EP09843403-8, dated Oct. 29, 2014, 1 pg.
Avellino Co. Ltd., Invitation to Respond to Written Opinion, SG201107572.8, dated Jan. 29, 2014, 12 pgs.
Avellino Co. Ltd., Certificate of Patent, ZA2011/07967, dated Aug. 28, 2013, 1 pg.
Avellino Co. Ltd., Decision of Grant, RU2011146553, dated Jul. 23, 2014, 2 pgs.
Avellino Co. Ltd., Letters Patent, RU2011146553, dated Dec. 17, 2014, 1 pg.
Avellino Co. Ltd., The First Office Action, CN201080047181.3, dated Jul. 15, 2013, 1 pg.
Avellino Co. Ltd., Certificate of Patent, JP2012525483, dated Jan. 10, 2014, 5 pgs.
Avellino Co. Ltd., First office Action, IL215845, dated Jul. 10, 2013, 4 pgs.
Avellino Co. Ltd., Further Office Action, IL215845, dated Mar. 25, 2014, 4 pgs.
Avellino Lab, Extended European Search Report, EP14762603.0, dated Jul. 14, 2016, 11 pgs.
Avellino Lab USA Inc., International Preliminary Report on Patentability, PCT/US2014/065975, dated May 17, 2016, 12 pgs.
Korea Advanced Institute of Science and Technology et al., Extended European Search Report, EP10810154.4, dated Jan. 18, 2016, 9 pgs.
Cao W. et al., "Comparison of Methods for DNA Extraction from Paraffin-Embedded Tissues and Buccal Cells," Cancer Detection and Prevention, Elsevier Science, NL, vol. 27, No. 5, Jan. 1, 2003, 8 pgs.
Endo T et al., "Label-Free Detectionof Peptide Nucleic Acid-DNA Hybridization Using Localized Surface Plasmon Resonance Based Optical Biosensor," Analytical Chemisty, American Chemical Society, US, vol. 77, No. 21, 8 pgs.
Lounsbury Jenny et al., "Enhanced Recovery of Spermatozoa and Comprehensive Lysis of Epithelial Cells from Sexual Assault Samples Having a Low Cell Counts for Aged Up to One Year," Forensic Science International: Genetics, vol. 8, No. 1, Jan. 2014, 6 pgs.
Morbini Patrizia et al., "Oral HPV Infection and Persistence in Patients with Head and Neck Cancer," Oral Surgery, Oral Medicine, Oral Pathology and Oral Radiology, vol. 116, No. 4, Oct. 2013, 11 pgs.
Neuhaus, T., et al., "Reliability of Non-Invasively Acquired Human Genomic DNA as a Substrate for Real-Time PCR-Assisted Analysis of Genetic Polymorphisms," Archives of Toxicology, vol. 78, No. 7, Jul. 1, 2004, 7 pgs.
Avellino Co. Ltd., Notification of Grant, CN201180056997.7, dated Jul. 16, 2015, 5 pgs.
Korea Advanced Institute of Science and Technology et al., Invitation Pursuant to Rule 62a(1) EPC, EP10810154.4, dated Sep. 1, 2015, 2 pgs.
Afshari, N., Survey of Patients With Granular, Lattice, Avellino, and Reis-Bücklers Corneal Dystrophies for Mutations in the BIGH3 and Gelsolin Genes, Arch Ophthalmol, Jan. 2001, vol. 119, pp. 16-22.
Armelao, L, Innovative metal oxide-based substrates for DNA Microarrays, Inorganica Chimica Acta, vol. 361, Apr. 10, 2010, pp. 3603-3608.
Avellino Co., Ltd., Certificate of Patent, JP 2012-505796, dated May 1, 2015, 2 pgs.
Avellino Co., Ltd., European Search Report, EP 14186678.0, dated Feb. 18, 2015, 5 pgs.
Avellino Co., Ltd., Examination Report, IN 7514/CHENP/2011, dated Oct. 15, 2014, 2 pgs.
Avellino Co., Ltd., First Examination Report, IN 7514/CHENP/2011, dated Aug. 7, 2014, 1 pg.
Avellino Co., Ltd., Letters Patent, ZL 200980159748.3, dated Apr. 8, 2015, 2 pgs.
Avellino Co., Ltd., Notice of Reasons for Rejection, JP 2012-505796, dated Nov. 11, 2014, 3 pgs.
Avellino Co., Ltd., Notice of Reasons for Rejection, JP 2012-505796, dated Oct. 29, 2013, 3 pgs.
Avellino Co., Ltd., Notice of Reasons for Rejection, JP 2013-531500, dated Oct. 21, 2014, 5 pgs.
Avellino Co., Ltd., Notice of Reasons for Rejection, JP 2014-000571, dated Mar. 10, 2015, 4 pgs.
Avellino Co., Ltd., Notification of the Office Rejection, CN 200980159748.3, dated Aug. 6, 2014, 4 pgs.
Avellino Co., Ltd., The First Office Action, CN 200980159748.3, dated Aug. 31, 2012, 4 pgs.
Avellino Co., Ltd., The First Office Action, CN 201180056997.7, dated Dec. 22, 2014, 4 pgs.
Avellino Co., Ltd., The Second Office Action, CN 200980159748.3, dated Jul. 11, 2013, 5 pgs.
Avellino Co., Ltd., The Third Office Action, CN 200980159748.3, dated Mar. 24, 2014, 5 pgs.
Avellino Lab USA, Inc., International Search Report and Written Opinion, PCT/US2014/029466, dated Jul. 14, 2014, 11 pgs.
Avellino Lab USA, Inc., International Search Report and Written-Opinion, PCT/US2014/065975, dated May 18, 2015, 19 pgs.
Biotechnology Journal, 2006, vol. 6, No. 5, pp. 621-624.
Chakravarthi, K., TGFBI Gene Mutations Causing Lattice and Granular Corneal Dystrophies in Indian Patients, Investigative Ophthalmology & Visual Science, Jan. 2005, vol. 46, No. 1, pp. 121-125.
Database Genbank, Dec. 10, 1997, Database accession No. AF035627, 2 pgs.
Dolmetsch, A., Combined granular-lattice corneal dystrophy (Avellino) in a patient with no known Italian ancestry, Can. J. Ophthalmol, Accepted for publication Sep. 15, 1995, vol. 31, No. 1, pp. 29-31.
GenBank Accession No. AF035627, *Homo sapiens* mutant kerato epithelin (BIGH3) Gene, exon 4, partial cds, [retrieved on-line: http://www.ncbi.nlm.nih.gov/nuccore/AF035627.1, retrieval date, Sep. 7, 2013], published date Dec. 10, 1997, 1 pg.
Grove, D.S., Quantitative Real-Time Polymerase Chain Reaction for the Core Facility Using TaqMan and the Perkin-Elmer/Applied Biosystems Division 7700 Sequence Detector, Journal of Biomolecular Techniques, Mar. 1999, vol. 10, pp. 11-16.
Halfon, P., Detection of IL28B SNP DNA from Buccal Epithelial Cells, Small Amounts of Serum and Dried Blood Spots, Mar. 2012, Plos One, vol. 7, Issue 3, Article No. e33000, pp. 1-6.
Han, K.E., Clinical Findings and Treatments of Granular Corneal Dystrophy Type 2 (Avellino Corneal Dystrophy): A Review of the Literature, Eye & Contact Lens, vol. 36, No. 5, Sep. 2010, 4 pgs.
Holland, E., Avellino Corneal Dystrophy. Clinical Manifestations and Natural History, Ophthalmology, originally received Jan. 2, 1992, vol. 99, No. 10, pp. 1564-1568.
Huerva V., Role of BIGH3 R124H mutation in the diagnosis of Avellino corneal dystrophy, European Journal of Ophthalmology, May 2008, vol. 18, No. 3, pp. 345-350.
Jun, R., Avellino Corneal Dystrophy after LASIK, Ophthalmology, © 2004 (originally received Mar. 21, 2003), vol. 111, pp. 463-468.
Kennedy, S., Combined granular lattice dystrophy (Avellino corneal dystrophy), Br. J. Ophthalmol, Accepted for publication Jan. 19, 1996, vol. 80, pp. 489-490.
Kephart, D., Rapid Isolation of Genomic DNA from Small Quantities of Human Tissue, 1999, Profiles in DNA, vol. 2, No. 3, pp. 7-9.
Kim, J. W., Clinical Manifestations of Avellino Corneal Dystrophy Diagnosed by Non-invasive Genetic Test, J Korean Ophthalmol Soc vol. 49, No. 9, 2008, pp. 1431-1436.
Lee, Final Office Action, U.S. Appl. No. 13/264,784, dated May 7, 2014, 26 pgs.
Lee, Final Office Action, U.S. Appl. No. 13/391,167, dated May 18, 2015, 16 pgs.
Lee, Notice of Allowance, U.S. Appl. No. 13/391,167, dated Jul. 27, 2015, 9 pgs.

(56) References Cited

OTHER PUBLICATIONS

Lee, Office Action, U.S. Appl. No. 13/264,784, dated Sep. 12, 2013, 14 pgs.
Lee, Office Action, U.S. Appl. No. 13/391,167, dated Dec. 29, 2014, 9 pgs.
Lee, Office Action, U.S. Appl. No. 13/876,603, dated Apr. 13, 2015, 11 pgs.
Miller, S., A Simple Salting Out Procedure for Extracting DNA from Human Nucleated Cells, Nucleic Acids Research, 1998, vol. 16, No. 3, ,Accepted for publication Jan. 19, 1996, p. 1215.
NCBI, *Homo Sapiens* Transforming Growth Factor, Beta-Induced, 68kDa (TGFBI), mRNA, NCBI Reference Sequence NM_000358.2, release 107, Mar. 13, 2015, 6 pgs.
Paliwal, P., Heterozygous Change T>G in the Sequence of Exon 12 of TGFBI Gene Seen in a Patient with Corneal Dystrophy, Genbank: GQ368823.1, National Center for Biotechnology Information, GenBank, Jul. 28, 2009, 6 pgs.
Romero, P., Anticipation in familial lattice corneal dystrophy type I with R124C mutation in the TGFBI (BIGH3) gene, Molecular Vision, vol. 14, May 7, 2008, pp. 829-835.
Stewart, H., Heterogeneity in Granular Corneal Dystrophy: Identification of Three Causative Mutations in the TGFBI (BIGH3) Gene-Lessons for Corneal Amyloidogenesis, Human Mutation, Accepted revised manuscript Apr. 23, 1999, vol. 14, pp. 126-132.
Strum, J.C. Tissue Expression Profiling Using Real-Time PCR, Current Protocols in Pharmacology, Nov. 2002, Chapter 6: Unit 6.9. DO 1: 10.1002/0471141755.PH0609S18, 9 pgs.
Wittwer, C.T. Real-Time Multiplex PCR Assays, 2001, Department of Pathology, University of Utah, School of Medicine, Salt Lake City, Utah 84132, 13 pgs.
Yoo, S. Y., Development of a DNA chip for the diagnosis of the most common corneal dystrophies caused by mutations in the βigh3 gene, Br J Opthalmol vol. 91, Jan. 10, 2007, pp. 722-727.
Yoshida, S., An Analysis of BIGH3 Mutations in Patients with Corneal Dystrophies in the Kyushu District of Japan, Jpn J Opthalmol, vol. 46, Jul.-Aug. 2002, pp. 469-471.
Zheng, Y. B., Surface Plasmons of Metal Nanostructure Arrays: From Nanoengineering to Active Plasmonics, Journal of the Association for Laboratory Automation, Aug. 2008, vol. 13, No. 4, pp. 215-226.
Avellino Co. Ltd., Notice of Reasons for Rejection, JP 2014-000571, dated Oct. 6, 2015, 7 pgs.
Avellino Co., Ltd. Decision of Rejection, JP2013-531500, dated Aug. 21, 2015, 11 pgs.
Avellino Lab USA Inc., International Preliminary Report on Patentability, PCT/US2014/029466, dated Jul. 14, 2014, 11 pgs.
Lee, Final Office Action, U.S. Appl. No. 13/876,603, dated Nov. 6, 2015, 14 pgs.
Avellino Co. Ltd., Office Action, CN201510121642.1, dated Aug. 12, 2016, 8 pgs.
Avellino Lab, Communication Pursuant to Rules 161(2) and 162, EP14862501, EP14762603.0, dated Jul. 21, 2016, 2 pgs.
Lee, Office Action, U.S. Appl. No. 13/876,603, dated Nov. 3, 2016, 12 pgs.
Avellino Co., Certificate of Patent, JP2013-531500, Jan. 13, 2017, 3 pgs.
Avellino Lab, Communication Pursuant to Rules 70(2) and 70a(2), EP14762603.0, dated Aug. 2, 2016, 12 pgs.
Avellino Lab, Formality Office Action JP2016531678, dated Mar. 29, 2017, 3 pgs.
Lee, Final Office Action, U.S. Appl. No. 14/454,669, dated Feb. 22, 2017, 14 pgs.
Lee, Office Action, U.S. Appl. No. 14/472,325, dated Dec. 19, 2016, 18 pgs.

\* cited by examiner

ACD Fw primer:
(SEQ ID NO: 1)
5'-TCC ACC ACC ACT CAG CTG TA

ACD Re primer:
(SEQ ID NO: 2)
5'-CCA TCT CAG GCC TCA GCT T
(60 bp)

AV Fw primer:
(SEQ ID NO: 3)
5'-TGC AGC CCT ACC ACT CTC AA

AV Re primer:
(SEQ ID NO: 4)
5'-AGG CCT CGT TGC TAG G
(150 bp)

Real Fw primer:
(SEQ ID NO: 5)
5'-TAG TCT CTT ATT CTA ATA GA

Real Re primer:
(SEQ ID NO: 6)
5'-GCT GCA GAC TCT GTG TTT AA
(860 bp)

ACD Fw2 primer:
(SEQ ID NO: 7)
5'-CCA TCC CTC CTT CTG TCT TCT G

ACD Re2 primer:
(SEQ ID NO: 8)
5'-CGG GCC CCT CCA TCT C
(140 bp)

ACD Fw3 primer:
(SEQ ID NO: 9)
5'-CAG AGA AGG GAG GGT GTG GTT

ACD Re3 primer:
(SEQ ID NO: 10)
5'-GGG CGA AGA TGG TGA AGC T
(190 bp)

ACD Fw4 primer:
(SEQ ID NO: 11)
5'-TCC TCG TCC TCT CCA CCT GTA

ACD Re4 primer:
(SEQ ID NO: 12)
5'-AGC TGG CAA GGA GGC CC

ACD Fw5 primer:
(SEQ ID NO: 13)
5'-TTT GGG CTT TCC CAC ATG C

ACD Re5 primer:
(SEQ ID NO: 14)
5'-GGC AGA CGG AGG TCA TCT CA

ACD Fw6 primer:
(SEQ ID NO: 15)
5'-GTA GTA CCG TGC TCT CTG

ACD Re6 primer:
SEQ ID NO: 16)
5'-AGT TCC CCA TAA GAA TCC CCC

ACD Fw7 primer:
(SEQ ID NO: 17)
5'-GGC TGG ACC CCC AGA GG

ACD Re7 primer:
(SEQ ID NO: 18)
5'-ACC CCT CGG GGA AGT AAG G

ACD Fw8 primer:
(SEQ ID NO: 19)
5'-AAC CTT TAC GAG ACC CTG GGA

ACD Re8 primer:
(SEQ ID NO: 20)
5'-GAC TCC CAT CCA TCA TGC CC

ACD Fw9 primer:
(SEQ ID NO: 21)
5'-AGT CGT TGG ATC CAC CAC CA

ACD Re9 primer:
(SEQ ID NO: 22)
5'-GAC GTC ATT TCC TAC TGT TTC AGG

ACD Fw10 primer:
(SEQ ID NO: 23)
5'-CCC CCC AGA AAC AGC CTG

ACD Re10 primer:
(SEQ ID NO: 24)
5'-TTC TAA GGG GTT AAG GAG AAA GCT T

Figure 2

Normal probe 1:
(SEQ ID NO: 25)
VIC-CAC GGA CCG CAC GGA-NFQ
(15 bp)

Mutant probe 1:
(SEQ ID NO: 26)
FAM-CAC GGA CCA CAC GGA-NFQ

Normal probe 2:
(SEQ ID NO: 27)
VIC-ACA CGG ACC GCA CG-NFQ

Mutant probe 2:
(SEQ ID NO: 28)
FAM-ACA CGG ACC ACA CG-NFQ
(14 bp)

Normal probe 3:
(SEQ ID NO: 29)
VIC-TAC ACG GAC CGC A-NFQ

Mutant probe 3:
(SEQ ID NO: 30)
FAM-TAC ACG GAC CAC A-NFQ
(13 bp)

Normal probe 4:
(SEQ ID NO: 31)
VIC-CTG TAC ACG GAC CGC ACG-NFQ

Mutant probe 4:
(SEQ ID NO: 32)
FAM-CTG TAC ACG GAC CAC ACG-NFQ
(18 bp)

Normal probe 5:
(SEQ ID NO: 33)
VIC-CTG TAC ACG GAC CGC ACG GAG-NFQ

Mutant probe 5:
(SEQ ID NO: 34)
FAM-CTG TAC ACG GAC CAC ACG GAG-NFQ
(21 bp)

Normal probe 6:
(SEQ ID NO: 35)
VIC-GCT GTA CAC GGA CCG CAC GGA GAA-NFQ

Mutant probe 6:
(SEQ ID NO: 36)
FAM-GCT GTA CAC GGA CCA CAC GGA GAA-NFQ

Normal probe 7:
(SEQ ID NO: 37)
VIC-ACC GCA CGG AGA AGC-NFQ

Mutant probe 7:
(SEQ ID NO: 38)
FAM-ACC ACA CGG AGA AGC-NFQ

Normal probe 8:
(SEQ ID NO: 39)
VIC-ACC GCA CGG AGA AGC TGA GGC-NFQ

Mutant probe 8:
(SEQ ID NO: 40)
FAM-ACC ACA CGG AGA AGC TGA GGC-NFQ

Normal probe 8:
(SEQ ID NO: 41)
VIC-ACC GCA CGG AGA AGC TGA GGC CTG-NFQ

Mutant probe 8:
(SEQ ID NO: 42)
FAM-ACC ACA CGG AGA AGC TGA GGC CTG-NFQ

Figure 3

|  | Time | 40X volume | 7500 Results | | StepOnePlus Results | | Result Quality / Reliability | |
|---|---|---|---|---|---|---|---|---|
|  |  |  | Allele 1 | Allele 2 | Allele 1 | Allele 2 | Allele 1 | Allele 2 |
| 36 cycles 3 second @ 95°C | 60 min | 0.2 μL | R1: 0.582 R2: 0.347 R3: 0.326 | R1: 0.123 R2: 0.099 R3: 0.099 | R1: 0.260 R2: 0.150 R3: 0.161 | R1: 0.006 R2: 0.000 R3: 0.000 | Acceptable | Failed |
| 40 cycles 3 second @ 95°C | 83 min | 0.15 μL | R1: 1.293 R2: 1.065 R3: 1.070 | R1: 0.223 R2: 0.260 R3: 0.176 | R1: 0.786 R2: 0.719 R3: 0.617 | R1: 0.091 R2: 0.085 R3: 0.076 | Excellent | Good |
| 36 cycles 5 second @ 95°C | 75 min | 0.15 μL | R1: 0.724 R2: 0.386 R3: 0.415 | R1: 0.164 R2: 0.153 R3: 0.155 | R1: 0.343 R2: 0.229 R3: 0.202 | R1: 0.034 R2: 0.020 R3: 0.012 | Acceptable | Failed |
| 37 cycles 5 second @ 95°C | 78 min | 0.15 μL | R1: 0.893 R2: 0.614 R3: 0.592 | R1: 0.187 R2: 0.163 R3: 0.155 | R1: 0.511 R2: 0.325 R3: 0.300 | R1: 0.053 R2: 0.023 R3: 0.022 | Acceptable | Acceptable |
| 38 cycles 5 second @ 95°C | 80 min | 0.15 μL | R1: 0.951 R2: 0.572 R3: 0.710 | R1: 0.181 R2: 0.119 R3: 0.164 | R1: 0.604 R2: 0.429 R3: 0.403 | R1: 0.066 R2: 0.040 R3: 0.037 | Good | Acceptable |
| 39 cycles 5 second @ 95°C | 82 min | 0.15 μL | R1: 1.167 R2: 0.806 R3: 0.812 | R1: 0.250 R2: 0.190 R3: 0.170 | R1: 0.698 R2: 0.546 R3: 0.528 | R1: 0.084 R2: 0.052 R3: 0.056 | Good | Acceptable |
| 40 cycles 5 second @ 95°C | 85 min | 0.15 μL | R1: 1.235 R2: 1.018 R3: 1.038 | R1: 0.238 R2: 0.221 R3: 0.216 | R1: 0.781 R2: 0.559 R3: 0.565 | R1: 0.092 R2: 0.050 R3: 0.057 | Excellent | Good |

Figure 4

METHODS FOR IMPROVED ISOLATION OF GENOMIC DNA TEMPLATES FOR ALLELE DETECTION

RELATED APPLICATIONS

This application is a continuation application of International Application No. PCT/US2014/029466, filed Mar. 14, 2014, which claims priority to U.S. Provisional Patent Application Ser. No. 61/852,357, filed Mar. 15, 2013, and U.S. Provisional Patent Application Ser. No. 61/852,358, filed Mar. 15, 2013. All of these patent applications are incorporated by reference herein in their entireties.

FIELD OF THE APPLICATION

This application generally relates to methods for the isolation and detection of disease-associated genetic alleles. In particular, this application relates to an improved method for the detection of an Avellino corneal dystrophy associated allele.

BACKGROUND

Real-time PCR can be used to detect differences between nucleic acid sequences having substantially identical sequences. Through the use of differentially labeled fluorescent nucleic acid probes, for example one that binds to a wild type sequence and one that binds to a mutant sequence, single nucleotide changes in the human genome can be quickly and reliably detected. This resolving power has been applied to medical diagnostics, where single nucleotide polymorphisms (SNPs), i.e., single base changes found within the coding and/or non-coding sequence of a protein, are correlated to human disease.

However, real-time PCR analysis is highly dependent upon the collection and isolation of high quality samples. Poor sample collection and/or isolation require the use of longer assay conditions and greater amounts of real-time PCR reagents, both of which result in increased costs and reduced productivity. Furthermore, failure of a real-time PCR single nucleotide polymorphism detection assay can result in the need to collect additional samples, causing even greater loss in time and resources.

Accordingly, methods resulting in improved sample collection and isolation, which improve the overall success rate of the assay, reduce the reagents required for the assay, and reduce the need to collect additional samples at later time are highly desirable. Furthermore, methods for performing real-time PCR SNP detection assays with lower amounts of sample material will also reduce the challenges associated with the collection and isolation of high quality samples.

Corneal dystrophy can be an autosomal dominant hereditary disease, which initially presents with blurred vision in the center of a patient's cornea. The blurry vision gradually spreads toward the perimeter of cornea, worsening the patient's vision as they age. There are several types of corneal dystrophy that have been characterized, including Avellino corneal dystrophy (also known as Granular corneal dystrophy, Type2), Granular corneal dystrophy (Type 1), Thiel-Behnke corneal dystrophy, Lattice corneal dystrophy, and Reis-bucklers corneal dystrophy. Corneal dystrophies are known to be caused, at least in some cases, by mutations in the transforming growth factor beta induced (TGFBI, also abbreviated as TGFβI) gene encoding the βIG-H3 protein (also known as TGFBI protein, TGFBIp and keratoepithelin).

Heterozygous patients suffering from Avellino corneal dystrophy have increasing loss in vision with age, becoming severe in the later years of life. Homozygous patients, in contrast, can present with severe to complete loss of vision by six years of age. Avellino corneal dystrophy was first recognized as a distinct type of corneal dystrophy around 1988. Prior to then, it was likely misclassified as Granular corneal dystrophy. Today, Avellino corneal dystrophy is known to be the most common form of stromal corneal dystrophy world-wide. In Korea, Avellino corneal dystrophy is believed to have a prevalence around 1 in 870 people (see Lee, J. H. et al., *Ophthalmic Epidemiol.*, 17:160, 2010; see also Holland, E. J. et al., *Ophthalmology*, 99:1564, 1992; Kennedy, S. M. et al., *Br. J. Ophthalmol.*, 80:489, 1996; Dolmetsch, A. M. et al., *Can. J. Ophthalmol.*, 31:29, 1996; Afshari, N. A. et al., *Arch. Ophthalmol.*, 119:16, 2001; Stewart, H. S. *Hum. Mutat.*, 14:126, 1999).

Previously, it was discovered that heterozygous individuals (e.g., having one wild type TGFBI allele and one mutant TGFBI allele) were highly susceptible to accelerating loss of vision following LASIK surgery. Notably, two years after surgery increased opacity of the cornea was observed in these patients with increasing aggressiveness, eventually resulting in complete loss of vision (Jun, R. M. et al., *Opthalmology*, 111:463, 2004). Previously, eye surgery has been performed with an expectation that LASIK or Excimer Laser surgery would get rid of vision blurriness of a patient suffering from corneal dystrophy. For a hypothetical number of three hundred thousand cases of LASIK surgery, 300 people would have lost their vision, based on $\frac{1}{1000}$ of minimum estimation of heterozygous patients suffering from Avellino corneal dystrophy. Patients who have undergone LASIK surgery are mainly in their 20's and 30's carrying out productive activities; therefore, their vision loss causes serious troubles in both society and economics.

In addition, after approval of LASIK surgery in year 2000 in USA, African American patients suffering from Avellino corneal dystrophy who underwent LASIK surgery have been found to lose eye sight, which infers that plenty of similar cases might be occurring throughout the world.

Therefore, although accurate diagnosis of Avellino corneal dystrophy is required to prevent the progression of Avellino corneal dystrophy by LASIK surgery, the diagnosis of Avellino corneal dystrophy is just conducted by microscopic observation (e.g., slit-lamp examination) of corneal opacity and thus often doctors miss latent symptoms of patients to perform LASIK surgery, which results in vision loss. Therefore, rapid and precise genetic diagnosis of corneal dystrophy is desirable.

A DNA chip for detecting a mutation in TGFBI gene, which is responsible for Avellino corneal dystrophy, was developed (Korean Patent Laid-Open Publication No. 10-2007-0076532). However, the diagnosis of Avellino corneal dystrophy using said DNA chip disadvantageously require several steps, including a step of amplifying DNA in a sample, a step of hybridizing the amplified DNA with the DNA chip, a step of washing the hybridized DNA chip, and a step of detecting a positive response, which can be slow and contribute to errors.

Given the above background, what is needed in the art are improved methods for the collection of biological samples from patients, the extraction of genomic DNA from these samples, and the detection of Avellino corneal dystrophy-related SNPs therefrom.

SUMMARY

Advantageously, the present disclosure provides improved methods for the collection of biological samples, the extraction of genomic DNA from these samples, and the detection of Avellino corneal dystrophy-related SNPs therefrom. These methods improve throughput, decrease assay time, and reduce the costs associated with the detection of disease-related SNP, including Avellino corneal dystrophy-related SNP.

In some aspects, the present disclosure provides improved methods for the detection of alleles associated with human disease. The methods described below decrease the time and cost associated with performing assays that yield medical information about a subject. For example, in some embodiments, the improved methods allow for same-day detection of a genomic marker associated with Avellino corneal dystrophy, at a reduced cost to the patient.

In some embodiments, these advantages are provided by improving methods for the isolation of genomic samples used for allele detection. These improved methods increase the total recovery of genomic DNA from buccal cell samples taken from the patient. In some embodiments, these improved yields are realized by increasing the temperature at which buccal cells from the patient are lysed.

In some embodiments, the methods described below allow for the re-use of patient samples, reducing the need for collecting additional samples when genomic testing needs to be repeated. Traditionally, upon the failure of a genomic test, the subject needs to provide additional samples for re-testing. This can result in the delay of an important test result for several days to weeks. Advantageously, because the methods provided herein improve the efficiency of genomic nucleic acids, patient samples can be reused, potentially saving valuable time and costs associated with collecting additional patient samples.

In some embodiments, the methods described below increase the sensitivity of the detection assay, reducing the amount of sample needed for testing. Reduction in the amount of sample required per reaction increases the number of assays that may be performed on a single sample isolated from a patient, again reducing the possibility that an additional sample will need to be collected from the patient when re-testing is required. The reduction in the required amount of sample also results in a reduction in the amount of reagent needed to perform each assay.

BRIEF DESCRIPTION OF THE DRAWINGS

FIG. 2 provides a list of sequences for forward and reverse PCR primer pairs (SEQ ID NOS:1-24) useful for real-time PCR detection of a single nucleotide polymorphism associated with Avellino corneal dystrophy, in accordance with some embodiments.

FIG. 3 provides a list of sequences for wild type and mutant detection probe pairs (SEQ ID NO:25-42) useful for real-time PCR detection of a single nucleotide polymorphism associated with Avellino corneal dystrophy, in accordance with some embodiments.

FIG. 4 presents the results of experiments performed to identify improved real-time PCR assay conditions for the detection of Avellino corneal dystrophy associated markers.

DETAILED DESCRIPTION

I. Introduction

Figure 1A:
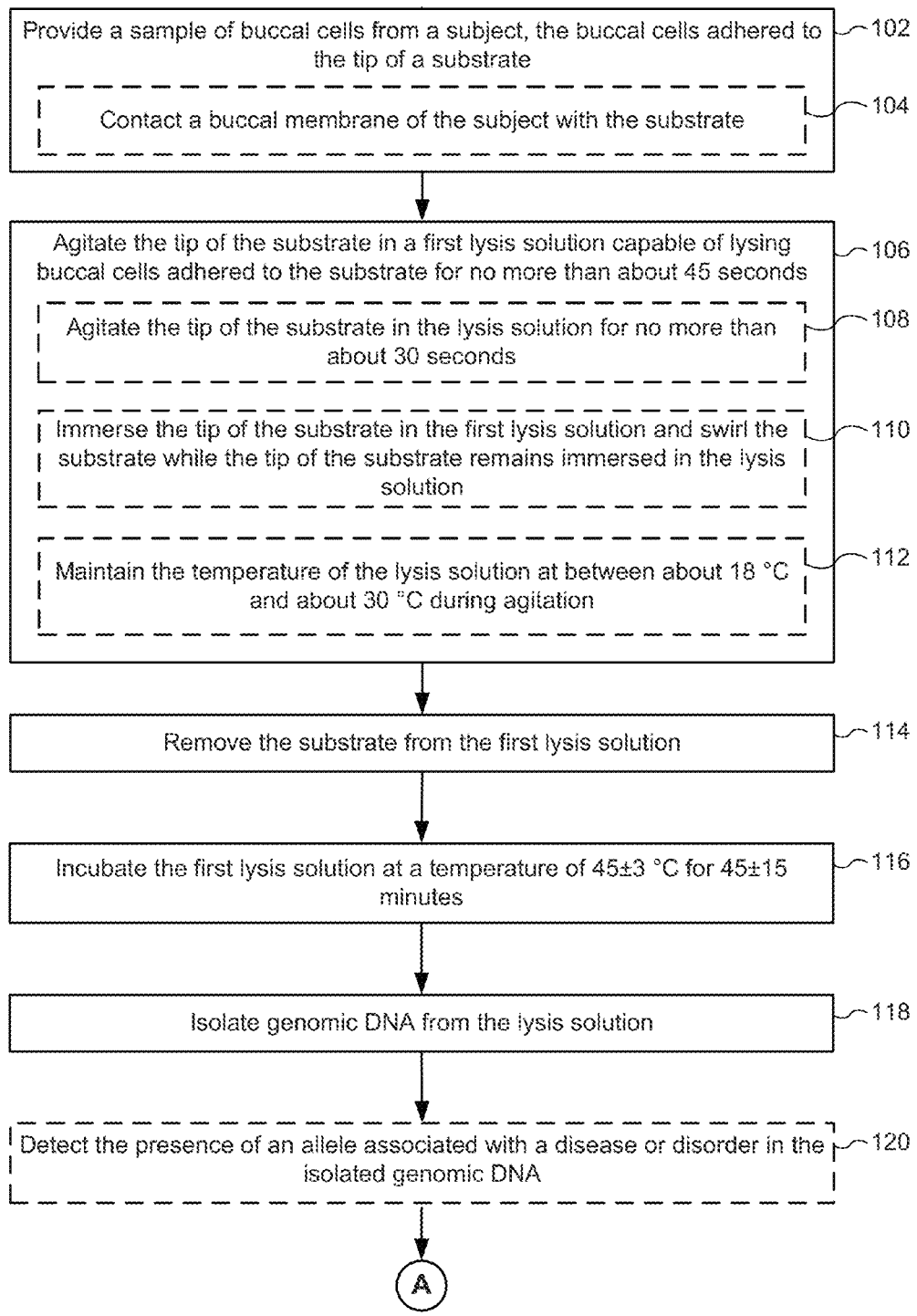
FIGS. 1A-1B illustrates an improved method 100 for the detection of genomic alleles associated with disease, according to some embodiments.

The detection of disease-related SNPs is an increasingly more important tool for the diagnosis and prognosis of various medical conditions. For example, the presence of a single nucleotide change in exon 4 of the TGFBI gene is strongly associated with Avellino corneal dystrophy. It was found that individuals heterozygous for this SNP are at high risk for vision loss following LASIK surgery. While LASIK is a medical procedure that greatly improves many people's quality of life, for individuals carrying the G/A TGFBI SNP, it commonly causes a gradual vision impairment over a four to eighteen month period, which may lead to loss of vision. The vision impairment may occur in a longer or shorter period of time. Fortunately, screening can be performed to identify individuals carrying the mutation who should avoid having the LASIK procedure.

The present disclosure is based at least in part on the discovery of methods that improve sample isolation, preparation, and analysis. In some embodiments, methods are provided which allow for the re-use of patient samples, for example, when an assay fails or additional follow-up testing needs to be performed. In some embodiments, these improved methods include gently swirling a substrate (e.g., a rayon-tipped or cotton-tipped applicator) carrying cells sloughed-off the buccal membrane of the patient in a lysis solution at room temperature for 30-45 seconds (rather than extended incubation for 20 minutes at elevated temperature). The lysis solution is then incubated at 45° C. for 30 minutes to improve lysis and increase the yield of genomic sample. Advantageously, the rayon-tipped or cotton-tipped applicator can then be stored (e.g., frozen or refrigerated) for re-isolation of genomic DNA used for re-testing.

In some embodiments, the improvements provided herein are provided through the use of lower amounts of genomic DNA template for the real-time PCR detection assays. In some embodiments, this is achieved by increasing the number of real-time PCR cycles performed (e.g., at about 40 cycles) and/or by using 3 second denaturation cycle times at 95° C. Advantageously, because the amount of sample required is reduced by these methods, so too are the requirements for the real-time PCR reagents. Because many reagents used in diagnostic assays are proprietary, the reagents can be expensive. Reducing the amount of reagent used can also significantly reduce the costs associated with the reagent.

It is contemplated that all combinations of specific conditions (e.g., sample handling, incubation temperature, reaction volumes, reaction cycle numbers, reaction cycle times, reaction cycle temperatures) for performing each of these individual steps can be used to perform the methods described herein for detecting disease-related SNPs, such as the Avellino corneal dystrophy-related SNP found in exon 4 of the TGFBI gene.

II. Select Definitions

The term "invention" or "present invention" as used herein is not meant to be limiting to any one specific embodiment of the invention but applies generally to any and all embodiments of the invention as described in the claims and specification.

As used herein, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure.

As used herein, the term "polymorphism" and variants thereof refers to the occurrence of two or more alternative genomic sequences or alleles between or among different genomes or individuals. The terms "genetic mutation" or "genetic variation" and variants thereof include polymorphisms.

As used herein the term "single nucleotide polymorphism" ("SNP") and variants thereof refers to a site of one nucleotide that varies between alleles. A single nucleotide polymorphism (SNP) is a single base change or point mutation but also includes the so-called "indel" mutations (insertions or deletions of a nucleotide), resulting in genetic variation between individuals. SNPs, which make up about 90% of all human genetic variation, occur every 100 to 300 bases along the 3-billion-base human genome. However, SNPs can occur much more frequently in other organisms like viruses. SNPs can occur in coding or non-coding regions of the genome. A SNP in the coding region may or may not change the amino acid sequence of a protein product. A SNP in a non-coding region can alter promoters or processing sites and may affect gene transcription and/or processing. Knowledge of whether an individual has particular SNPs in a genomic region of interest may provide sufficient information to develop diagnostic, preventive and therapeutic applications for a variety of diseases. In some embodiments, the present disclosure relates to the detection of a guanine-to-adenine SNP located in exon 4 of the TGFBI gene associated with Avellino corneal dystrophy.

The term "primer" and variants thereof refers to an oligonucleotide that acts as a point of initiation of DNA synthesis in a PCR reaction. A primer is usually about 15 to about 35 nucleotides in length and hybridizes to a region complementary to the target sequence.

The term "probe" and variants thereof (e.g., detection probe) refers to an oligonucleotide that hybridizes to a target nucleic acid in a PCR reaction. Target sequence refers to a region of nucleic acid that is to be analyzed and comprises the polymorphic site of interest.

Unless defined otherwise, all technical and scientific terms used herein have the same meaning as commonly understood by those of ordinary skill in the art to which the invention pertains. Although any methods and materials similar or equivalent to those described herein can be used in the practice or testing of the present invention, various embodiments of methods and materials are specifically described herein.

III. Sample Preparation

In some embodiments, the disclosure provides improved methods for isolating genomic samples used in real-time PCR single nucleotide polymorphism detection assays. In some embodiments, the improved method 100 uses a combination of steps outlined in FIGS. 1A-1B.

In some embodiments, the method includes providing a sample of cells from a subject. In some embodiments, the cells are collected by contacting a cellular surface of a patient with a substrate capable of reversibly immobilizing the cells onto a substrate.

The disclosed methods are applicable to a variety of cell types. In some embodiments, the cell type for use with the disclosed methods include but is not limited to epithelial cells, endothelial cells, connective tissue cells, skeletal muscle cells, endocrine cells, cardiac cells, urinary cells, melanocytes and keratinocytes. In some embodiments, the cells are epithelial cells. In some embodiments, the cells are leukocytes. In some embodiments, the cells are obtained from one or more of: blood, buffy coat, and saliva. In some embodiments, the cells are subcapsular-perivascular (epithelial type 1); pale (epithelial type 2); intermediate (epithelial type 3); dark (epithelial type 4); undifferentiated (epithelial type 5); and large-medullary (epithelial type 6). In some embodiments, the cells are buccal epithelial cells (e.g., epithelial cells collected using a buccal swap). In some embodiments, the sample of cells used in the disclosed methods include any combination of the above identified cell types.

In some embodiments, the method includes providing (102, FIG. 1A) a sample of cells from a subject. In some embodiments, the cells provided are buccal epithelial cells.

The cell samples are collected by any of a variety of methods which allow for reversible binding of the subjects cells to the substrate. In some embodiments, the substrate is employed in a physical interaction with the sample containing the subject's cells in order to reversibly bind the cells to the substrate. In some embodiments, the substrate is employed in a physical interaction with the body of the subject directly in order to reversibly bind the cells to the substrate. In some embodiments, the sample is a buccal cell sample and the sample of buccal cells is collected by contacting (104, FIG. 1A) a buccal membrane of the subject (e.g., the inside of their cheek) with a substrate capable of reversibly immobilizing cells that are dislodged from the membrane. In such embodiments, the swab is rubbed against the inside of the subject's cheek with a force equivalent to brushing a person's teeth (e.g., a light amount of force or pressure). Any method which would allow the subject's cells to be reversibly bound to the substrate is contemplated for use with the disclosed methods.

In some embodiments, the sample is advantageously collected in a non-invasive manner and as such sample collection is accomplished anywhere and by almost anyone. For example, in some embodiments the sample is collected at a physician's office, at a subject's home, or at a facility where LASIK surgery is performed or to be performed. In some embodiments the patient, the patient's doctor, nurses or a physician's assistant or other clinical personnel collects the sample.

In some embodiments the substrate is made of any of a variety of materials to which cells are reversibly bound. Exemplary substrates include those made of rayon, cotton, silica, an elastomer, a shellac, amber, a natural or synthetic rubber, cellulose, BAKELITE, NYLON, a polystyrene, a polyethylene, a polypropylene, a polyacrylonitrile, or other materials or combinations thereof. In some embodiments, the substrate is a swab having a rayon tip or a cotton tip.

The tip of the substrate (e.g., the tip of the rayon swab or cotton swab) is then agitated (106, FIG. 1A) in a lysis solution. In some embodiments, the tip of the substrate is agitated in the lysis solution from about 10 seconds to 60 seconds (1 minute), or about 20 seconds to 60 seconds, about 20 seconds to about 45 seconds, or about 20 seconds to about 30 seconds, about 15 seconds to about 60 seconds, about 15 seconds to about 45 seconds, or about 15 seconds to about 30 seconds, about 10 seconds to about 60 seconds, about 10 seconds to about 45 seconds, or about 10 seconds to about 30 seconds, about 10 seconds to about 15 seconds or about 10 seconds to about 20 seconds. In some embodiments, the agitation occurs for about 60 seconds or about 1 minute. In some embodiments, the agitation occurs for less than a minute (e.g., less than 60 seconds). In some embodiments, the agitation occurs for no more than 15 seconds, 20 seconds, 30 seconds (108, FIG. 1A), 45 seconds or 60 seconds. In some embodiments, the agitation occurs for no more than 45 seconds. In some embodiments, the agitation occurs for no more than 30 seconds. In some embodiments, the agitation occurs for no more than 20 seconds. In some embodiments, the agitation occurs for no more than 15 seconds. However, an agitation can be performed for longer than 60 seconds (e.g., about 120 seconds, 180 seconds, 240 seconds, 300 seconds, 600 seconds, etc.).

In some embodiments, agitation includes any movement of the substrate in the lysis solution. In some embodiments, agitation includes (110, FIG. 1A) immersing the tip of the substrate in the lysis solution and swirling the substrate while the tip of the substrate remains immersed in the lysis solution. In some embodiments, the tip of the substrate (e.g., the tip of the rayon swab or cotton swab) is moved gently in the lysis solution, such that a plurality of buccal cells remains affixed to the substrate for isolation at a later time and/or subsequent time. Such movement in the lysis solution includes swirling motions, side to side motions, up and down motions and/or dipping motions, or any other movement of the substrate in the lysis solutions that results in a plurality of buccal cell remain affixed to the tip while allowing for some buccal cells to be dispersed into the lysis solution.

In some embodiments, the agitation step is performed at room temperature, for instance, temperatures between about 15° C. and about 30° C. (112, FIG. 1A), about 18° C. and about 28° C., about 18° C. and about 25° C. or about 20° C. and about 25° C.

After agitation, the substrate (e.g., a swab with a rayon tip or cotton tip) is removed (114, FIG. 1A) and, in some embodiments, stored for use later, in case re-testing or further (e.g., different or additional) testing is needed. In some embodiments, the substrate (e.g., buccal swab with a rayon tip or cotton tip) is placed in a container and stored frozen. In some embodiments, the substrate (e.g., buccal swab with a rayon tip or cotton tip) is refrigerated. In some embodiments, the substrate is stored at any of a variety of temperatures and for any of a variety of times while still remaining useful for one or more additional extractions.

In some embodiments, the substrate containing the sample is stored for 0 weeks, 1 week, 2 weeks, 3 weeks, 4 weeks, 5 weeks, 6 weeks, 7 weeks, 8 weeks, 9 weeks, 10 weeks, 11 weeks or 12 weeks or more. In some embodiments, the substrate containing the sample is stored for and/or is capable of being stored for 0 weeks to 12 weeks, 1 week to 12 weeks, 2 weeks to 12 weeks, 3 weeks to 12 weeks, 4 weeks to 12 weeks, 5 weeks to 12 weeks, 6 weeks to 12 weeks, 7 weeks to 12 weeks, 8 weeks to 12 weeks, 9 weeks, 10 weeks to 12 weeks, or 11 weeks to 12 weeks. In some embodiments, the substrate containing the sample is stored for 1, 2, 3, 4, 5, 6, 8, 10, 12, 14, 16, 18, 20, 22, 24, 30, or 36 months or more. In some embodiments, the substrate containing the sample is stored for 1 month to 36 months, 2 months to 36 months, 3 months to 36 months, 4 months to 36 months, 5 months to 36 months, 6 months to 36 months, 7 months to 36 months, 8 months to 36 months, 9 months to 36 months, 10 months to 36 months, 12 months to 36 months, 14 months to 36 months, 16 months to 36 months, 18 months to 36 months. In some embodiments, the substrate containing the sample is stored for 1 month to 30 months, 2 months to 30 months, 3 months to 30 months, 4 months to 30 months, 5 months to 30 months, 6 months to 30 months, 7 months to 30 months, 8 months to 30 months, 9 months to 30 months, 10 months to 30 months, 12 months to 30 months, 14 months to 30 months, 16 months to 30 months or 18 months to 30 months. In some embodiments, the substrate containing the sample is stored for 1 month to 24 months, 2 months to 24 months, 3 months to 24 months, 4 months to 24 months, 5 months to 24 months, 6 months to 24 months, 7 months to 24 months, 8 months to 24 months, 9 months to 24 months, 10 months to 24 months, 12 months to 24 months, 14 months to 24 months, 16 months to 24 months, 18 months to 24 months. In some embodiments, the substrate containing the sample is stored for 1 month to 22 months, 2 months to 22 months, 3 months to 22 months, 4 months to 22 months, 5 months to 22 months, 6 months to 22 months, 7 months to 22 months, 8 months to 22 months, 9 months to 22 months, 10 months to 22 months, 12 months to 22 months, 14 months to 22 months, 16 months to 22 months, 18 months to 22 months. In some embodiments, the substrate containing the sample is stored for 1 month to 20 months, 2 months to 20 months, 3 months to 20 months, 4 months to 20 months, 5 months to 20 months, 6 months to 20 months, 7 months to 20 months, 8 to 20 months, 9 to 20 months, 10 months to 20 months, 12 months to 20 months, 14 months to 20 months, 16 months to 20 months, 18 months to 20 months. In some embodiments, the substrate containing the sample is stored for 1 month to 18 months, 2 months to 18 months, 3 months to 18 months, 4 months to 18 months, 5 months to 18 months, 6 months to 18 months, 7 months to 18 months, 8 months to 18 months, 9 months to 18 months, 10 months to 18 months, 12 months to 18 months, 14 months to 18 months, 16 months to 18 months or 17 months to 18 months. In some embodiments, the substrate containing the sample is stored for 1 month to 12 months, 2 months to 12 months, 3 months to 12 months, 4 months to 12 months, 5 months to 12 months, 6 months to 12 months, 7 months to 12 months, 8 months to 12 months, 9 months to 12 months, 10 months to 12 months or 11 months to 12 months.

In some embodiments, the substrate containing the sample is stored at about 2° C., about 3° C., about 4° C., about 5° C., about 6° C., about 7° C., or about 8° C. In some embodiments, the substrate containing the sample is stored at about 2° C. to about 8° C., about 3° C. to about 8° C., about 4° C. to about 8° C., about 5° C. to about 8° C., about 6° C. to about 8° C. or about 7° C. to about 8° C. In some embodiments, the substrate containing the sample is stored at about −25° C., about −24° C., about −23° C., about −22° C., about −21° C., about −20° C., about −19° C., about −18° C., about −17° C., about −16° C. or about −15° C. In some embodiments, the substrate containing the sample is stored at about −25° C. to about −15° C., about −22° C. to about −17° C., about −20° C. to about −15° C. or about −25° C. to about −20° C. In some embodiments, the substrate containing the sample is stored at about −90° C., about −89° C., about −88° C., about −87° C., about −86° C., about −85° C., about −84° C., about −83° C., about −82° C., about −81° C., about −80° C., about −79° C., about −78° C., about −77° C., about −76° C., about −75° C., about −74° C., about −73° C., about −72° C., about −71° C., about −70° C., about −69° C., about −68° C., about −67° C., about −66° C. or about −65° C. In some embodiments, the substrate containing the sample is stored at about −90° C. to about −65° C., about −85° C. to about −65° C., about −80° C. to about −65° C., about −75° C. to about −65° C. or about −70° C. to about −65° C. In some embodiments, the substrate containing the sample is stored at −90° C. to −65° C.

In some embodiments, the substrate containing the sample is freeze-thawed one or more times (e.g., after being frozen, the substrate containing the sample is thawed, used according to the present methods and re-frozen) and used in the present methods. In some embodiments, the substrate containing the sample is freeze-thawed 1, 2, 3, 4, 5, 6, 7, 8, 9, 10, 11, 12, 13, 14, 15, 16, 17, 18, 19, 20 or more times. In some embodiments, the substrate containing the sample is used in the present methods 1, 2, 3, 4, 5, 6, 7, 8, 9, 10, 11, 12, 13, 14, 15, 16, 17, 18, 19, 20 or more times. In some embodiments, the substrate containing the sample is freeze-thawed 1 to 20 times, 2 to 20 times, 3 to 20 times, 4 to 30 times, 5 to 20 times, 6 to 20 times, 7 to 20 times, 8 to 20 times, 9 to 20 times, 10 to 20 times, 11 to 20 times, 12 to 20 times, 13 to 20 times, 14 to 20 times, 15 to 20 times, 16 to 20 times, 17 to 20 times, 18 to 20 times, 19 to 20 times, 5 to 15 times, 5 to 10 times, 1 to 10 times or 1 to 5 times. In some embodiments, the substrate containing the sample is used in the present methods 1 to 20 times, 2 to 20 times, 3 to 20 times, 4 to 30 times, 5 to 20 times, 6 to 20 times, 7 to 20 times, 8 to 20 times, 9 to 20 times, 10 to 20 times, 11 to 20 times, 12 to 20 times, 13 to 20 times, 14 to 20 times, 15 to 20 times, 16 to 20 times, 17 to 20 times, 18 to 20 times, 19 to 20 times, 5 to 15 times, 5 to 10 times, 1 to 10 times or 1 to 5 times. Thus, in some embodiments, the substrate containing the sample is freeze-thawed multiple times (e.g., 3 times) and used in the present methods.

In some embodiments, the substrate containing the sample is stored for 1 week at room temperature or about 15° C. to about 30° C. In some embodiments, the sample is stored for about 1, 2 or 3 weeks at about 2° C. to about 8° C. or about 4° C. In some embodiments, the substrate containing the sample is stored for about 1, 2, 3, 4, 5, 6, 7, 8, 9, 10, 11 or 12 months at about −25° C. to about −15° C. or about −20° C. In some embodiments, the substrate containing the sample is stored for about 1, 2, 3, 4, 5, 6, 7, 8, 9, 10, 11 or 12 months at about −90° C. to about −65° C. or about −80° C.

In some embodiments, the tip of substrate is agitated (122, FIG. 1B) in a second lysis solution capable of lysing buccal ceels adhered to the substrate. In some embodiments, the second lysis solution is identical to the first lysis solution. In some embodiments, the second lysis solution is distinct from the first lysis solution. In some embodiments, the tip of substrate is agitated in a second lysis solution capable of lysing buccal ceels adhered to the substrate after the substrate has been stored frozen and thawed. In some embodiments, agitation includes (124, FIG. 1B) agitating the tip of the substrate in the lysis solution for no more than about 45 seconds. In some embodiments, agitation includes (126, FIG. 1B) immersing the tip of the substrate in the second lysis solution and swirling the substrate while the tip of the substrate remains immersed in the lysis solution. In some embodiments, the temperature of the lysis solution is maintained (128, FIG. 1B) at between about 18° C. and 30° C. during agitation.

In some embodiments, the substrate is removed (130, FIG. 1B) from the second lysis solution. In some embodiments, the second lysis solution is incubated. In some embodiments, the second lysis solution is incubated (132, FIG. 1B) at a temperature of 45±3° C. for 45±15 minutes. In some embodiments, genomic DNA is isolated (134, FIG. 1B) from the second lysis solution. In some embodiments, a presence of an allele associated with a disease or disorder is detected in the isolated genomic DNA.

Figure 1B:
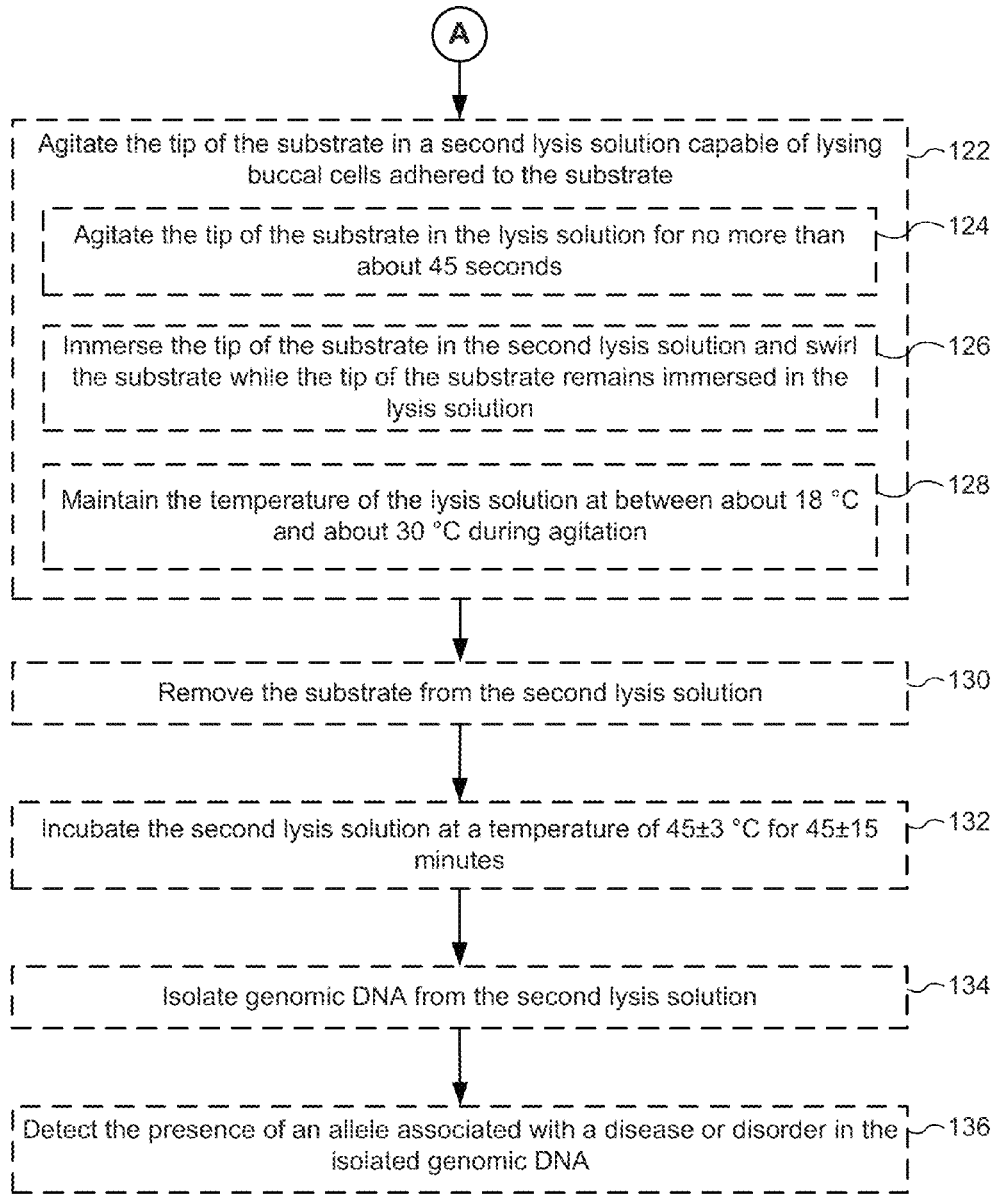

Several features of processes illustrated in FIG. 1A are applicable to processes illustrated in FIG. 1B. For example, various conditions of processes described above with respect to FIG. 1A may be used for processes illustrated in FIG. 1B. For brevity, these details are not repeated herein.

Advantageously and surprisingly, it was found that the reduced number of cells extracted from the substrate is countered by increased extraction of nucleic acids from individual cells. In some embodiments, increased extraction is accomplished by incubating the cells for a longer time as compared to standard practices, incubating the cells at an elevated temperature as compared to standard practices, or a combination of both.

In some embodiments, the increased the extraction of nucleic acids of cells is accomplished by performing the extraction incubation for an increased or longer period of time as compared to standard practice. In some embodiments, the extraction incubation is performed for about 45 minutes, e.g., 45±5, 45±10, 45±15, or 45±20 minutes (116, FIG. 1A). In some embodiments, the extraction incubation is performed for about 25 minutes to about 65 minutes, about 30 minutes to about 60 minutes, about 35 minutes to about 55 minutes, about 45 minutes to about 65 minutes, about 45 minutes to about 55 minutes, or about 40 minutes to about 50 minutes. In some embodiments, the extraction incubation time of according to the invention is about 25 minutes, about 30 minutes, about 35 minutes, about 40 minutes, about 45 minutes, about 50 minutes, about 55 minutes, about 60 minutes or about 65 minutes.

In some embodiments, the increased the extraction of nucleic acids of cells is accomplished by performing the extraction incubation at an increased or higher temperature as compared to standard practice. In some embodiments, the extraction incubation is performed at about 45° C., e.g., 45±2° C., 45±5° C., or 45±10° C. (116, FIG. 1A). In some embodiments, the extraction incubation temperature is about 35° C. to about 55° C., about 40° C. to about 50° C. or about 43° C. to about 47° C. In some embodiments, the extraction temperature is about 43° C., about 44° C., about 45° C., about 46° C., about 47° C., about 48° C., about 49° C., about 50° C., about 51° C., about 52° C., about 53° C., about 54° C. or about 55° C.

In some embodiments, substantially small numbers of cells are released from the substrate for subsequent lysis according to the present methods. In some embodiments, at least 1 cell, at least 2 cells, at least 5 cells, at least 10 cells, at least 15 cells, at least 20 cells, at least 50 cells, at least 75 cells, at least 100 cells, at least 125 cells, at least 150 cells, at least 175 cells, at least 200 cells, at least 250 cells, at least 300 cells, at least 350 cells, at least 400 cells, at least 450 cells, at least 500 cells or more are released from the substrate during agitation.

In some embodiments, about 1 ng/µL to about 50 ng/µL, about 1 ng/µL to about 40 ng/µL, about 1 ng/µL to about 30 ng/µL, about 1 ng/µL to about 20 ng/µL, about 1 ng/µL to about 10 ng/µL, about 1 ng/µL to about 5 ng/µL, about 1 ng/µL to about 4 ng/µL, about 1 ng/µL to about 3 ng/µL or about 1 ng/µL to about 2 ng/µL of nucleic acid with a purity of about 0.55 to 2.00, about 0.6 to about 2.00, about 0.7 to about 2.00 about 0.8 to about 2.00, about 0.9 to about 2.00, about 1.0 to about 2.00 about 1.1 to about 2.00, about 1.2 to about 2.00, about 1.3 to about 2.00, about 1.4 to about 2.00, about 1.5 to about 2.00 about 1.6 to about 2.00 about 1. 7 to about 2.00 about 1.8 to about 2.00 or about 1.9 to about 2.00 is employed with the described methods. In some embodiments, about 1 ng/μL to 50 ng/μL with a purity of about 0.55 to 2.00 is employed with the described methods. In some embodiments, about 1 ng/μL to 40 ng/μL with a purity of about 0.55 to 2.00 is employed with the described methods. In some embodiments, about 1 ng/μL to 30 ng/μL with a purity of about 0.55 to 2.00 is employed with the described methods. In some embodiments, 1 ng/μL to 20 ng/μL with a purity of about 0.55 to 2.00 is employed with the described methods. In some embodiments, 1 ng/μL to 10 ng/μL with a purity of about 0.55 to 2.00 is employed with the described methods. In some embodiments, 1 ng/μL to 5 ng/μL with a purity of about 0.55 to 2.00 is employed with the described methods. In some embodiments, 1 ng/μL to 4 ng/μL with a purity of about 0.55 to 2.00 is employed with the described methods. In some embodiments, 1 ng/μL to 3 ng/μL with a purity of about 0.55 to 2.00 is employed with the described methods. In some embodiments, 1 ng/μL to 2 ng/μL with a purity of about 0.55 to 2.00 is employed with the described methods. In some embodiments, at least about 1 ng/μL with a purity of about 0.55 to 2.00 is employed with the described methods.

IV. Lysis Solutions

A variety of lysis solutions have been described and are known to those of skill in the art. Any of these well known lysis solutions can be employed with the present methods in order to isolate nucleic acids from a sample. Exemplary lysis solutions include those commercially available, such as those sold by INVITROGEN, QIAGEN, LIFE TECHNOLOGIES and other manufacturers, as well as those which can be generated by one of skill in a laboratory setting. Lysis buffers have also been well described and a variety of lysis buffers can find use with the disclosed methods, including for example those described in Molecular Cloning (three volume set, Cold Spring Harbor Laboratory Press, 2012) and Current Protocols (Genetics and Genomics; Molecular Biology; 2003-2013), both of which are incorporated herein by reference for all purposes.

Cell lysis is a commonly practiced method for the recovery of nucleic acids from within cells. In many cases, the cells are contacted with a lysis solution, commonly an alkaline solution comprising a detergent, or a solution of a lysis enzyme. Such lysis solutions typically contain salts, detergents and buffering agents, as well as other agents that one of skill would understand to use. After full and/or partial lysis, the nucleic acids are recovered from the lysis solution.

In some embodiments, cells are resuspended in an aqueous buffer, with a pH in the range of from about pH 4 to about 10, about 5 to about 9, about 6 to about 8 or about 7 to about 9.

In some embodiments, the buffer salt concentration is from about 10 mM to about 200 mM, about 10 mM to about 100 mM or about 20 mM to about 80 mM.

In some embodiments, the buffer further comprises chelating agents such as ethylenediaminetetraacetic acid (EDTA) or ethylene glycol tetraacetic acid (EGTA).

In some embodiments, the lysis solution further comprises other compounds to assist with nucleic acid release from cells such as polyols, including for example but not limited to sucrose, as well as sugar alcohols such as maltitol, sorbitol, xylitol, erythritol, and/or isomalt. In some embodiments, polyols are in the range of from about 2% to about 15% w/w, or about 5% to about 15% w/w or about 5% to about 10% w/w.

In some embodiments, the lysis solutions further comprises surfactants, such as for example but not limited to Triton X-100, SDS, CTAB, X-114, CHAPS, DOC, and/or NP-40. In some embodiments such surfactants are in the range of from about 1% to about 5% w/w, about 1% to about 4% w/w, or about 1% to about 3% w/w.

In embodiments, the lysis solution further comprises chaotropes, such as for example but not limited to urea, sodium dodecyl sulfate and/or thiourea. In some embodiments, the chaotrope is used at a concentration in the range of from about 0.5 M to 8 M, about 1 M to about 6 M, about 2 M to about 6 M or about 1 M to 3 M.

In some embodiments, the lysis solution further comprises one or more additional lysis reagents and such lysis reagents are well known in the art. In some embodiments, such lysis reagents include cell wall lytic enzymes, such as for example but not limited to lysozyme. In some embodiments, lysis reagents comprise alkaline detergent solutions, such as 0.1 aqueous sodium hydroxide containing 0.5% sodium dodecyl sulphate.

In some embodiments, the lysis solution further comprises aqueous sugar solutions, such as sucrose solution and chelating agents such as EDTA, for example the STET buffer. In certain embodiments, the lysis reagent is prepared by mixing the cell suspension with an equal volume of lysis solution having twice the desired concentration (for example 0.2 sodium hydroxide, 1.0% sodium dodecyl sulphate).

In some embodiments, after the desired extent of lysis has been achieved, the mixture comprising lysis solution and lysed cells is contacted with a neutralizing or quenching reagent to adjust the conditions such that the lysis reagent does not adversely affect the desired product. In some embodiments, the pH is adjusted to a pH of from about 5 to about 9, about 6 to about 8, about 5 to about 7, about 6 to about 7 or about 6.5 to 7.5 to minimize and/or prevent degradation of the cell contents, including for example but not limited to the nucleic acids. In some embodiments, when the lysis reagent comprises an alkaline solution, the neutralizing reagent comprises an acidic buffer, for example an alkali metal acetate/acetic acid buffer. In some embodiments, lysis conditions, such as temperature and composition of the lysis reagent are chosen such that lysis is substantially completed while minimizing degradation of the desired product, including for example but not limited to nucleic acids.

In some embodiments, a first, second, third, fourth, fifth, sixth, seventh, eighth, ninth, tenth, eleventh, twelfth, thirteenth, fourteenth, fifteenth or twentieth lysis solution is employed with the methods. In some embodiments, the volume of lysis buffer used is about 10 μL, about 20 μL, about 30 μL, about 40 μL, about 50 μL, about 60 μL, about 70 μL, about 80 μL, about 90 μL, about 100 μL, about 120 μL, about 130 μL, about 140 μL, about 150 μL, 160 μL, about 170 μL, about 180 μL, about 190 μL, about 200 μL, about 220 μL, about 230 μL, about 240 μL, about 250 μL, about 260 μL, about 270 μL, about 280 μL, about 290 μL, about 300 μL, about 320 μL, about 330 μL, about 340 μL, about 350 μL, about 360 μL, about 370 μL, about 380 μL, about 390 μL, about 400 μL, about 500 μL, about 600 μL, about 700 μL, about 800 μL, about 900 μL or about 1000 μL. In some embodiments, the lysis buffer is between about 10 μL and about 400 μL, about 20 μL and about 400 μL, about 50 μL and about 300 μL, about 50 μL and about 200 μL, about 50 μL and about 400 μL, about 100 μL and about 400 μL, about 10 μL about 300 μL, about 100 μL and about 200 μL, about 200 μL and about 500 μL, about 100 μL and about 1000 µL, about 200 µL and about 1000 µL, about 300 µL and about 200 µL, about 500 µL and about 1000 µL or about 600 µL and about 1000 µL.

Any combination of the above can be employed by one of skill, as well as combined with other known and routine methods, and such combinations are contemplated by the present invention.

V. Purification of Nucleic Acids from Lysis Buffer

In some embodiments, the nucleic acids, including for example but not limited to genomic DNA, are isolated from lysis buffer (118, FIG. 1A) prior to performing subsequent analysis. In some embodiments, the nucleic acids are isolated from the lysis buffer prior to the performance of additional analyses, such as for example but not limited to real-time PCR analyses. Any of a variety of methods useful in the isolation of small quantities of nucleic acids are used by various embodiments of the disclosed methods. These include but are not limited to precipitation, gel filtration, density gradients and solid phase binding. Such methods have also been described in for example, Molecular Cloning (three volume set, Cold Spring Harbor Laboratory Press, 2012) and Current Protocols (Genetics and Genomics; Molecular Biology; 2003-2013), incorporated herein by reference for all purposes.

Nucleic Acid precipitation is a well know method for isolation that is known by those of skill in the art. A variety of solid phase binding methods are also known in the art including but not limited to solid phase binding methods that make use of solid phases in the form of beads (e.g., silica, magnetic), columns, membranes or any of a variety other physical forms known in the art. In some embodiments, solid phases used in the disclosed methods reversibly bind nucleic acids. Examples of such solid phases include so-called "mixed-bed" solid phases are mixtures of at least two different solid phases, each of which has a capacity to nucleic acids under different solution conditions, and the ability and/or capacity to release the nucleic acid under different conditions; such as those described in US Patent Application No. 2002/0001812, incorporated by reference herein in its entirety for all purposes. Solid phase affinity for nucleic acids according to the disclosed methods can be through any one of a number of means typically used to bind a solute to a substrate. Examples of such means include but are not limited to, ionic interactions (e.g., anion-exchange chromatography) and hydrophobic interactions (e.g., reversed-phase chromatography), pH differentials and changes, salt differentials and changes (e.g., concentration changes, use of chaotropic salts/agents). Exemplary pH based solid phases include but are not limited to those used in the INVITROGEN ChargeSwitch Normalized Buccal Kit magnetic beads, to which bind nucleic acids at low pH (<6.5) and releases nucleic acids at high pH (>8.5) and mono-amino-N-aminoethyl (MANAE) which binds nucleic acids at a pH of less than 7.5 and release nucleic acids at a pH of greater than 8. Exemplary ion exchange based substrates include but are not limited to DEA-SEPHAROSE™, Q-SEPHAROSE™, and DEAE-SEPHADEX™ from PHARMACIA (Piscataway, N.J.), DOWEX® I from The Dow Chemical Company (Midland, Mich.), AMBERLITE® from Rohm & Haas (Philadelphia, Pa.), DUOLITE® from Duolite International, In. (Cleveland, Ohio), DIALON TI and DIALON TII.

Any individual method is contemplated for use alone or in combination with other methods, and such useful combination are well known and appreciated by those of skill in the art.

VI. Nucleic Acid Analyses

The disclosed methods are used to isolate nucleic acids, such as genomic DNA (gDNA) for a variety of nucleic acid analyses, including genomic analyses. In some embodiments, the method includes detecting the presence of an allele associated with a disease or disorder in the isolated genomic DNA. In some embodiments, such analysis include detection of variety of genetic mutations, which include but are not limited to one or more deletions, insertions, transitions and transversions. In some embodiments, the mutation is a single-nucleotide polymorphism (SNP).

A variety of methods for analyzing such isolated nucleic acids, for example but not limited to genomic DNA (gDNA) are known in the art and include PCR methods, such as real-time PCR analysis, microarray analysis, hybridization analysis and nucleic acid sequence analysis, as well as a variety of other methods where nucleic acid compositions are analyzed and which are known to those of skill in the art. See, for example, Molecular Cloning (three volume set, Cold Spring Harbor Laboratory Press, 2012) and Current Protocols (Genetics and Genomics; Molecular Biology; 2003-2013).

a. Real-Time PCR

For the design of Real-time PCR assays, several parts are coordinated, including the DNA fragment that is flanked by the two primers and subsequently amplified, often referred to as the amplicon, the two primers and the detection probe or probes to be used.

Real-time PCR relies on the visual emission of fluorescent dyes conjugated to short polynucleotides (termed "detection probes") that associate with genomic alleles in a sequence-specific fashion. Real-time PCR probes differing by a single nucleotide can be differentiated in a real-time PCR assay by the conjugation and detection of probes that fluoresce at different wavelengths. Real-time PCR finds use in detection applications (diagnostic applications), quantification applications and genotyping applications.

Several related methods for performing real-time PCR are disclosed in the art, including assays that rely on TaqMan probes (U.S. Pat. Nos. 5,210,015 and 5,487,972, and Lee et al., *Nucleic Acids Res.* 21:3761-6, 1993), molecular beacon probes (U.S. Pat. Nos. 5,925,517 and 6,103,476, and Tyagi and Kramer, *Nat. Biotechnol.* 14:303-8, 1996), self-probing amplicons (scorpions) (U.S. Pat. No. 6,326,145, and Whitcombe et al., *Nat. Biotechnol.* 17:804-7, 1999), Amplisensor (Chen et al., *Appl. Environ. Microbiol.* 64:4210-6, 1998), Amplifluor (U.S. Pat. No. 6,117,635, and Nazarenko et al., *Nucleic Acids Res.* 25:2516-21, 1997, displacement hybridization probes (Li et al., *Nucleic Acids Res.* 30:E5, 2002), DzyNA-PCR (Todd et al., *Clin. Chem.* 46:625-30, 2000), fluorescent restriction enzyme detection (Cairns et al., *Biochem. Biophys. Res. Commun.* 318:684-90, 2004) and adjacent hybridization probes (U.S. Pat. No. 6,174,670 and Wittwer et al., *Biotechniques* 22:130-1, 134-8, 1997).

In some instances, real-time PCR can result in detection of a variety of gene mutations, including for example but not limited to SNPs. In some embodiments, detection of SNPs in specific gene candidates is performed using real-time PCR, based on the use of intramolecular quenching of a fluorescent molecule by use of a tethered quenching moiety. Thus, according to exemplary embodiments, real-time PCR methods also include the use of molecular beacon technology. The molecular beacon technology utilizes hairpin-shaped molecules with an internally-quenched fluorophore whose fluorescence is restored by binding to a DNA target of interest (See, e.g., Kramer, R. et al. *Nat. Biotechnol.* 14:303-308, 1996). In some embodiments, increased binding of the molecular beacon probe to the accumulating PCR product is used to specifically detect SNPs present in genomic DNA.

One of the many suitable genotyping procedures is the TaqMan allelic discrimination assay. In some instances of this assay, an oligonucleotide probe labeled with a fluorescent reporter dye at the 5' end of the probe and a quencher dye at the 3' end of the probe is utilized. The proximity of the quencher to the intact probe maintains a low fluorescence for the reporter. During the PCR reaction, the 5' nuclease activity of DNA polymerase cleaves the probe, and separates the dye and quencher. This results in an increase in fluorescence of the reporter. Accumulation of PCR product is detected directly by monitoring the increase in fluorescence of the reporter dye. The 5' nuclease activity of DNA polymerase cleaves the probe between the reporter and the quencher only if the probe hybridizes to the target and is amplified during PCR. The probe is designed to straddle a target SNP position and hybridize to the nucleic acid molecule only if a particular SNP allele is present.

By way of example, to amplify the Avellino corneal dystrophy associated SNP located in exon 4 of the TGFBI gene, forward and reverse PCR primer pairs (SEQ ID NOS:1 to 24 in FIG. 2) were constructed as described in U.S. Patent Application Serial Number 2012/0077200. In some embodiments, any of the forward and reverse primer pairs disclosed therein are used in the improved methods disclosed herein. In a preferred embodiment, the forward and reverse primer pair of SEQ ID NO:1 (forward) and SEQ ID NO:2 (reverse) are used in the improved methods provided herein.

In order to detect the guanine-to-adenine mutation in exon 4 of TGFBI gene, fluorescently labeled real-time PCR probe pairs for the detection of the wild type ("G") and Avellino corneal dystrophy-associated mutant ("A") allele having nucleotide sequences according to SEQ ID NOS: 25 to 42, as shown in FIG. 3, were constructed as described in U.S. Patent Application Serial Number 2012/0077200. In some embodiments, any of the wild type and mutant probes are used in the improved methods disclosed herein. In a preferred embodiment, the wild type and mutant probe pair of SEQ ID NO:25 (wild type) and SEQ ID NO:26 (mutant) are used in the improved methods provided herein. To differentiate the wild type allele from the disease-associated allele, the wild type probes were labeled with VIC, and the mutant probes were labeled with FAM. The minor groove binder (MGB) was attached to the probe so as to facilitate binding to a complementary gene fragment.

b. Real-Time PCR Cycles

Real-time PCR methods include a variety of steps or cycles as part of the methods for amplification. These cycles include denaturing double-stranded nucleic acids, annealing a forward primer, a reverse primer and a detection probe to the target genomic DNA sequence and synthesizing (i.e., replicating) second-strand DNA from the annealed forward primer and the reverse primer. This three step process is referred to herein as a cycle.

In some embodiments, about 10, 15, 20, 25, 30, 35, 40, 45, 50, 55, or 60 cycles are employed. In some embodiments, about 10 to about 60 cycles, about 20 to about 50 or about 30 to about 40 cycles are employed. In some embodiments, 40 cycles are employed.

In some embodiments, the denaturing double-stranded nucleic acids step occurs at a temperature of about 80° C. to 100° C., about 85° C. to about 99° C., about 90° C. to about 95° C. for about 1 second to about 5 seconds, about 2 seconds to about 5 seconds o about 3 second to about 4 seconds. In some embodiments, the denaturing double-stranded nucleic acids step occurs at a temperature of 95° C. for about 3 seconds.

In some embodiments, the annealing a forward primer, a reverse primer and a detection probe to the target genomic DNA sequence step occurs at about 40° C. to about 80° C., about 50° C. to about 70° C., about 55° C. to about 65° C. for about 15 seconds to about 45 seconds, about 20 seconds to about 40 seconds, about 25 seconds to about 35 seconds. In some embodiments, the annealing a forward primer, a reverse primer and a detection probe to the target genomic DNA sequence step occurs at about 60° C. for about 30 seconds.

In some embodiments, the synthesizing (i.e., replicating) second-strand DNA from the annealed forward primer and the reverse primer occurs at about 40° C. to about 80° C., about 50° C. to about 70° C., about 55° C. to about 65° C. for about 15 seconds to about 45 seconds, about 20 seconds to about 40 seconds, about 25 seconds to about 35 seconds. In some embodiments, the annealing a forward primer, a reverse primer and a detection probe to the target genomic DNA sequence step occurs at about 60° C. for about 30 seconds.

In some embodiments, it was found that about 1 μL, about 2 μL, about 3 μL, about 4 μL or about 5 μL of a genomic DNA sample prepared according to the present methods described herein, are combined with only about 0.05 μL, about 0.10 μL about 0.15 μL, about 0.20 μL, about 0.25 μL or about 0.25 μL of a 30×, 35×, 40×, 45×, 50× or 100× real-time PCR master mix. In some embodiments, it was found that 2 μL of a genomic DNA sample prepared as described above, are combined with only about 0.15 μL of a 40× custom genotyping assay.

While exemplary reactions are described herein, one of skill would understand how to modify the temperatures and times based on the probe design. Moreover, the present methods contemplate any combination of the above times and temperatures.

c. PCR Primers and Primer Design

In some embodiments, primers are tested and designed in a laboratory setting. In some embodiments, primers are designed by computer based in silico methods. Primer sequences are based on the sequence of the amplicon or target nucleic acid sequence that is to be amplified. Shorter amplicons typically replicate more efficiently and lead to more efficient amplification as compared to longer amplicons.

In designing primers, one of skill would understand the need to take into account melting temperature ($T_m$; the temperature at which half of the primer-target duplex is dissociated and becomes single stranded and is an indication of duplex stability; increased $T_m$ indicates increased stability) based on GC and AT content of the primers being designed as well as secondary structure considerations (increased GC content can lead to increased secondary structure). $T_M$'s can be calculated using a variety of methods known in the art and those of skill would readily understand such various methods for calculating $T_M$; such methods include for example but are not limited to those available in online tools such as the $T_M$ calculators available on the World Wide Web at promega.com/techserv/tools/biomath/calc11.htm. Primer specificity is defined by its complete sequence in combination with the 3' end sequence, which is the portion elongated by Taq polymerase. In some embodiments, the 3' end should have at least 5 to 7 unique nucleotides not found anywhere else in the target sequence, in order to help reduce false-priming and creation of incorrect amplification products. Forward and reverse primers typically bind with similar efficiency to the target. In some instances, tools such as NCBI BLAST (located on the World Wide Web at ncbi.nlm.nih.gov) are employed to performed alignments and assist in primer design.

Those of skill in the art would be well aware of the basics regarding primer design for a target nucleic acid sequence and a variety of reference manuals and texts have extensive teachings on such methods, including for example, Molecular Cloning (three volume set, Cold Spring Harbor Laboratory Press, 2012) and Current Protocols (Genetics and Genomics; Molecular Biology; 2003-2013) and Real-time PCR in Microbiology: From Diagnostics to Characterization (Ian M. MacKay, Calster Academic Press; 2007); PrimerAnalyser Java tool available on the World Wide Web at primerdigital.com/tools/PrimerAnalyser.html and Kalendar R, et al. (*Genomics,* 98(2): 137-144 (2011)), all of which are incorporated herein in their entireties for all purposes.

An additional aspect of primer design is primer complexity or linguistic sequence complexity (see, Kalendar R, et al. (*Genomics,* 98(2): 137-144 (2011)). Primers with greater linguistic sequence complexity (e.g., nucleotide arrangement and composition) are typically more efficient. In some embodiments, the linguistic sequence complexity calculation method is used to search for conserved regions between compared sequences for the detection of low-complexity regions including simple sequence repeats, imperfect direct or inverted repeats, polypurine and polypyrimidine triple-stranded cDNA structures, and four-stranded structures (such as G-quadruplexes). In some embodiments, linguistic complexity (LC) measurements are performed using the alphabet-capacity L-gram method (see, A. Gabrielian, A. Bolshoy, *Computer & Chemistry* 23:263-274 (1999) and Y. L. Orlov, V. N. Potapov, Complexity: an internet resource for analysis of DNA sequence complexity, *Nucleic Acids Res.* 32: W628-W633(2004)) along the whole sequence length and calculated as the sum of the observed range (xi) from 1 to L size words in the sequence divided by the sum of the expected (E) value for this sequence length. Some G-rich (and C-rich) nucleic acid sequences fold into four-stranded DNA structures that contain stacks of G-quartets (see, the World Wide Web at quadruplex.org). In some instances, these quadruplexes are formed by the intermolecular association of two or four DNA molecules, dimerization of sequences that contain two G-bases, or by the intermolecular folding of a single strand containing four blocks of guanines (see, P. S. Ho, *PNAS,* 91:9549-9553 (1994); I. A. Il'icheva, V. L. Florent'ev, *Russian Journal of Molecular Biology* 26:512-531(1992); D. Sen, W. Gilbert, *Methods Enzymol.* 211:191-199 (1992); P. A. Rachwal, K. R. Fox, *Methods* 43:291-301 (2007); S. Burge, G. N. Parkinson, P. Hazel, A. K. Todd, K. Neidle, *Nucleic Acids Res.* 34:5402-5415 (2006); A. Guédin, J. Gros, P. Alberti, J. Mergny, *Nucleic Acids Res.* 38:7858-7868 (2010); O. Stegle, L. Payet, J. L. Mergny, D. J. MacKay, J. H. Leon, *Bioinformatics* 25:i374-i382 (2009); in some instances, these are eliminated from primer design because of their low linguistic complexity, LC=32% for $(TTAGGG)_4$.

These methods include various bioinformatics tools for pattern analysis in sequences having GC skew, (G−C)/(G+C), AT skew, (A−T)/(A+T), CG-AT skew, (S−W)/(S+W), or purine-pyrimidine (R−Y)/(R+Y) skew regarding CG content and melting temperature and provide tools for determining linguistic sequence complexity profiles. For example the GC skew in a sliding window of n, where n is a positive integer, bases is calculated with a step of one base, according to the formula, (G−C)/(G+C), in which G is the total number of guanines and C is the total number of cytosines for all sequences in the windows (Y. Benita, et al., *Nucleic Acids Res.* 31:e99 (2003)). Positive GC-skew values indicated an overabundance of G bases, whereas negative GC-skew values represented an overabundance of C bases. Similarly, other skews are calculated in the sequence. Such methods, as well as others, are employed to determine primer complexity in some embodiments.

According to non-limiting example embodiments, real-time PCR is performed using exonuclease primers (TAQMAN® probes). In such embodiments, the primers utilize the 5' exonuclease activity of thermostable polymerases such as Taq to cleave dual-labeled probes present in the amplification reaction (See, e.g., Wittwer, C. et al. Biotechniques 22:130-138, 1997). While complementary to the PCR product, the primer probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal. Non-limiting example fluorescent probes include 6-carboxy-floruescein moiety and the like. Exemplary quenchers include Black Hole Quencher 1 moiety and the like.

A variety of PCR primers can find use with the methods of the present invention. Exemplary primers include but are not limited to those described herein. Primers for use in the disclosed methods are also found in U.S. Patent Application No. 20120077200, which is hereby incorporated by reference for all purposes. In some embodiments, the PCR primers for use in the methods of the present invention include but are not limited to the following listed in Table 1 and find use in the detection of the TGFBI gene. Tables 2 and 3 provide biophysical parameters for each primer, as calculated using the World Wide Web at primerdigital.com/tools/PrimerAnalyser.html.

TABLE 1

Exemplary Primers for the TGFBI gene

| Primer Name | SEQ ID NO: | Primer Sequence |
|---|---|---|
| ACD Fw primer | SEQ ID NO: 1 | 5'-TCC ACC ACC ACT CAG CTG TA |
| ACD Re primer | SEQ ID NO: 2 | 5'-CCA TCT CAG GCC TCA GCT T (60 bp) |
| AV Fw primer | SEQ ID NO: 3 | 5'-TGC AGC CCT ACC ACT CTC AA |

TABLE 1-continued

Exemplary Primers for the TGFBI gene

| Primer Name | SEQ ID NO: | Primer Sequence |
|---|---|---|
| AV Re primer | SEQ ID NO: 4 | 5'-AGG CCT CGT TGC TAG G (150 bp) |
| Real Fw primer | SEQ ID NO: 5 | 5'-TAG TCT CTT ATT CTA ATA GA |
| Real Re primer | SEQ ID NO: 6 | 5'-GCT GCA GAC TCT GTG TTT AA (860 bp) |
| ACD Fw2 primer | SEQ ID NO: 7 | 5'-CCA TCC CTC CTT CTG TCT TCT G |
| ACD Re2 primer | SEQ ID NO: 8 | 5'-CGG GCC CCT CCA TCT C (140 bp) |
| ACD Fw3 primer | SEQ ID NO: 9 | 5'-CAG AGA AGG GAG GGT GTG GTT |
| ACD Re3 primer | SEQ ID NO: 10 | 5'-GGG CGA AGA TGG TGA AGC T (190 bp) |
| ACD Fw4 primer | SEQ ID NO: 11 | 5'-TCC TCG TCC TCT CCA CCT GTA |
| ACD Re4 primer | SEQ ID NO: 12 | 5'-AGC TGG CAA GGA GGC CC |
| ACD Fw5 primer | SEQ ID NO: 13 | 5'-TTT GGG CTT TCC CAC ATG C |
| ACD Re5 primer | SEQ ID NO: 14 | 5'-GGC AGA CGG AGG TCA TCT CA |
| ACD Fw6 primer | SEQ ID NO: 15 | 5'-GTA GTA CCG TGC TCT CTG |
| ACD Re6 primer | SEQ ID NO: 16 | 5'-AGT TCC CCA TAA GAA TCC CCC |
| ACD Fw7 primer | SEQ ID NO: 17 | 5'-GGC TGG ACC CCC AGA GG |
| ACD Re7 primer | SEQ ID NO: 18 | 5'-ACC CCT CGG GGA AGT AAG G |
| ACD Fw8 primer | SEQ ID NO: 19 | 5'-AAC CTT TAC GAG ACC CTG GGA |
| ACD Re8 primer | SEQ ID NO: 20 | 5'-GAC TCC CAT CCA TCA TGC CC |
| ACD Fw9 primer | SEQ ID NO: 21 | 5'-AGT CGT TGG ATC CAC CAC CA |
| ACD Re9 primer | SEQ ID NO: 22 | 5'-GAC GTC ATT TCC TAC TGT TTC AGG |
| ACD Fw10 primer | SEQ ID NO: 23 | 5'-CCC CCC AGA AAC AGC CTG |
| ACD Re10 primer | SEQ ID NO: 24 | 5'-TTC TAA GGG GTT AAG GAG AAA GCT T |

TABLE 2

Biophysical Parameters for Forward Primers

| Forward Primer | Length | Tm1 | Tm2 | GC Content | % Com-plexity | PCR Effic. |
|---|---|---|---|---|---|---|
| SEQ ID NO: 1 | 19 | 55.4 | 57.8 | 57.9 | 70 | 70 |
| SEQ ID NO: 3 | 20 | 57.1 | 58 | 55 | 81 | 66 |
| SEQ ID NO: 5 | 20 | 40.2 | 45.7 | 25 | 73 | 38 |
| SEQ ID NO: 7 | 22 | 55.9 | 60.2 | 54.5 | 62 | 43 |
| SEQ ID NO: 9 | 21 | 57.5 | 60.2 | 57.1 | 64 | 40 |
| SEQ ID NO: 11 | 21 | 57.6 | 60.2 | 57.1 | 66 | 57 |
| SEQ ID NO: 13 | 19 | 55.4 | 55.7 | 52.6 | 81 | 80 |
| SEQ ID NO: 15 | 18 | 50.6 | 55.3 | 55.6 | 75 | 66 |
| SEQ ID NO: 17 | 17 | 57.8 | 62.2 | 76.5 | 74 | 60 |
| SEQ ID NO: 19 | 21 | 56.6 | 58.2 | 52.4 | 82 | 73 |
| SEQ ID NO: 21 | 20 | 57.4 | 58 | 55 | 78 | 46 |
| SEQ ID NO: 23 | 18 | 56.5 | 59.9 | 66.7 | 69 | 69 |
| Avg | 19.67 | 54.96 | 57.80 | 56.05 | 72.69 | 59.85 |
| Median | 20 | 56.55 | 58.1 | 55.3 | 73.5 | 63 |
| Std Dev | 1.50 | 5.00 | 4.24 | 11.78 | 6.84 | 14.10 |

TABLE 3

Biophysical Parameters for Reverse Primers

| Reverse Primer | Length | Tm1 | Tm2 | GC Content | % Com-plexity | PCR Effic. |
|---|---|---|---|---|---|---|
| SEQ ID NO: 2 | 19 | 55.5 | 57.8 | 57.9 | 72 | 52 |
| SEQ ID NO: 4 | 16 | 52.1 | 54.5 | 62.5 | 78 | 78 |
| SEQ ID NO: 6 | 20 | 52.4 | 53.9 | 45 | 84 | 41 |
| SEQ ID NO: 8 | 16 | 55.2 | 59.6 | 75 | 63 | 53 |
| SEQ ID NO: 10 | 19 | 56.5 | 57.8 | 57.9 | 78 | 69 |
| SEQ ID NO: 12 | 17 | 58.5 | 59.8 | 70.6 | 74 | 66 |
| SEQ ID NO: 14 | 20 | 57.6 | 60.1 | 60 | 84 | 74 |
| SEQ ID NO: 16 | 21 | 54.9 | 58.2 | 52.4 | 71 | 51 |
| SEQ ID NO: 18 | 19 | 56.6 | 60 | 63.2 | 78 | 60 |
| SEQ ID NO: 20 | 20 | 56.5 | 60.1 | 60 | 65 | 65 |
| SEQ ID NO: 22 | 24 | 55.5 | 58.7 | 45.8 | 88 | 67 |
| SEQ ID NO: 24 | 25 | 55.3 | 57.2 | 40 | 74 | 40 |
| Avg | 19.69 | 55.61 | 58.13 | 57.33 | 76.54 | 60.69 |
| Median | 19.5 | 55.5 | 58.45 | 58.95 | 76 | 62.5 |
| Std Dev | 2.77 | 1.86 | 2.10 | 10.33 | 7.52 | 12.30 |

In some embodiments, the real-time PCR primers for use with the disclosed methods have a linguistic sequence complexity of at least 70%, at least 72%, at least 75%, at least 77%, at least 80%, at least 82%, at least 85%, at least 88%, at least 90%, at least 92%, at least 95%, at least 97% or at least 99%.

d. Detection Probe Design and Detection Probes

A variety of detection probes can find use with the disclosed methods and are employed for genotyping and/or for quantification. Detection probes commonly employed by those of skill in the art include but are not limited to hydrolysis probes (also known as Taq-Man probes, 5' nuclease probes or dual-labeled probes), hybridization probes, and Scorpion primers (which combine primer and detection probe in one molecule). In some embodiments, detection probe design is determined by one of skill in the art based on the desired probe target such that the probe is compatible with the PCR primers employed (e.g., primers and probes should not interfere with one another's functions in the real-time PCR assay). In some embodiments, probes are designed to have higher Tm's than the primers in order to promote efficient signal production. $T_m$'s are calculated using any of a variety of methods known in the art and those of skill would readily understand such various methods for calculating Tm; such methods include for example those available in online tools such as the calculators available on the World Wide Web at promega.com/techserv/tools/biomath/calc11.htm. In some embodiments, the increased Tm of the detection probe provides that the detection probe has bound before the primers are elongated by the polymerase.

In some embodiments, detection probes contain various modifications. In some embodiments, detection probes include modified nucleic acid residues, such as but not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and 3' alkyl substitutions.

In some embodiments, the detection probe has increased affinity for a target sequence due to modifications. Such detection probes include detection probes with increased length, as well as detection probes containing chemical modifications. Such modifications include but are not limited to 2'-fluoro (2'-deoxy-2'-fluoro-nucleosides) modifications, LNAs (locked nucleic acids), PNAs (peptide nucleic acids), ZNAs (zip nucleic acids), morpholinos, methylphosphonates, phosphoramidates, polycationic conjugates and 2'-pyrene modifications. In some embodiments, the detector probes contains one or more modifications including 2'fluoro modifications (aka, 2'-Deoxy-2'-fluoro-nucleosides), LNAs (locked nucleic acids), PNAs (peptide nucleic acids), ZNAs (zip nucleic acids), morpholinos, methylphosphonates, phosphoramidates, and/or polycationic conjugates.

In some embodiments, the detection probes contain detectable moieties, such as those described herein as well as any detectable moieties known to those of skill in the art. Such detectable moieties include for example but are not limited to fluorescent labels and chemiluminescent labels. Examples of such detectable moieties can also include members of FRET pairs. In some embodiments, the detection probe contains a detectable entity.

Examples of fluorescent labels include but are not limited to AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); 6-FAM (6-Carboxyfluorescein), 5(6)-FAM cadaverine; 5-FAM cadaverine; 5(6)-FAM ethylenediamme; 5-FAM ethylenediamme; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4',5'-dichloro-2',7'-dimethoxyfluorescein); 5-CR1 lO (5-Carboxyrhodamine 110); 6-CR1 lO (6-Carboxyrhodamine 110); 5-CR6G (5-Carboxyrhodamine 6G); 6-CR6G (6-Carboxyrhodamine 6G); 5(6)-Caroxyrhodamine 6G cadaverine; 5(6)-Caroxyrhodamine 6G ethylenediamme; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamme; 6-TAMRA ethylenediamme; 5-TMR C6 maleimide; 6-TMR C6 maleimide; TR C2 maleimide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof.

Examples of chemiluminescent labels include but are not limited to those labels used with Southern Blot and Western Blot protocols (see, for e.g., Sambrook and Russell, Molecular Cloning: A Laboratory Manual, (3rd ed.) (2001); incorporated by reference herein in its entirety). Examples include but are not limited to -(2'-spiroadamantane)-4-methoxy-4-(3"-phosphoryloxy)phenyl-1,2-dioxetane (AM-PPD); acridinium esters and adamantyl-stabilized 1,2-dioxetanes, and derivatives thereof.

The labeling of probes is known in the art. The labeled probes are used to hybridize within the amplified region during amplification. The probes are modified so as to avoid them from acting as primers for amplification. The detection probe is labeled with two fluorescent dyes, one capable of quenching the fluorescence of the other dye. One dye is attached to the 5' terminus of the probe and the other is attached to an internal site, so that quenching occurs when the probe is in a non-hybridized state.

Typically, real-time PCR probes consist of a pair of dyes (a reporter dye and an acceptor dye) that are involved in fluorescence resonance energy transfer (FRET), whereby the acceptor dye quenches the emission of the reporter dye. In general, the fluorescence-labeled probes increase the specificity of amplicon quantification.

Real-time PCR that are used in some embodiments of the disclosed methods also include the use of one or more hybridization probes (i.e., detection probes), as determined by those skilled in the art, in view of this disclosure. By way of non-limiting example, such hybridization probes include but are not limited to one or more of those provided in the described methods. Exemplary probes such as the HEX channel and/or FAM channel probes, are understood by one skilled in the art.

According to example embodiments, detection probes and primers are conveniently selected e.g., using an in silico analysis using primer design software and cross-referencing against the available nucleotide database of genes and genomes deposited at the National Center for Biotechnology Information (NCBI). Some additional guidelines may be used for selection of primers and/or probes in some embodiments. For example, in some embodiments, the primers and probes are selected such that they are close together, but not overlapping. In some embodiments, the primers may have the same (or close $T_M$) (e.g., between about 58° C. and about 60° C.). In some embodiments, the TM of the probe is approximately 10° C. higher than that selected for the TM of the primers. In some embodiments, the length of the probes and primers is selected to be between about 17 and 39 base pairs, etc. These and other guidelines are used in some instances by those skilled in the art in selecting appropriate primers and/or probes.

Probes for use in the methods of the present invention include but are not limited to the following exemplary probes listed in Table 4.

TABLE 4

Exemplary Probes for the TGFBI gene

| Probe Name | SEQ ID NO: | Probe Sequence |
|---|---|---|
| Normal probe 1 | SEQ ID NO: 25 | VIC-CAC GGA CCG CAC GGA-NFQ (15 bp) |
| Mutant probe 1 | SEQ ID NO: 26 | FAM-CAC GGA CCA CAC GGA-NFQ |
| Normal probe 2 | SEQ ID NO: 27 | VIC-ACA CGG ACC GCA CG-NFQ |
| Mutant probe 2 | SEQ ID NO: 28 | FAM-ACA CGG ACC ACA CG-NFQ (14 bp) |
| Normal probe 3 | SEQ ID NO: 29 | VIC-TAC ACG GAC CGC A-NFQ |
| Mutant probe 3 | SEQ ID NO: 30 | FAM-TAC ACG GAC CAC A-NFQ (13 bp) |
| Normal probe 4 | SEQ ID NO: 31 | VIC-CTG TAC ACG GAC CGC ACG-NFQ |
| Mutant probe 4 | SEQ ID NO: 32 | FAM-CTG TAC ACG GAC CAC ACG-NFQ (18 bp) |
| Normal probe 5 | SEQ ID NO: 33 | VIC-CTG TAC ACG GAC CGC ACG GAG-NFQ |
| Mutant probe 5 | SEQ ID NO: 34 | FAM-CTG TAC ACG GAC CAC ACG GAG-NFQ (21 bp) |
| Normal probe 6 | SEQ ID NO: 35 | VIC-GCT GTA CAC GGA CCG CAC GGA GAA-NFQ |
| Mutant probe 6 | SEQ ID NO: 36 | FAM-GCT GTA CAC GGA CCA CAC GGA GAA-NFQ |
| Normal probe 7 | SEQ ID NO: 37 | VIC-ACC GCA CGG AGA AGC-NFQ |
| Mutant probe 7 | SEQ ID NO: 38 | FAM-ACC ACA CGG AGA AGC-NFQ |
| Normal probe 8 | SEQ ID NO: 39 | VIC-ACC GCA CGG AGA AGC TGA GGC-NFQ |
| Mutant probe 8 | SEQ ID NO: 40 | FAM-ACC ACA CGG AGA AGC TGA GGC-NFQ |
| Normal probe 9 | SEQ ID NO: 41 | VIC-ACC GCA CGG AGA AGC TGA GGC CTG-NFQ |
| Mutant probe 9 | SEQ ID NO: 42 | FAM-ACC ACA CGG AGA AGC TGA GGC CTG-NFQ |

VII. Diagnostic Tests

In some embodiments, diagnostic testing is employed to determine one or more genetic conditions by detection of any of a variety of mutations. In some embodiments, diagnostic testing is used to confirm a diagnosis when a particular condition is suspected based on for example physical manifestations, signs and/or symptoms as well as family history information. In some embodiments, the results of a diagnostic test assist those of skill in the medical arts in determining an appropriate treatment regimen for a given patient and allow for more personalized and more effective treatment regimens. In some embodiments, a treatment regimen include any of a variety of pharmaceutical treatments, surgical treatments, lifestyles changes or a combination thereof as determined by one of skill in the art.

The nucleic acids obtained by the disclosed methods are useful in a variety of diagnostic tests, including tests for detecting mutations such as deletions, insertions, transversions and transitions. In some embodiments, such diagnostics are useful for identifying unaffected individuals who carry one copy of a gene for a disease that requires two copies for the disease to be expressed, identifying unaffected individuals who carry one copy of a gene for a disease in which the information could find use in developing a treatment regimen, preimplantation genetic diagnosis, prenatal diagnostic testing, newborn screening, genealogical DNA test (for genetic genealogy purposes), presymptomatic testing for predicting adult-onset disorders such as Huntington's disease, presymptomatic testing for estimating the risk of developing adult-onset cancers and Alzheimer's disease, confirmational diagnosis of a symptomatic individual, and/or forensic/identity testing. In some embodiments, the present methods find use in the detection of corneal dystrophy, for example through detection of Avellino corneal dystrophy-related SNPs, such as those that result in R124 mutations in the TGFBI gene (including for example but not limited to an R124H mutation caused by a G to A transition at nucleotide 418 of TGFBI gene also referred to as a C(G/A)C SNP).

In some embodiments, newborn screening includes any genetic screening employed just after birth in order to identify genetic disorders. In some embodiments, newborn screening finds use in the identification of genetic disorders so that a treatment regimen is determined early in life. Such tests include but are not limited to testing infants for phenylketonuria and congenital hypothyroidism.

In some embodiments, carrier testing is employed to identify people who carry a single copy of a gene mutation. In some cases, when present in two copies, the mutation can cause a genetic disorder. In some cases, one copy is sufficient to cause a genetic disorder. In some cases, the presence of two copies is contra-indicated for a particular treatment regimen, such as the presence of the Avellino mutation and pre-screening prior to performing surgical procedures in order to ensure the appropriate treatment regimen is pursued for a give patient. In some embodiments, such information is also useful for individual contemplating procreation and assists individuals with making informed decisions as well as assisting those skilled in the medical arts in providing important advice to individual patients.

In some embodiments, predictive and presymptomatic types of testing are used to detect gene mutations associated with a variety of disorders. In some cases, these tests are helpful to people who have a family member with a genetic disorder, but who may exhibit no features of the disorder at the time of testing. In some embodiments, predictive testing identifies mutations that increase a person's chances of developing disorders with a genetic basis, including for example but not limited to certain types of cancer. In some embodiments, presymptomatic testing is useful in determining whether a person will develop a genetic disorder, before any physical signs or symptoms appear. The results of predictive and presymptomatic testing provide information about a person's risk of developing a specific disorder and help with making decisions about an appropriate medical treatment regimen. Predictive testing is also employed, in some embodiments, to detect mutations which are contra-indicated with certain treatment regimens, such as the presence of the Avellino mutation being contra-indicated with performing laser eye surgery, such as a refractive surgery (e.g., LASIK, LASEK, PTK, and PRK). For example, patients exhibiting the Avellino mutation should not undergo a refractive surgey (LASIK, LASEK, PTK, and PRK).

In some embodiments, diagnostic testing also includes pharmacogenomics which includes genetic testing that determines the influence of genetic variation s on drug response. Information from such pharmacogenomic analyses finds use in determining and developing an appropriate treatment regimen. Those of skill in the medical arts employ information regarding the presence and/or absence of a genetic variation in designing appropriate treatment regimen.

In some embodiments, diseases whose genetic profiles are determined using the methods of present invention include but are not limited to corneal dystrophy, cancer, diabetes mellitus, hypertension, schizophrenia, and most common congenital malformations, such as cleft lip, cleft palate, neural tube defects, Achondroplasia, Alpha-1 Antitrypsin Deficiency, Antiphospholipid Syndrome, Autism, Autosomal Dominant Polycystic Kidney Disease, Charcot-Marie-Tooth, Colon cancer, Cri du chat, Crohn's Disease, Cystic fibrosis, Dercum Disease, Down Syndrome, Duane Syndrome, Duchenne Muscular Dystrophy, Factor V Leiden Thrombophilia, Familial Hypercholesterolemia, Familial Mediterranean Fever, Fragile X Syndrome, Gaucher Disease, Hemochromatosis, Hemophilia, Holoprosencephaly, Huntington's disease, Klinefelter syndrome, Marfan syndrome, Myotonic Dystrophy, Neurofibromatosis, Noonan Syndrome, Osteogenesis imperfecta, Parkinson's disease, Phenylketonuria, Poland Anomaly, Porphyria, Progeria, Retinitis Pigmentosa, Severe Combined Immunodeficiency (SCID), Sickle cell disease, Spinal Muscular Atrophy, Tay-Sachs, Thalassemia, Trimethylaminuria, Turner Syndrome, Velocardiofacial Syndrome, WAGR Syndrome, Wilson Disease, as well as any other disease with a genetic component. Corneal dystrophies include but are not limited to Avellino corneal dystrophy, Granular corneal dystrophy (Type 2), Thiel-Behnke corneal dystrophy, Lattice corneal dystrophy, and Reis-bucklers corneal dystrophy. Cancers include but are not limited to carcinoma, sarcoma, blastoma, lymphoma, leukemia and germ cell tumors. In some embodiments, the cancer include but is not limited to head and neck, skin, colon, oral, glioblastoma, breast, laryngeal, esophageal, endothelial, endometrial, ovarian, lung, urogenital, rectal, prostate, kidney, melanoma, renal, pancreatic, gastrointestinal, blood, liver, uterine and brain as well as viral induced cancers such as papilloma virus-induced cancer.

In some embodiments, the present methods find use in development of personalized medicine treatment regimens by providing the genomic DNA which is used in determining the genetic profile for an individual. In some embodiments, such genetic profile information is employed by those skilled in the art in order determine and/or develop a treatment regimen. In some embodiments, the presence and/or absence of various genetic variations and mutations identified in nucleic acids isolated by the described methods are used by those of skill in the art as part of a personalized medicine treatment regimen or plan. For example, in some embodiments, information using the disclosed methods is compared to databases or other established information in order to determine a diagnosis for a specified disease and/or determine a treatment regimen. In some cases, the information regarding the presence or absence of a genetic mutation in a particular patient is compared to a database or other standard source of information in order to make a determination regarding a proposed treatment regimen. In some cases, the presence of a genetic mutation indicates pursuing a particular treatment regimen. In some cases the absence of a genetic mutation indicates not pursuing a particular treatment regimen.

In some embodiments, information regarding the presence and/or absence of a particular genetic mutation is used to determine the treatment efficacy of treatment with the therapeutic entity, as well as to tailor treatment regimens for treatment with therapeutic entity. In some embodiments, information regarding the presence and/or absence of a genetic mutation is employed to determine whether to pursue a treatment regimen. In some embodiments, information regarding the presence and/or absence of a genetic mutation is employed to determine whether to continue a treatment regimen. In some embodiments, the presence and/or absence of a genetic mutation is employed to determine whether to discontinue a treatment regimen. In other embodiments, the presence and/or absence of a genetic mutation is employed to determine whether to modify a treatment regimen. In some embodiments the presence and/or absence of a genetic mutation is used to determine whether to increase or decrease the dosage of a treatment that is being administered as part of a treatment regimen. In other embodiments, the presence and/or absence of a genetic mutation is used to determine whether to change the dosing frequency of a treatment administered as part of a treatment regimen. In some embodiments, the presence and/or absence of a genetic mutation is used to determine whether to change the number of dosages per day, per week, times per day of a treatment. In some embodiments the presence and/or absence of a genetic mutation is used to determine whether to change the dosage amount of a treatment. In some embodiments, the presence and/or absence of a genetic mutation is determined prior to initiating a treatment regiment and/or after a treatment regimen has begun. In some embodiments, the presence and/or absence of a genetic mutation is determined and compared to predetermined standard information regarding the presence or absence of a genetic mutation.

In some embodiments, a composite of the presence and/or absence of more than one genetic mutation is generated using the disclosed methods and such composite includes any collection of information regarding the presence and/or absence of more than one genetic mutation. In some embodiments, the presence or absence of 2 or more, 3 or more, 4 or more, 5 or more, 6 or more, 7 or more, 8 or more, 9 or more, 10 or more, 20 or more, 30 or more or 40 or more genetic mutations is examined and used for generation of a composite. Exemplary information in some embodiments includes nucleic acid or protein information, or a combination of information regarding both nucleic acid and/or protein genetic mutations. Generally, the composite includes information regarding the presence and/or absence of a genetic mutation. In some embodiments, these composites are used for comparison with predetermined standard information in order to pursue, maintain or discontinue a treatment regimen.

VIII. Examples

Example 1: Real-Time PCR Conditions for Improving Signal with Small DNA Quantities To identify real-time PCR conditions that provided improved signal when using small quantities of isolated genomic DNA and PCR reagents, an experiment was performed varying the denaturation time and number of real-time PCR cycles performed. Briefly, genomic samples were prepared by lysing human cells collected with a buccal swab according to standard collection practices. The buccal swabs were briefly swirled in lysis solution (e.g., for about 30 seconds) and frozen for re-use at a later time. Lysis solution containing cells recovered from the buccal swab was then incubated at 45° C. for 30 minutes. After incubation, genomic DNA was recovered using ChargeSwitch® magnetic bead-based nucleic acid purification (Life Technologies) according to the manufacturer's instructions. The commercially available Omega E.Z.N.A.® Tissue DNA was used to recover genomic DNA from oral epithelial cells collected on buccal swabs. The Omega E.Z.N.A.® Tissue DNA Kit employs silica membrane technology accompanied by a specialized buffer system for purify genomic DNA from collected cells.

Real-time PCR assays designed to detect a C(G/A)C single nucleotide polymorphism (SNP) in the TGFBI gene, associated with Avellino corneal dystrophy, were performed using reduced volumes (2 µL) of genomic material isolated from buccal cells and reduced amounts of a 40× concentrated custom genotyping assay (0.1 µL to 0.2 µL) containing forward (SEQ ID NO:1) and reverse (SEQ ID NO:2) primers designed to amplify the Avellino corneal dystrophy SNP-containing region of the TGFBI gene; and fluorescently labeled wild-type (SEQ ID NO:25) and mutant (SEQ ID NO:26) real-time PCR probes.

Real-time PCR assays were performed using either an ABI 7500 Fast Real-Time PCR system (Applied Biosystems) or a StepOnePlus real-time PCR system (Applied Biosystems) in singlicate with 36 to 40 PCR cycles. Each cycle included either 3 or 5 second denaturation times. As shown in FIG. 4, the use of 40 PCR cycles in the reactions more than compensated for the smaller amounts of starting material. Remarkably, the shorter 3 second denaturation times worked as well, if not better, than standard 5 second steps. Taken together, the results demonstrate that the methods disclosed herein allow for efficient detection of an Avellino corneal dystrophy-associated SNP using fewer numbers of cells, reduced levels of genomic DNA, and reduced real-time PCR reagents.

It was found that reduced amounts of genomic material (e.g., DNA) could be used by altering the real-time PCR assay. For example, it was found that 2 µL of a genomic DNA sample prepared as described above, could be combined with only about 0.15 µL of a 40X custom genotyping assay. In some cases, this was achieved by increasing the number of PCR cycles performed in the assay to about 40. The increased time required to perform the additional PCR cycles was counteracted by reducing the denaturation time of the PCR cycle to about 3 seconds. The denaturation cycle of the PCR reaction is performed at 95° C. The real-time PCR assay was performed using a forward PCR primer having a nucleotide sequence of SEQ ID NO:1 and a reverse PCR primer having a nucleotide sequence of SEQ ID NO:2. The wild type detection probe used in the assay had a nucleotide sequence of SEQ ID NO:25 and the mutant detection probe used in the assay had a nucleotide sequence of SEQ ID NO:26.

As compared to standard procedures for detecting single nucleotide polymorphisms, these methods reduced the time and cost associated with medical diagnostics.

Example 2: Stability Study Protocol

This Stability Study protocol was developed and included test requirements for reagent stability and freeze thaw cycles.

The reagents used for testing (DNA extraction and real-time PCR) at Avellino Lab USA, Inc. (Avellino) were tested in this stability study to establish product stability. The appropriate reagent expiration dates were determined through stability testing at various temperature conditions as shown in Examples 5-10.

In addition to the reagents, stability testing was performed on the commercial buccal swab samples and DNA extracted from buccal swabs. Experiments were performed to establish stability and performance of buccal swabs and DNA according to their appropriate storage condition with freeze thaw cycles.

The example below outlines the process of testing the stability of the reagents, buccal swabs, and DNA extracted from buccal swabs and was the protocol used in Examples 5-10.

Reagents

The following reagents were used in Examples 5-10, including Omega E.Z.N.A. Tissue DNA Kit, TaqMan Genotyping Master Mix and Custom TaqMan SNP Genotyping Assays.

Samples

The following samples were examined in Examples 5-10, including buccal swabs and extracted DNA from buccal swabs.

Definitions for terms used in Examples 5-10, include the following:

RT=Room Temperature set from 15° C. to 30° C.

4° C. Refrigerator=Temperature set from 2° C. to 8° C.

−20° C. Freezer=Temperature set from −25° C. to −15° C.

−80° C. Freezer=Temperature set from −90° C. to −65° C.

Buccal Swab=A swab (e.g., Rayon, nylon, cotton, etc.) used to collect buccal epithelial cells Extracted DNA=DNA extracted from buccal epithelial cells The procedure used the following reagents and samples. Reagents used included Omega E.Z.N.A. Tissue DNA Kit, TaqMan Genotyping Master Mix and Custom TaqMan SNP Genotyping Assays. Samples used included buccal swabs and extracted DNA from buccal swabs. Alternatively, transport swabs made by Copan Diagnostics, Inc. could be used.

TABLE 5

Reagent and Material Information

| Name | Vendor | Part Number | Storage Conditions |
|---|---|---|---|
| Omega E.AZ.N.A. Tissue DNA Kit | Omega | 101319-018 | Room Temperature |
| TaqMan Genotyping Master Mix | Applied Biosystems | 4371355 | 2° C. to 8° C. |
| Custom TaqMan SNP Genotyping Assays | Applied Biosystems | 4332072 | −15° C. to −25° C. |
| Buccal Swabs | Good Vista Medical and Health Products Co., Ltd. | NA | RT<br>2° C. to 8° C.<br>−25° C. to −15° C.<br>−90° C. to −65° C. |
| Extracted DNA | NA | NA | 2° C. to 8° C.<br>−25° C. to −15° C.<br>−90° C. to −65° C. |

Procedure

Buccal Swabs and Extracted DNA for Stability Testing

Specimens were tested for stability to determine the time and conditions when the resultant genotype becomes compromised. These studies were carried out longitudinally.

Freshly collected donor swabs were used for this study. Three different sample swabs for each condition were tested.

Pooled the DNAs from the Accuracy study. There were 70 NN Normal genotype DNA samples in addition to the swab stability DNA samples. Made 5 plates with 20 wells per plate and 100 μL DNA per well.

One plate was stored at 4° C. Refrigerator. One plate was stored frozen in the −20° C. Freezer. The total number of freeze thaw cycles was 8, spreading over a period of 3 months. One plate was stored frozen in the −80° C. Freezer. The total number of freeze thaw cycles was 10, spreading over a period of one year. Two plates were stored frozen in the −80° C. Freezer for 6 month and 1 year data points. These plates were tested with the freeze thawed plate to evaluate the freeze thaw effect on DNA.

After Day 0, samples were stored at the various temperatures described in the following table. Each sample was run on the data collection days indicated in the following table and the freeze thaw cycles were recorded.

TABLE 6

Buccal Swabs

| Storage | Data Collection Days |
|---|---|
| 4° C. Refrigerator | 0, 1 week, 2 weeks, 3 weeks, 4 weeks, 6 weeks, 8 weeks, 10 weeks, 12 weeks |
| Room Temperature | 0, 1 week, 2 weeks, 3 weeks, 4 weeks, 6 weeks, 8 weeks, 10 weeks, 12 weeks |
| −20° C. Freezer | 0, 1 week, 2 weeks, 3 weeks, 4 weeks, 6 weeks, 8 weeks, 10 weeks, 12 weeks, 6 months, 8 months, 10 months, 12 months |
| −80° C. Freezer | 0, 1 week, 2 weeks, 3 weeks, 4 weeks, 6 weeks, 8 weeks, 10 weeks, 12 weeks, 6 months, 8 months, 10 months, 12 months |

TABLE 7

Extracted DNA Samples in 96-Well Plate

| Storage | Freeze thaw cycles | Data Collection Days |
|---|---|---|
| 4° C. Refrigerator | N/A | 0, 1 week, 2 weeks, 3 weeks, 4 weeks, 6 weeks, 8 weeks, 10 weeks, 12 weeks |
| −20° C. Freezer | Cycle 1 to 8 | 0, 1 week, 2 weeks, 3 weeks, 4 weeks, 6 weeks, 8 weeks, 10 weeks, 12 weeks, 6 months, 8 months, 10 months, 12 months |
| −80° C. Freezer | Cycle 1 to 10 | 0, 1 week, 2 weeks, 3 weeks, 4 weeks, 6 weeks, 8 weeks, 10 weeks, 12 weeks, 6 months, 8 months, 10 months, 12 months |

Reagent Stability Study

Sequestered one lot for each of the following reagents: Omega Tissue DNA kit, TaqMan Genotyping Master Mix and Custom TaqMan SNP Genotyping Assays.

Used the same reagents for the buccal swab and extracted DNA stability tests.

Interpretation

Evaluate the Real-Time PCR Result of Each Allele

The result for each allele must fall within the established sample ranges. If any result falls outside of the sample ranges, the particular portion of the study will be discontinued and the stability will be determined by the data point.

TABLE 8

Sequestered Reagent Information

| Reagents | Lot Number | Storage | Volume |
|---|---|---|---|
| Omega Tissue DNA Kit | D33960205241210CN050312-C2719 | 15° C. to 30° C. | 1 Kit |
| TaqMan Genotyping Master Mix | 1204073 | 2° C. to 8° C. | 3 kits |
| Custom TaqMan SNP Genotyping Assays | P120727-004 D07<br>P120814-006 H01 | −25° C. to −15° C. | 1 kit<br>1 kit |

TABLE 9

Control Reagent Information

| Reagents | Lot Number | Expected Genotype | Confirmed by TaqMan |
|---|---|---|---|
| NN Control {purified DNA isolated from a buccal swab of a normal individual used as a process control from Extraction to PCR analysis; TGFBI R124R Normal} | ALU-0912-006 | NN Normal | Yes |
| HN Control {purified DNA isolated from whole blood sample of a known Heterozygous individual; TGFBI R124R Heterozygous} | ALU-0912-007 | HN Heterozygous | Yes |
| HH Control {DNA cloned, purified and characterized by Bionics Co., Ltd, (ISO0911) in Seoul, Korea; TGFBI R124H homozygous} | ALU-0912-008 | HH Homozygous | Yes |

Example 3

This example provides the procedure regarding how the DNA extraction from buccal epithelial swabs was performed for Examples 5-10.

Procedures

Testing Procedures

Pretreatment.

Added 1.0 mL PBS to 1.5 mL micro centrifuge tubes using a repeater pipette with 12.5 mL syringe. Swirled swab in PBS and wrang swab dry. Centrifuged tube at 13,000 RPM for 2 minutes. While centrifuging, labeled the column and prepared two sets of elution tubes and one set of 1.5 mL micro centrifuge tubes. Checked for pellet. Discarded supernatant with pipette and was careful not to lose any pellet.

DNA Extraction.

Added 200 µL TL Buffer using a repeater pipette with 5.0 mL syringe. Added 25 µL reconstituted OB Protease, vortex to mix. Incubated in heat block at 56° C. (acceptable temperature range 50°-60° C.) for 7 minutes. Mixed tubes at around 3 minutes. Added 250 µL BL Buffer, using a repeater pipette with 12.5 mL syringe. Added 250 µL Ethanol, using a repeater pipette with 12.5 mL syringe. Inverted the tubes for 15 times in the plastic holding block. Checked volume while mixing. Quick spun at no more than 250 RPM. Pipetted content from tube to column. Made sure tube identification numbers matched. Centrifuged the column at 13,000 RPM for 1 minute. Discarded the collection tubes and inserted column into a new 2 mL collection tube. Added 500 µL HB Buffer, using a repeater pipette with 12.5 mL syringe. Centrifuged at 13,000 RPM for 1 minute. Discarded the collection tubes and inserted into new collection tubes. Added 700 µL DNA Wash Buffer using a repeater pipette with 12.5 mL syringe. Centrifuged at 13,000 RPM for 1 minute, discarded liquid and put back into the same collection tube. Added second 700 µL DNA Wash Buffer using a repeater pipette with 12.5 mL syringe. Centrifuged at 13,000 RPM for 1 minute. Discarded liquid and placed tube back into the collection tubes.

Drying Step.

Centrifuged tubes at 13,000 RPM for 2 minutes. Discarded collection tubes and put columns in 1.5 mL micro centrifuge tubes, kept caps open. Incubated in heat block at 56° C. (acceptable temperature range 50°-60° C.) for 1 minute. Sniffed to determine if there was any Ethanol left at the end of the 1 minute. Incubated more if necessary. Added 100 µL distilled water to elude in heat block, using a repeater pipette with 5 mL syringe (Dial 1). Closed caps. Incubated at 56° C. (acceptable temperature range 50°-60° C.) for 2 minutes. Spun down at 13,000 RPM for 1 minute, with column caps closed and 1.5 mL lids open. Discarded columns and horizontally placed groups of 6 micro centrifuge tubes vertically on the tube rack.

DNA Quantification by TECAN NanoQuant Infinite M200 PRO.

Pipette 100 µL of the eluents to a clear 96-well UV plate that has been appropriately labeled. The "Magellan" program, provided with the TECAN system, was employed for obtaining quantification measurements. The TECAN system was commercially available (see, the World Wide Web at tecan.com; Tecan Trading AG, Switzerland).

DNA Concentration and Purity Limits.

Concentration and Purity limits were established. The appropriate concentration range that can yield accurate result is 1 ng/µL to 50 ng/µL and the purity range is 0.55 to 2.00. Any sample falls outside of this limit will need to be repeated from the extraction process.

Example 4: PCR Procedures

This example provides the real-time PCR procedures used in Examples 5 through 10. These examples employed the Applied Biosystems 7500/7500 Fast Real-Time PCR System and the Applied Biosystems StepOne and StepOnePlus Real-Time PCR System, both of which are commercially available from Applied Biosystems (Life Technologies Corporation, USA).

Procedures

Master Mix (MM) Preparation.

Prepared the MM in a 1.5 mL micro centrifuge tube. Added specified amount of Taq Genotyping Master Mix. Added specified amount of water. Added specified amount of Primer (40X Assay Mix). Mixed the MM by flicking and then a quick spin.

Plate Preparation.

Placed a 96-well PCR plate (that has been appropriately labeled) onto a support base. Added 8.0 µL MM to each well by using the automatic pipette or Rainin manual pipette. Added 2.0 µL of sample to the appropriate well by using the 10 µL 12 channel multichannel pipette. Added appropriate controls. Made sure they have been mixed and spun down. Placed in the order of Normal (NN)→Negative (NTC)→Heterozygous (FIN)→Homozygous (HH)→Negative (NTC). Covered PCR plate with ABI Optical Adhesive Film and made sure it was secure around the perimeter of the wells. Spun plate at 1000 RPM for 1 minute, checked for bubbles. If bubbles were present, flicked and re-spun.

Instrument Operation.

Powered on the PCR instrument to be used, 7500 Fast or StepOnePlus and prepare for use. Samples run: NN (Positive Control Allele1/Allele1); NTC (Negative Control); FIN (Positive Control Allele1/Allele2); HH (Allele2/Allele2); and NTC (Negative Control). Set-up for running the following cycling stages: Pre-PCR Read (Holding Stage)→60° C. for 30 seconds; Holding Stage→95° C. for 10 minutes; Cycling Stage→36 cycles of 95° C. for 3 seconds and 60° C. for 30 seconds; and Post-PCR Read (Holding Stage) →60° C. for 30 seconds. Loaded the PCR plate into the instrument and start run.

Example 5: Swab Stability at 0 Through 6 Week Time Points

This example provides exemplary stability study data. The study was designed to determine the acceptable stabilities of commercial buccal swabs, DNA extracted from buccal swabs and various reagents used for testing.

Buccal Swabs

As indicated in Table 10, buccal swabs were stored at various temperatures during the procedures of the present example.

TABLE 10

Buccal Storage Conditions

| Storage | Data Collection Days |
|---|---|
| 4° C. Refrigerator | 0, 1 week, 2 weeks, 3 weeks, 4 weeks, 6 weeks |
| Room Temperature | 0, 1 week, 2 weeks, 3 weeks, 4 weeks, 6 weeks |
| −20° C. Freezer | 0, 1 week, 2 weeks, 3 weeks, 4 weeks, 6 weeks |
| −80° C. Freezer | 0, 1 week, 2 weeks, 3 weeks, 4 weeks, 6 weeks |

Buccal swabs were then stored and thawed at various temperatures and time points as indicated in Table 11 below prior to DNA extraction. After the appropriate time at the indicated temperature, the buccal swab was thawed and DNA was extracted in 96-well plate format from the buccal swab.

TABLE 11

Extracted DNA Samples in 96-Well Plate

| Storage | Freeze thaw cycles | Data Collection Days |
|---|---|---|
| 4° C. Refrigerator | N/A | 0, 1 week, 2 weeks, 3 weeks, 4 weeks, 6 weeks |
| −20° C. Freezer | Cycle 1 to 8 | 0, 1 week, 2 weeks, 3 weeks, 4 weeks, 6 weeks |
| −80° C. Freezer | Cycle 1 to 10 | 0, 1 week, 2 weeks, 3 weeks, 4 weeks, 6 weeks |

Results

Results collected from the first seven data points are summarized in the following tables.

Week 1 Time Point

TABLE 12

0 Time Point PCR Results

| Sample Type | Storage Condition | Instruments (7500 Fast or StepOnePlus) | Avg Allele 1 (Range = 0.44 to 1.81) | Avg Allele 2 (Range = 0.027 to 0.249) | Freeze Thaw Cycle | Pass/Fail |
|---|---|---|---|---|---|---|
| Extracted DNA | 4° C. | 7500 Fast | 1.636 | 0.247 | N/A | Pass |
| Extracted DNA | 4° C. | StepOnePlus | 0.985 | 0.079 | N/A | Pass |
| Extracted DNA | −20° C. | 7500 Fast | 1.508 | 0.216 | N/A | Pass |
| Extracted DNA | −20° C. | StepOnePlus | 0.935 | 0.077 | N/A | Pass |
| Extracted DNA | −80° C. | 7500 Fast | 1.530 | 0.218 | N/A | Pass |
| Extracted DNA | −80° C. | StepOnePlus | 0.925 | 0.079 | N/A | Pass |
| Extracted DNA | −80° C. (6 mo) | 7500 Fast | 1.479 | 0.197 | N/A | Pass |
| Extracted DNA | −80° C. (6 mo) | StepOnePlus | 0.872 | 0.065 | N/A | Pass |
| Extracted DNA | −80° C. (1 yr) | 7500 Fast | 1.433 | 0.180 | N/A | Pass |
| Extracted DNA | −80° C. (1 yr) | StepOnePlus | 0.793 | 0.050 | N/A | Pass |
| Buccal Swabs | For all storage condition | 7500 Fast | 1.582 | 0.226 | N/A | Pass |
| Buccal Swabs | For all storage condition | StepOnePlus | 0.910 | 0.087 | N/A | Pass |

Week 1 Time Point Conclusion

TABLE 13 week 1 Time Point PCR Results

| Sample Type | Storage Condition | Instruments (7500 Fast or StepOnePlus) | Avg Allele 1 (Range = 0.44 to 1.81) | Avg Allele 2 (Range = 0.027 to 0.249) | Freeze Thaw Cycle | Pass/Fail |
|---|---|---|---|---|---|---|
| Extracted DNA | 4° C. | 7500 Fast | 1.329 | 0.177 | N/A | Pass |
| Extracted DNA | 4° C. | StepOnePlus | 0.881 | 0.066 | N/A | Pass |
| Extracted DNA | −20° C. | 7500 Fast | 1.329 | 0.186 | 1 | Pass |
| Extracted DNA | −20° C. | StepOnePlus | 0.852 | 0.082 | 1 | Pass |
| Extracted DNA | −80° C. | 7500 Fast | 1.515 | 0.226 | 1 | Pass |
| Extracted DNA | −80° C. | StepOnePlus | 0.914 | 0.094 | 1 | Pass |
| Buccal Swabs | RT | 7500 Fast | 1.240 | 0.167 | N/A | Pass |
| Buccal Swabs | RT | StepOnePlus | 0.725 | 0.055 | N/A | Pass |
| Buccal Swabs | 4° C. | 7500 Fast | 1.236 | 0.182 | N/A | Pass |
| Buccal Swabs | 4° C. | StepOnePlus | 0.687 | 0.052 | N/A | Pass |
| Buccal Swabs | −20° C. | 7500 Fast | 1.040 | 0.160 | N/A | Pass |
| Buccal Swabs | −20° C. | StepOnePlus | 0.648 | 0.040 | N/A | Pass |
| Buccal Swabs | −80° C. | 7500 Fast | 1.407 | 0.233 | N/A | Pass |
| Buccal Swabs | −80° C. | StepOnePlus | 0.762 | 0.066 | N/A | Pass |

All Extracted DNA, Buccal Swabs, and reagents yielded reliable results in the various storage conditions for 1 week. Therefore, all are stable for 1 week at the various temperatures.

Week 2 Time Point

TABLE 14 week 2 Time Point PCR Results

| Sample Type | Storage Condition | Instruments (7500 Fast or StepOnePlus) | Avg Allele 1 (Range = 0.44 to 1.81) | Avg Allele 2 (Range = 0.027 to 0.249) | Freeze Thaw Cycle | Pass/Fail |
|---|---|---|---|---|---|---|
| Extracted DNA | 4° C. | 7500 Fast | 1.167 | 0.186 | N/A | Pass |
| Extracted DNA | 4° C. | StepOnePlus | 0.877 | 0.066 | N/A | Pass |
| Extracted DNA | −20° C. | 7500 Fast | 1.046 | 0.154 | 2 | Pass |
| Extracted DNA | −20° C. | StepOnePlus | 0.789 | 0.068 | 2 | Pass |
| Extracted DNA | −80° C. | 7500 Fast | 1.165 | 0.173 | 2 | Pass |
| Extracted DNA | −80° C. | StepOnePlus | 0.862 | 0.078 | 2 | Pass |
| Buccal Swabs | RT | 7500 Fast | 0.379 | 0.063 | N/A | Fail |
| Buccal Swabs | RT | StepOnePlus | 0.247 | 0.010 | N/A | Fail |
| Buccal Swabs | 4° C. | 7500 Fast | 1.424 | 0.209 | N/A | Pass |
| Buccal Swabs | 4° C. | StepOnePlus | 0.783 | 0.062 | N/A | Pass |
| Buccal Swabs | −20° C. | 7500 Fast | 1.346 | 0.189 | N/A | Pass |
| Buccal Swabs | −20° C. | StepOnePlus | 0.826 | 0.060 | N/A | Pass |
| Buccal Swabs | −80° C. | 7500 Fast | 1.658 | 0.247 | N/A | Pass |
| Buccal Swabs | −80° C. | StepOnePlus | 0.910 | 0.088 | N/A | Pass |

Week 2 Time Point Conclusion

The room temperature swabs showed less reliable results than those stored at lower temperatures. Therefore, the stability of buccal swabs stored at room temperature was 1 week. No further time points were taken for buccal swabs stored at room temperature.

All Extracted DNA, Buccal Swabs (other than the Room Temperature swabs), and reagents yielded reliable results in the various storage conditions for the 2 week time point.

Therefore, the stability was determined to be 2 weeks at various refrigerated and colder temperatures.

Week 3 Time Point

TABLE 15 week 3 Time Point PCR Results

| Sample Type | Storage Condition | Instruments (7500 Fast or StepOnePlus) | Avg Allele 1 (Range = 0.44 to 1.81) | Avg Allele 2 (Range = 0.027 to 0.249) | Freeze Thaw Cycle | Pass/Fail |
|---|---|---|---|---|---|---|
| Extracted DNA | 4° C. | 7500 Fast | 1.507 | 0.217 | N/A | Pass |
| Extracted DNA | 4° C. | StepOnePlus | 0.816 | 0.051 | N/A | Pass |
| Extracted DNA | −20° C. | 7500 Fast | 1.461 | 0.204 | 3 | Pass |
| Extracted DNA | −20° C. | StepOnePlus | 0.840 | 0.075 | 3 | Pass |
| Extracted DNA | −80° C. | 7500 Fast | 1.502 | 0.204 | 3 | Pass |
| Extracted DNA | −80° C. | StepOnePlus | 0.851 | 0.079 | 3 | Pass |
| Buccal Swabs | 4° C. | 7500 Fast | 1.514 | 0.233 | N/A | Pass |
| Buccal Swabs | 4° C. | StepOnePlus | 0.847 | 0.060 | N/A | Pass |
| Buccal Swabs | −20° C. | 7500 Fast | 1.525 | 0.235 | N/A | Pass |
| Buccal Swabs | −20° C. | StepOnePlus | 0.943 | 0.065 | N/A | Pass |
| Buccal Swabs | −80° C. | 7500 Fast | 1.674 | 0.243 | N/A | Pass |
| Buccal Swabs | −80° C. | StepOnePlus | 0.967 | 0.076 | N/A | Pass |

Week 3 Time Point Conclusion:

All Extracted DNA, Buccal Swabs (other than the Room Temperature swabs), and reagents yielded reliable results in the various storage conditions for 3 week. Therefore, the stability was determined to be 3 weeks at various refrigerated and colder temperatures.

Week 4 Time Point

TABLE 16 week 4 Time Point PCR Results:

| Sample Type | Storage Condition | Instruments (7500 Fast or StepOnePlus) | Avg Allele 1 (Range = 0.44 to 1.81) | Avg Allele 2 (Range = 0.027 to 0.249) | Freeze Thaw Cycle | Pass/Fail |
|---|---|---|---|---|---|---|
| Extracted DNA | 4° C. | 7500 Fast | 1.590 | 0.225 | N/A | Pass |
| Extracted DNA | 4° C. | StepOnePlus | 0.914 | 0.065 | N/A | Pass |
| Extracted DNA | −20° C. | 7500 Fast | 1.526 | 0.206 | 4 | Pass |
| Extracted DNA | −20° C. | StepOnePlus | 0.894 | 0.085 | 4 | Pass |
| Extracted DNA | −80° C. | 7500 Fast | 1.551 | 0.200 | 4 | Pass |
| Extracted DNA | −80° C. | StepOnePlus | 0.884 | 0.080 | 4 | Pass |
| Buccal Swabs | 4° C. | 7500 Fast | 1.358 | 0.202 | N/A | Pass |
| Buccal Swabs | 4° C. | StepOnePlus | 0.713 | 0.060 | N/A | Fail |
| Buccal Swabs | −20° C. | 7500 Fast | 1.445 | 0.199 | N/A | Pass |
| Buccal Swabs | −20° C. | StepOnePlus | 0.810 | 0.065 | N/A | Pass |
| Buccal Swabs | −80° C. | 7500 Fast | 1.845 | 0.290 | N/A | Pass |
| Buccal Swabs | −80° C. | StepOnePlus | 0.963 | 0.092 | N/A | Pass |

Week 4 Time Point Conclusion:

One of the 4° C. temperature swabs showed unreliable result (Allele 1 was 0.33). Therefore, the stability of buccal swabs stored refrigerated at 4° C. temperature was determined to be 3 weeks. This part of study was discontinued.

All Extracted DNA, Buccal Swabs (other than the 4° C. Temperature swabs), and reagents yielded reliable results in the various storage conditions at 4 weeks. Therefore, the stability was determined to be 4 weeks at all test temperatures for the DNA extracts and at −20° C. and −80° C. for the Buccal Swabs.

Week 6 Time Point

TABLE 17

Week 6 Time Point PCR Results

| Sample Type | Storage Condition | Instruments (7500 Fast or StepOnePlus) | Avg Allele 1 (Range = 0.44 to 1.81) | Avg Allele 2 (Range = 0.027 to 0.249) | Freeze Thaw Cycle | Pass/Fail |
|---|---|---|---|---|---|---|
| Extracted DNA | 4° C. | 7500 Fast | 1.664 | 0.229 | N/A | Pass |
| Extracted DNA | 4° C. | StepOnePlus | 0.957 | 0.085 | N/A | Pass |
| Extracted DNA | −20° C. | 7500 Fast | 1.407 | 0.188 | 5 | Pass |
| Extracted DNA | −20° C. | StepOnePlus | 0.806 | 0.069 | 5 | Pass |
| Extracted DNA | −80° C. | 7500 Fast | 1.473 | 0.220 | 5 | Pass |
| Extracted DNA | −80° C. | StepOnePlus | 0.878 | 0.073 | 5 | Pass |
| Buccal Swabs | −20° C. | 7500 Fast | 1.341 | 0.179 | N/A | Pass |
| Buccal Swabs | −20° C. | StepOnePlus | 0.732 | 0.046 | N/A | Pass |
| Buccal Swabs | −80° C. | 7500 Fast | 1.590 | 0.227 | N/A | Pass |
| Buccal Swabs | −80° C. | StepOnePlus | 0.913 | 0.072 | N/A | Pass |

Week 6 Time Point Conclusion:

All Extracted DNA, Buccal Swabs (other than the Room Temperature and 4° C. Temperature swabs), and reagents yielded reliable results in the various storage conditions for 6 week. Therefore, the stability was determined to be 6 weeks at all test temperatures for the DNA extracts with 5 Freeze/Thaw Cycles and at −20° C. and −80° C. for the Buccal Swabs.

Summary Conclusions

The primary acceptance criteria were the Allele 1 and Allele 2 ranges established from the Validation study. The mean results Allele 1 and Allele 2 were calculated at various storage temperatures. The data verified the following stability claim:

TABLE 18

Summary of Stability Information

| Material and Storage Conditions | Stability | Freeze/Thaw Cycles |
|---|---|---|
| Extracted DNA at 4° C. | 6 weeks | N/A |
| Extracted DNA at −20° C. | 6 weeks | 5 |
| Extracted DNA at −80° C. | 6 weeks | 5 |
| Omega Tissue DNA Kit at Room Temperature | 6 weeks | N/A |
| TaqMan Genotyping Master Mix at 2° C. to 8° C. | 6 weeks | N/A |

TABLE 18-continued

Summary of Stability Information

| Material and Storage Conditions | Stability | Freeze/Thaw Cycles |
|---|---|---|
| Custom TaqMan SNP Genotyping Assays at −25° C. to −15° C. | 6 weeks | N/A |
| Buccal Swabs at Room Temperature | 1 week | N/A |
| Buccal Swabs at 4° C. Temperature | 3 weeks | N/A |
| Buccal Swabs at −20° C. Temperature | 6 weeks | N/A |
| Buccal Swabs at −80° C. Temperature | 6 weeks | N/A |

Example 6: Stability Study at 8 Weeks, 10 Weeks and 12 Weeks

This example provides exemplary stability study data continuing from the Study in Example 5. The study was designed to determine the acceptable stabilities of commercial buccal swabs, DNA extracted from buccal swabs and various reagents used for testing. This example contains a summary of the data generated during week 8, week 10, and week 12 of a stability study performed.

Buccal Swabs

As indicated in Table 19, buccal swabs were stored at various temperatures during the procedures of the present example.

TABLE 19

Storage Conditions and Data Collection Days

| Storage | Data Collection Days |
|---|---|
| 4° C. Refrigerator | 8 weeks, 10 weeks, 12 weeks |
| Room Temperature | 8 weeks, 10 weeks, 12 weeks |
| −20° C. Freezer | 8 weeks, 10 weeks, 12 weeks |
| −80° C. Freezer | 8 weeks, 10 weeks, 12 weeks |

Buccal swabs were then stored and thawed at various temperatures and time points as indicated in Table 20 below prior to DNA extraction. After the appropriate time at the indicated temperature, the buccal swab was thawed and DNA was extracted in 96-well plate format from the buccal swab.

TABLE 20

Storage, Freeze Thaw Cycles and Data Collection Days

| Storage | Freeze thaw cycles | Data Collection Days |
|---|---|---|
| 4° C. Refrigerator | N/A | 8 weeks, 10 weeks, 12 weeks |
| −20° C. Freezer | Cycle 1 to 8 | 8 weeks, 10 weeks, 12 weeks |
| −80° C. Freezer | Cycle 1 to 10 | 8 weeks, 10 weeks, 12 weeks |

Results

Results from week 8, week 10, and week 12 data points are summarized in the following tables.

Week 8 Time Point

TABLE 21 week 8 Time Point PCR Results

| Sample Type | Storage Condition | Instruments (7500 Fast or StepOnePlus) | Avg Allele 1 (Range ≥−2SD 0.44) | Avg Allele 2 (Range ≥−2SD 0.027) | Freeze Thaw Cycle | Pass/Fail |
|---|---|---|---|---|---|---|
| Extracted DNA | 4° C. | 7500 Fast | 1.728 | 0.232 | N/A | Pass |
| Extracted DNA | 4° C. | StepOnePlus | 0.888 | 0.117 | N/A | Pass |
| Extracted DNA | −20° C. | 7500 Fast | 1.486 | 0.234 | 6 | Pass |
| Extracted DNA | −20° C. | StepOnePlus | 0.668 | 0.085 | 6 | Pass |
| Extracted DNA | −80° C. | 7500 Fast | 1.721 | 0.264 | 6 | Pass |
| Extracted DNA | −80° C. | StepOnePlus | 0.881 | 0.126 | 6 | Pass |
| Buccal Swabs | −20° C. | 7500 Fast | 1.277 | 0.188 | N/A | Pass |
| Buccal Swabs | −20° C. | StepOnePlus | 0.706 | 0.041 | N/A | Pass |
| Buccal Swabs | −80° C. | 7500 Fast | 1.296 | 0.212 | N/A | Pass |
| Buccal Swabs | −80° C. | StepOnePlus | 0.821 | 0.036 | N/A | Pass |

Week 8 Time Point Conclusion:

All Extracted DNA, Buccal Swabs (other than the Room Temperature and 4° C. Temperature swabs) and reagents yielded reliable results at the various storage conditions for 8 weeks. Therefore, the stability was determined to be 8 weeks at all test temperatures for the DNA extracts with 6 Freeze/Thaw Cycles and at −20° C. and −80° C. for the Buccal Swabs.

Week 10 Time Point

TABLE 22

Week 10 Time Point PCR Results

| Sample Type | Storage Condition | Instruments (7500 Fast or StepOnePlus) | Avg Allele 1 (Range ≥−2SD 0.44) | Avg Allele 2 (Range ≥−2SD 0.027) | Freeze Thaw Cycle | Pass/Fail |
|---|---|---|---|---|---|---|
| Extracted DNA | 4° C. | 7500 Fast | 1.650 | 0.248 | N/A | Pass |
| Extracted DNA | 4° C. | StepOnePlus | 0.958 | 0.079 | N/A | Pass |
| Extracted DNA | −20° C. | 7500 Fast | 1.603 | 0.237 | 7 | Pass |
| Extracted DNA | −20° C. | StepOnePlus | 0.915 | 0.104 | 7 | Pass |
| Extracted DNA | −80° C. | 7500 Fast | 1.650 | 0.248 | 7 | Pass |
| Extracted DNA | −80° C. | StepOnePlus | 0.957 | 0.104 | 7 | Pass |
| Buccal Swabs | −20° C. | 7500 Fast | 1.546 | 0.254 | N/A | Pass |
| Buccal Swabs | −20° C. | StepOnePlus | 0.858 | 0.066 | N/A | Pass |

TABLE 22-continued

Week 10 Time Point PCR Results

| Sample Type | Storage Condition | Instruments (7500 Fast or StepOnePlus) | Avg Allele 1 (Range ≥−2SD 0.44) | Avg Allele 2 (Range ≥−2SD 0.027) | Freeze Thaw Cycle | Pass/Fail |
|---|---|---|---|---|---|---|
| Buccal Swabs | −80° C. | 7500 Fast | 1.447 | 0.233 | N/A | Pass |
| Buccal Swabs | −80° C. | StepOnePlus | 0.880 | 0.067 | N/A | Pass |

Week 10 Time Point Conclusion:

All Extracted DNA, Buccal Swabs (other than the Room Temperature and 4° C. Temperature swabs) and reagents yielded reliable results at the various storage conditions for 10 weeks. Therefore, the stability was determined to be up to 10 weeks at all test temperatures for the DNA extracts with 7 Freeze/Thaw Cycles and at −20° C. and −80° C. for the Buccal Swabs.

Week 12 Time Point

TABLE 23

Week 12 Time Point PCR Results

| Sample Type | Storage Condition | Instruments (7500 Fast or StepOnePlus) | Avg Allele 1 (Range ≥−2SD 0.44) | Avg Allele 2 (Range ≥−2SD 0.027) | Freeze Thaw Cycle | Pass/Fail |
|---|---|---|---|---|---|---|
| Extracted DNA | 4° C. | 7500 Fast | 1.681 | 0.246 | N/A | Pass |
| Extracted DNA | 4° C. | StepOnePlus | 0.981 | 0.089 | N/A | Pass |
| Extracted DNA | −20° C. | 7500 Fast | 1.623 | 0.243 | 8 | Pass |
| Extracted DNA | −20° C. | StepOnePlus | 0.949 | 0.094 | 8 | Pass |
| Extracted DNA | −80° C. | 7500 Fast | 1.724 | 0.246 | 8 | Pass |
| Extracted DNA | −80° C. | StepOnePlus | 1.015 | 0.107 | 8 | Pass |
| Buccal Swabs | −20° C. | 7500 Fast | 1.218 | 0.154 | N/A | Pass |
| Buccal Swabs | −20° C. | StepOnePlus | 0.721 | 0.053 | N/A | Pass |
| Buccal Swabs | −80° C. | 7500 Fast | 1.456 | 0.185 | N/A | Pass |
| Buccal Swabs | −80° C. | StepOnePlus | 0.918 | 0.075 | N/A | Pass |

Week 12 Time Point Conclusion:

All Extracted DNA, Buccal Swabs (other than the Room Temperature and 4° C. Temperature swabs) and reagents yielded reliable results at the various storage conditions for 12 weeks. Therefore, the stability was determined to be up to 12 weeks at all test temperatures for the DNA extracts with 8 Freeze/Thaw Cycles and at −20° C. and −80° C. for the Buccal Swabs.

Conclusions

The mean results for Allele 1 and Allele 2 were calculated at various storage temperatures. The data verified the following stability claim:

TABLE 24

Material and Storage Conditions

| Material and Storage Conditions | Stability | Freeze/Thaw Cycle |
|---|---|---|
| Extracted DNA at 4° C. | 12 weeks | N/A |
| Extracted DNA at −20° C. | 12 weeks | 8 |
| Extracted DNA at −80° C. | 12 weeks | 8 |
| Omega Tissue DNA Kit at Room Temperature | 12 weeks | N/A |
| TaqMan Genotyping Master Mix at 2° C. to 8° C. | 12 weeks | N/A |
| Custom TaqMan SNP Genotyping Assays at −25° C. to −15° C. | 12 weeks | N/A |
| Buccal Swabs at Room Temperature | 1 week | N/A |
| Buccal Swabs at 4° C. Temperature | 3 weeks | N/A |
| Buccal Swabs at −20° C. Temperature | 12 weeks | N/A |
| Buccal Swabs at −80° C. Temperature | 12 weeks | N/A |

Example 7: Stability Study at 6 Months; Controls at 0 Months and 6 Months

The study described in the example was designed to determine the acceptable stabilities of commercial buccal swabs, DNA extracted from buccal swabs, various reagents, and controls used for testing. This example contains a summary of the stability data generated at 6 months, continued from Examples 5 and 6. This report also includes a summary of the control stability data generated at Day 0 through 6 months.

Buccal Swabs

TABLE 25

Storage Conditions and Collection Days

| Storage | Data Collection Days |
|---|---|
| 4° C. Refrigerator | 6 months |
| Room Temperature | 6 months |
| −20° C. Freezer | 6 months |
| −80° C. Freezer | 6 months |

TABLE 26

Extracted DNA Samples in 96-Well Plate

| Storage | Freeze thaw cycles | Data Collection Days |
|---|---|---|
| 4° C. Refrigerator | N/A | 6 months |
| −20° C. Freezer | Cycle 1 to 10 | 6 months |
| −80° C. Freezer | Cycle 1 to 10 | 6 months |

Sequestered reagents were used for the buccal swab and extracted DNA stability test. At the end of this study, the expiration date for use of the listed reagents was established.

Results

Results from 6 months data points are summarized in the following tables.

6 Months Time Point

TABLE 27

Month Time Point Reagent Lot information

| Reagent | Lot # |
|---|---|
| Omega E.Z.N.A. Tissue DNA Kit | D33960205241210CN050312 |
| TaqMan Genotyping Master Mix | 1204073 |
| Custom TaqMan SNP Genotyping Assays | P120814-006 H01 |
| NN Control {purified DNA isolated from buccal swabs of normal individuals used as a process control from Extraction to PCR analysis} | ALU-0912-006 |
| HN Control {purified DNA isolated from whole blood sample of a known Heterozygous individual} | ALU-0912-007 |
| HH Control {DNA cloned, purified and characterized by Bionics Co., Ltd, (ISO0911) in Seoul, Korea} | ALU-0912-008 |

TABLE 28

6 Month Time Point PCR Results

| Sample Type | Storage Condition | Instruments (7500 Fast or StepOnePlus) | Avg Allele 1 (Range ≥−2SD 0.44) | Avg Allele 2 (Range ≥−2SD 0.027) | Freeze Thaw Cycle | Pass/Fail |
|---|---|---|---|---|---|---|
| Extracted DNA | 4° C. | 7500 Fast | N/A | N/A | N/A | N/A |
| Extracted DNA | 4° C. | StepOnePlus | N/A | N/A | N/A | N/A |
| Extracted DNA | −20° C. | 7500 Fast | 1.496 | 0.217 | 9 | Pass |
| Extracted DNA | −20° C. | StepOnePlus | 0.783 | 0.054 | 9 | Fail |
| Extracted DNA | −80° C. | 7500 Fast | 1.642 | 0.245 | 9 | Pass |
| Extracted DNA | −80° C. | StepOnePlus | 0.811 | 0.069 | 9 | Fail |
| Buccal Swabs | −20° C. | 7500 Fast | N/A | N/A | N/A | N/A |
| Buccal Swabs | −20° C. | StepOnePlus | N/A | N/A | N/A | N/A |
| Buccal Swabs | −80° C. | 7500 Fast | 1.654 | 0.274 | N/A | Pass |
| Buccal Swabs | −80° C. | StepOnePlus | 0.881 | 0.067 | N/A | Fail |

6 Month Time Point Conclusion:

All samples ran on the 7500 PCR instrument including Extracted DNA (stored at −20° C. and −80° C.), Buccal Swabs (stored at −80° C.), and reagents yielded reliable results in the various storage conditions for 6 months. Stability for the 7500 PCR instrument was determined to be 6 months for the DNA extracts stored at −20° C. and −80° C. with 9 Freeze/Thaw Cycles and Buccal Swabs stored at −80° C. The stability for the StepOnePlus PCR instrument was still determined to be 12 weeks for all DNA extracts stored at 4° C., −20° C. and −80° C. with 8 Freeze/Thaw Cycles and Buccal Swabs stored at −80° C.

0 and 6 Months Time Points for Controls

Results at Day 0 to 6 months data points are summarized in the following tables and graphs below:

TABLE 29

NN Control - ALU0912-006

| Data Collection Day | DNA Sample Type | Sample Storage Condition | Instruments (7500 Fast or StepOnePlus) | Avg Allele 1 Range: 0.71-1.91 (±2sd) 0.21-2.21 (±3sd) | Avg Allele 2 Range: 0.05-0.27 (±2sd) 0.00-0.34 (±3sd) | Pass/Fail |
|---|---|---|---|---|---|---|
| Day 0 | Extracted | 4° C. | 7500 Fast | 1.94 | 0.33 | Pass |
|  | Extracted | 4° C. | StepOnePlus | 1.11 | 0.13 | Pass |

TABLE 29-continued

NN Control - ALU0912-006

| Data Collection Day | DNA Sample Type | Sample Storage Condition | Instruments (7500 Fast or StepOnePlus) | Avg Allele 1 Range: 0.71-1.91 (±2sd) 0.21-2.21 (±3sd) | Avg Allele 2 Range: 0.05-0.27 (±2sd) 0.00-0.34 (±3sd) | Pass/Fail |
|---|---|---|---|---|---|---|
| | Extracted | −20° C. | 7500 Fast | 1.80 | 0.26 | Pass |
| | Extracted | −20° C. | StepOnePlus | 1.05 | 0.09 | Pass |
| | Extracted | −80° C. | 7500 Fast | 1.88 | 0.28 | Pass |
| | Extracted | −80° C. | StepOnePlus | 1.07 | 0.12 | Pass |
| week 1 | Extracted | 4° C., −20° C., −80° C. | 7500 Fast | 1.60 | 0.23 | Pass |
| | Extracted | 4° C., −20° C., −80° C. | StepOnePlus | 1.03 | 0.10 | Pass |
| week 2 | Extracted | 4° C., −20° C., −80° C. | 7500 Fast | 0.69 | 0.09 | Pass |
| | Extracted DNA | 4° C., −20° C., −80° C. | StepOnePlus | 0.82 | 0.10 | Pass |
| week 3 | Extracted DNA | 4° C., −20° C., −80° C. | 7500 Fast | 1.44 | 0.20 | Pass |
| | Extracted DNA | 4° C., −20° C., −80° C. | StepOnePlus | 0.99 | 0.08 | Pass |
| week 4 | Extracted DNA | 4° C., −20° C., −80° C. | 7500 Fast | 1.32 | 0.17 | Pass |
| | Extracted DNA | 4° C., −20° C., −80° C. | StepOnePlus | 0.91 | 0.10 | Pass |
| week 6 | Extracted DNA | 4° C., −20° C., −80° C. | 7500 Fast | 0.95 | 0.09 | Pass |
| | Extracted DNA | 4° C., −20° C., −80° C. | StepOnePlus | 0.68 | 0.03 | Pass |
| week 8 | Extracted DNA | 4° C., −20° C., −80° C. | 7500 Fast | 1.28 | 0.18 | Pass |
| | Extracted DNA | 4° C., −20° C., −80° C. | StepOnePlus | 0.66 | 0.09 | Pass |
| week 10 | Extracted DNA | 4° C., −20° C., −80° C. | 7500 Fast | 1.20 | 0.16 | Pass |
| | Extracted DNA | 4° C., −20° C., −80° C. | StepOnePlus | 0.81 | 0.07 | Pass |
| week 12 | Extracted DNA | 4° C., −20° C., −80° C. | 7500 Fast | 1.31 | 0.150 | Pass |
| | Extracted DNA | 4° C., −20° C., −80° C. | StepOnePlus | 0.92 | 0.07 | Pass |
| 6 Months | Extracted DNA | 4° C., −20° C., −80° C. | 7500 Fast | 1.46 | 0.21 | Pass |

TABLE 30

HN Control - ALU0912-007

| Data Collection Day | Sample Type | Sample Storage Condition | Instruments (7500 Fast or StepOnePlus) | Avg Allele 1 Range: 0.46-1.25 (±2sd) 0.25-1.45 (±3sd) | Avg Allele 2 Range: 0.32-1.85 (±2sd) 0.00-2.23 (±3sd) | Pass/Fail |
|---|---|---|---|---|---|---|
| Day 0 | Extracted DNA | 4° C. | 7500 Fast | 1.23 | 1.74 | Pass |
| | Extracted DNA | 4° C. | StepOnePlus | 0.85 | 1.23 | Pass |
| | Extracted DNA | −20° C. | 7500 Fast | 1.27 | 1.78 | Pass |
| | Extracted DNA | −20° C. | StepOnePlus | 0.69 | 0.90 | Pass |
| | Extracted DNA | −80° C. | 7500 Fast | 1.26 | 1.77 | Pass |
| | Extracted DNA | −80° C. | StepOnePlus | 0.71 | 0.96 | Pass |
| | Buccal Swabs | RT, 4° C., −20° C., −80° C. | 7500 Fast | 1.32 | 1.96 | Pass |
| | Buccal Swabs | RT, 4° C., −20° C., −80° C. | StepOnePlus | 0.72 | 1.00 | Pass |
| week 1 | Extracted DNA | 4° C., −20° C., −80° C. | 7500 Fast | 0.90 | 1.28 | Pass |
| | Extracted DNA | 4° C., −20° C., −80° C. | StepOnePlus | 0.61 | 0.83 | Pass |
| | Buccal Swabs | RT, 4° C., −20° C., −80° C. | 7500 Fast | 1.00 | 1.43 | Pass |
| | Buccal Swabs | RT, 4° C., −20° C., −80° C. | StepOnePlus | 0.57 | 0.79 | Pass |
| week 2 | Extracted DNA | 4° C., −20° C., −80° C. | 7500 Fast | 0.84 | 1.11 | Pass |
| | Extracted DNA | 4° C., −20° C., −80° C. | StepOnePlus | 0.48 | 0.69 | Pass |
| | Buccal Swabs | RT, 4° C., −20° C., −80° C. | 7500 Fast | 0.97 | 1.35 | Pass |
| | Buccal Swabs | RT, 4° C., −20° C., −80° C. | StepOnePlus | 0.56 | 0.79 | Pass |
| week 3 | Extracted DNA | 4° C., −20° C., −80° C. | 7500 Fast | 0.92 | 1.35 | Pass |
| | Extracted DNA | 4° C., −20° C., −80° C. | StepOnePlus | 0.51 | 0.67 | Pass |
| | Buccal Swabs | 4° C., −20° C., −80° C. | 7500 Fast | 0.95 | 1.36 | Pass |
| | Buccal Swabs | 4° C., −20° C., −80° C. | StepOnePlus | 0.62 | 0.80 | Pass |
| week 4 | Extracted DNA | 4° C., −20° C., −80° C. | 7500 Fast | 0.90 | 1.22 | Pass |
| | Extracted DNA | 4° C., −20° C., −80° C. | StepOnePlus | 0.55 | 0.78 | Pass |
| | Buccal Swabs | 4° C., −20° C., −80° C. | 7500 Fast | 1.05 | 1.46 | Pass |
| | Buccal Swabs | 4° C., −20° C., −80° C. | StepOnePlus | 0.65 | 0.83 | Pass |
| week 6 | Extracted DNA | 4° C., −20° C., −80° C. | 7500 Fast | 0.86 | 1.14 | Pass |
| | Extracted DNA | 4° C., −20° C., −80° C. | StepOnePlus | 0.53 | 0.69 | Pass |
| | Buccal Swabs | −20° C., −80° C. | 7500 Fast | 0.91 | 1.36 | Pass |
| | Buccal Swabs | −20° C., −80° C. | StepOnePlus | 0.52 | 0.70 | Pass |
| week 8 | Extracted DNA | 4° C., −20° C., −80° C. | 7500 Fast | 0.84 | 1.02 | Pass |
| | Extracted DNA | 4° C., −20° C., −80° C. | StepOnePlus | 0.46 | 0.58 | Pass |
| | Buccal Swabs | −20° C., −80° C. | 7500 Fast | 0.93 | 1.22 | Pass |
| | Buccal Swabs | −20° C., −80° C. | StepOnePlus | 0.56 | 0.77 | Pass |
| week 10 | Extracted DNA | 4° C., −20° C., −80° C. | 7500 Fast | 1.02 | 1.38 | Pass |
| | Extracted DNA | 4° C., −20° C., −80° C. | StepOnePlus | 0.53 | 0.71 | Pass |
| | Buccal Swabs | −20° C., −80° C. | 7500 Fast | 0.96 | 1.28 | Pass |
| | Buccal Swabs | −20° C., −80° C. | StepOnePlus | 0.56 | 0.78 | Pass |

TABLE 30-continued

HN Control - ALU0912-007

| Data Collection Day | Sample Type | Sample Storage Condition | Instruments (7500 Fast or StepOnePlus) | Avg Allele 1 Range: 0.46-1.25 (±2sd) 0.25-1.45 (±3sd) | Avg Allele 2 Range: 0.32-1.85 (±2sd) 0.00-2.23 (±3sd) | Pass/Fail |
|---|---|---|---|---|---|---|
| week 12 | Extracted DNA | 4° C., −20° C., −80° C. | 7500 Fast | 0.93 | 1.27 | Pass |
| | Extracted DNA | 4° C., −20° C., −80° C. | StepOnePlus | 0.45 | 0.57 | Pass |
| | Buccal Swabs | −20° C., −80° C. | 7500 Fast | 0.93 | 1.27 | Pass |
| | Buccal Swabs | −20° C., −80° C. | StepOnePlus | 0.45 | 0.57 | Pass |
| 6 months | Extracted DNA | −20° C., −80° C. | 7500 Fast | 0.98 | 1.32 | Pass |
| | Buccal Swabs | −80° C. | 7500 Fast | 0.77 | 0.98 | Pass |

TABLE 31

HH Control- ALU0912-008

| Data Collection Day | Sample Type | Sample Storage Condition | Instruments (7500 Fast or StepOnePlus) | Avg Allele 1 Range: 0.12-0.25 (±2sd) 0.09-0.27 (±3sd) | Avg Allele 2 Range: 0.50-3.12 (±2sd) 0.00-3.79 (±3sd) | Pass/Fail |
|---|---|---|---|---|---|---|
| Day 0 | Extracted DNA | 4° C. | 7500 Fast | 0.23 | 2.61 | Pass |
| | Extracted DNA | 4° C. | StepOnePlus | 0.16 | 1.52 | Pass |
| | Extracted DNA | −20° C. | 7500 Fast | 0.24 | 2.64 | Pass |
| | Extracted DNA | −20° C. | StepOnePlus | 0.14 | 1.33 | Pass |
| | Extracted DNA | −80° C. | 7500 Fast | 0.24 | 2.62 | Pass |
| | Extracted DNA | −80° C. | StepOnePlus | 0.15 | 1.44 | Pass |
| | Buccal Swabs | RT, 4° C., −20° C., −80° C. | 7500 Fast | 0.26 | 2.70 | Pass |
| | Buccal Swabs | RT, 4° C., −20° C., −80° C. | StepOnePlus | 0.13 | 1.45 | Pass |
| week 1 | Extracted DNA | 4° C., −20° C., −80° C. | 7500 Fast | 0.18 | 1.87 | Pass |
| | Extracted DNA | 4° C., −20° C., −80° C. | StepOnePlus | 0.13 | 1.36 | Pass |
| | Buccal Swabs | RT, 4° C., −20° C., −80° C. | 7500 Fast | 0.20 | 2.47 | Pass |
| | Buccal Swabs | RT, 4° C., −20° C., −80° C. | StepOnePlus | 0.13 | 1.33 | Pass |
| week 2 | Extracted DNA | 4° C., −20° C., −80° C. | 7500 Fast | 0.15 | 1.55 | Pass |
| | Extracted DNA | 4° C., −20° C., −80° C. | StepOnePlus | 0.093 | 1.00 | Pass |
| | Buccal Swabs | RT, 4° C., −20° C., −80° C. | 7500 Fast | 0.16 | 1.90 | Pass |
| | Buccal Swabs | RT, 4° C., −20° C., −80° C. | StepOnePlus | 0.12 | 1.22 | Pass |
| week 3 | Extracted DNA | 4° C., −20° C., −80° C. | 7500 Fast | 0.18 | 1.94 | Pass |
| | Extracted DNA | 4° C., −20° C., −80° C. | StepOnePlus | 0.11 | 1.13 | Pass |
| | Buccal Swabs | 4° C., −20° C., −80° C. | 7500 Fast | 0.17 | 2.00 | Pass |
| | Buccal Swabs | 4° C., −20° C., −80° C. | StepOnePlus | 0.13 | 1.21 | Pass |
| week 4 | Extracted DNA | 4° C., −20° C., −80° C. | 7500 Fast | 0.14 | 1.49 | Pass |
| | Extracted DNA | 4° C., −20° C., −80° C. | StepOnePlus | 0.10 | 1.10 | Pass |
| | Buccal Swabs | 4° C., −20° C., −80° C. | 7500 Fast | 0.16 | 1.86 | Pass |
| | Buccal Swabs | 4° C., −20° C., −80° C. | StepOnePlus | 0.111 | 1.08 | Pass |
| week 6 | Extracted DNA | 4° C., −20° C., −80° C. | 7500 Fast | 0.14 | 1.54 | Pass |
| | Extracted DNA | 4° C., −20° C., −80° C. | StepOnePlus | 0.080 | 0.86 | Fail |
| | Buccal Swabs | −20° C., −80° C. | 7500 Fast | 0.16 | 1.84 | Pass |
| | Buccal Swabs | −20° C., −80° C. | StepOnePlus | 0.10 | 0.96 | Pass |
| week 8 | Extracted DNA | 4° C., −20° C., −80° C. | 7500 Fast | 0.14 | 1.41 | Pass |
| | Extracted DNA | 4° C., −20° C., −80° C. | StepOnePlus | 0.13 | 0.84 | Pass |
| | Buccal Swabs | −20° C., −80° C. | 7500 Fast | 0.20 | 2.46 | Pass |
| | Buccal Swabs | −20° C., −80° C. | StepOnePlus | 0.10 | 1.02 | Pass |
| week 10 | Extracted DNA | 4° C., −20° C., −80° C. | 7500 Fast | 0.16 | 1.61 | Pass |
| | Extracted DNA | 4° C., −20° C., −80° C. | StepOnePlus | 0.083 | 0.72 | Fail |
| | Buccal Swabs | −20° C., −80° C. | 7500 Fast | 0.14 | 1.69 | Pass |
| | Buccal Swabs | −20° C., −80° C. | StepOnePlus | 0.11 | 1.04 | Pass |
| week 12 | Extracted DNA | 4° C., −20° C., −80° C. | 7500 Fast | 0.21 | 2.11 | Pass |
| | Extracted DNA | 4° C., −20° C., −80° C. | StepOnePlus | 0.12 | 1.25 | Pass |
| | Buccal Swabs | −20° C., −80° C. | 7500 Fast | 0.21 | 2.11 | Pass |
| | Buccal Swabs | −20° C., −80° C. | StepOnePlus | 0.12 | 1.24 | Pass |
| 6 months | Extracted DNA | −20° C., −80° C. | 7500 Fast | 0.21 | 1.92 | Pass |
| | Buccal Swabs | −80° C. | 7500 Fast | 0.13 | 1.52 | Pass |

TABLE 32

Figure 5:
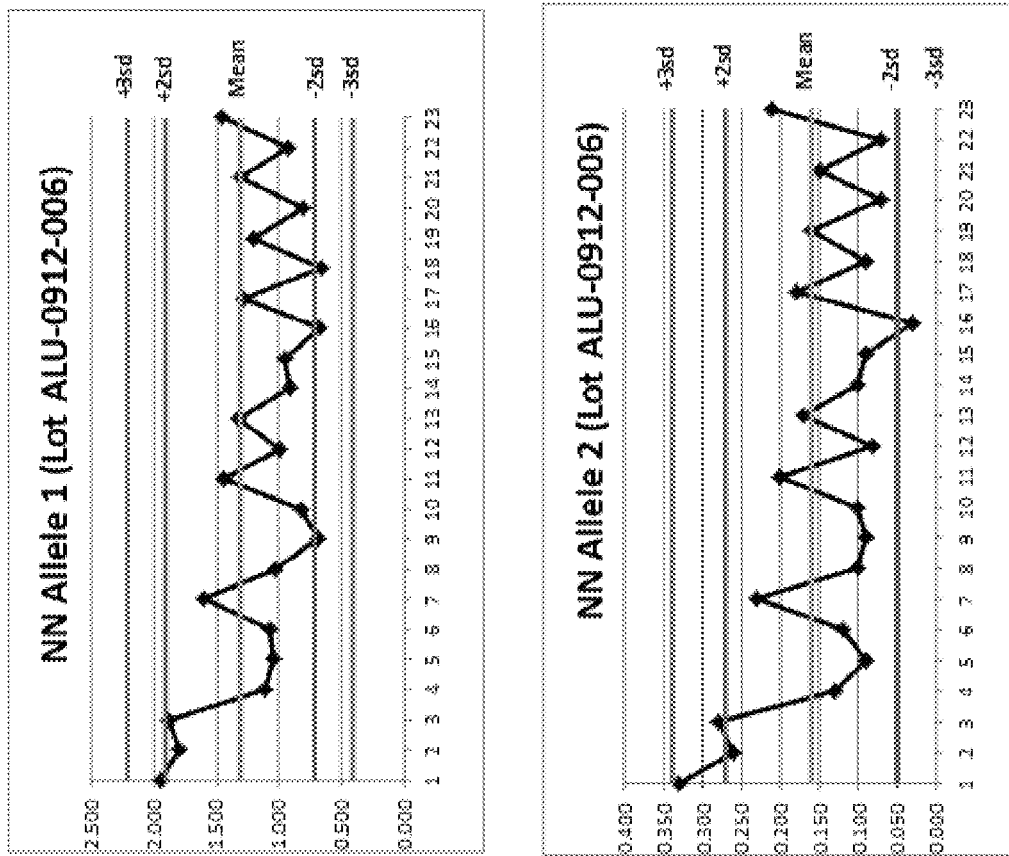
FIG. 5 provides a graph of the control stability results for NN (Lot #ALU012-006) which are shown in Table 32 in Example 7

NN (Lot # ALU012-006) - FIG. 5

NN (ALU-0912-006) — Accepted(A)

| No | Batch Number | Allele 1 (x) | Allele 2 (y) | Instrument | Warning(W) Reject(R) |
|---|---|---|---|---|---|
| 1 | Day 0 | 1.940 | 0.330 | 7500 | W |
| 2 | Day 0 | 1.800 | 0.260 | 7500 | A |
| 3 | Day 0 | 1.880 | 0.280 | 7500 | A |
| 4 | Day 0 | 1.110 | 0.130 | StepOnePlus | A |
| 5 | Day 0 | 1.050 | 0.090 | StepOnePlus | A |
| 6 | Day 0 | 1.070 | 0.120 | StepOnePlus | A |
| 7 | week 1 | 1.600 | 0.230 | 7500 | A |
| 8 | week 1 | 1.030 | 0.100 | StepOnePlus | A |
| 9 | week 2 | 0.690 | 0.090 | 7500 | A |
| 10 | week 2 | 0.820 | 0.100 | StepOnePlus | A |
| 11 | week 3 | 1.440 | 0.200 | 7500 | A |
| 12 | week 3 | 0.990 | 0.080 | StepOnePlus | A |
| 13 | week 4 | 1.320 | 0.170 | 7500 | A |
| 14 | week 4 | 0.910 | 0.100 | StepOnePlus | A |
| 15 | week 6 | 0.950 | 0.090 | 7500 | A |
| 16 | week 6 | 0.680 | 0.030 | StepOnePlus | A |
| 17 | week 8 | 1.280 | 0.180 | 7500 | A |
| 18 | week 8 | 0.660 | 0.090 | StepOnePlus | A |
| 19 | week 10 | 1.200 | 0.160 | 7500 | A |
| 20 | week 10 | 0.810 | 0.070 | StepOnePlus | A |
| 21 | week 12 | 1.310 | 0.150 | 7500 | A |
| 22 | week 12 | 0.920 | 0.070 | StepOnePlus | A |
| 23 | 6 Months | 1.460 | 0.210 | 7500 | A |
| (+)3sd | 2.28 | 0.37 | | | |
| (+)2sd | 1.91 | 0.30 | | | |
| (+)1sd | 1.54 | 0.22 | | | |
| Mean | 1.17 | 0.14 | | | |
| SD | 0.37 | 0.08 | | | |
| (−)1sd | 0.80 | 0.07 | | | |
| (−)2sd | 0.43 | −0.01 | | | |
| (−)3sd | 0.06 | −0.08 | | | |

TABLE 33

Figure 6:
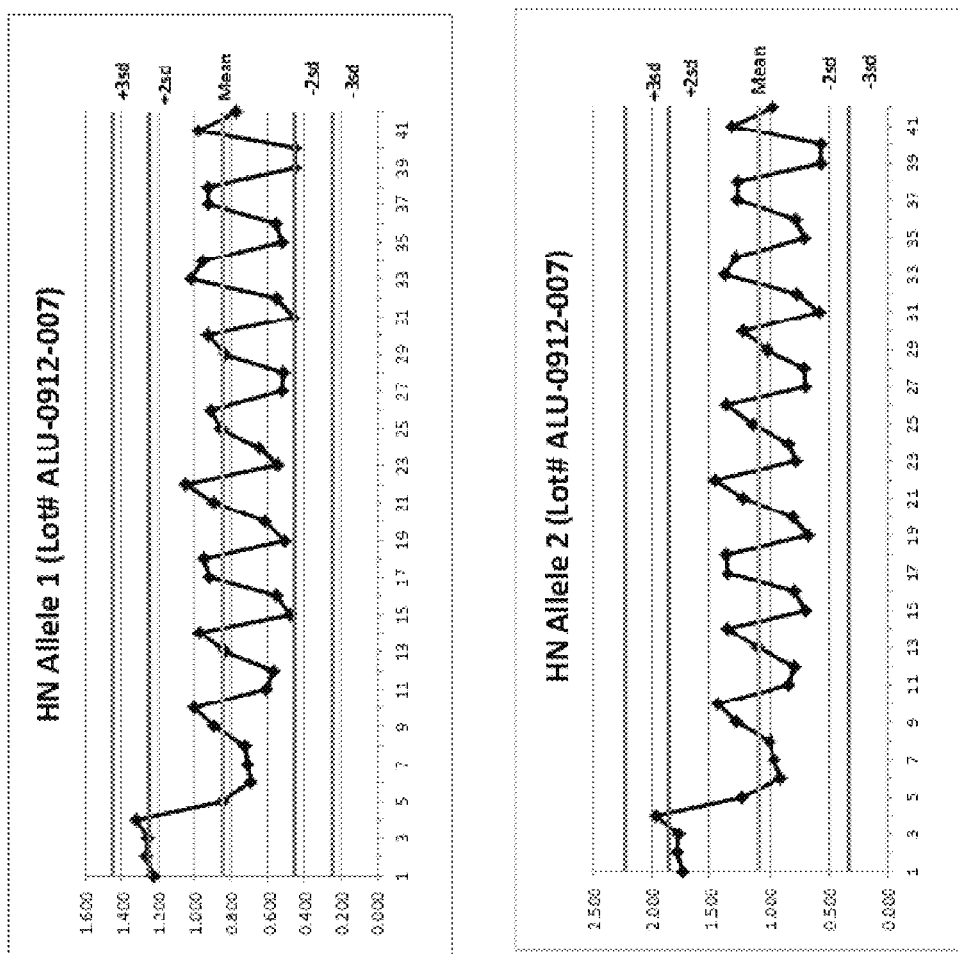
FIG. 6 provides a graph of the control stability results for HN (Lot #ALU912-007) which are shown in Table 33 in Example 7.

HN (Lot # ALU0912-007) - FIG. 6

HN (ALU-0912-007) — Accepted (A)

| No. | Batch Number | Allele 1 (x) | Allele 2 (y) | Instrument | Warning (W) Reject (R) |
|---|---|---|---|---|---|
| 1 | Day 0 | 1.230 | 1.740 | 7500 | A |
| 2 | Day 0 | 1.270 | 1.780 | 7500 | W |
| 3 | Day 0 | 1.260 | 1.770 | 7500 | W |
| 4 | Day 0 | 1.320 | 1.960 | 7500 | W |
| 5 | Day 0 | 0.850 | 1.230 | StepOnePlus | A |
| 6 | Day 0 | 0.690 | 0.900 | StepOnePlus | A |
| 7 | Day 0 | 0.710 | 0.960 | StepOnePlus | A |
| 8 | Day 0 | 0.720 | 1.000 | StepOnePlus | A |
| 9 | week 1 | 0.900 | 1.280 | 7500 | A |
| 10 | week 1 | 1.000 | 1.430 | 7500 | A |
| 11 | week 1 | 0.610 | 0.830 | StepOnePlus | A |
| 12 | week 1 | 0.570 | 0.790 | StepOnePlus | A |
| 13 | week 2 | 0.840 | 1.110 | 7500 | A |
| 14 | week 2 | 0.970 | 1.350 | 7500 | A |
| 15 | week 2 | 0.480 | 0.690 | StepOnePlus | A |
| 16 | week 2 | 0.560 | 0.790 | StepOnePlus | A |
| 17 | week 3 | 0.920 | 1.350 | 7500 | A |
| 18 | week 3 | 0.950 | 1.360 | 7500 | A |
| 19 | week 3 | 0.510 | 0.670 | StepOnePlus | A |
| 20 | week 3 | 0.620 | 0.800 | StepOnePlus | A |
| 21 | week 4 | 0.900 | 1.220 | 7500 | A |
| 22 | week 4 | 1.050 | 1.460 | 7500 | A |
| 23 | week 4 | 0.550 | 0.780 | StepOnePlus | A |
| 24 | week 4 | 0.650 | 0.830 | StepOnePlus | A |
| 25 | week 6 | 0.860 | 1.140 | 7500 | A |
| 26 | week 6 | 0.910 | 1.360 | 7500 | A |
| 27 | week 6 | 0.530 | 0.690 | StepOnePlus | A |
| 28 | week 6 | 0.520 | 0.700 | StepOnePlus | A |
| 29 | week 8 | 0.840 | 1.020 | 7500 | A |
| 30 | week 8 | 0.930 | 1.220 | 7500 | A |
| 31 | week 8 | 0.460 | 0.580 | StepOnePlus | A |
| 32 | week 8 | 0.560 | 0.770 | StepOnePlus | A |
| 33 | week 10 | 1.020 | 1.380 | 7500 | A |
| 34 | week 10 | 0.960 | 1.280 | 7500 | A |
| 35 | week 10 | 0.530 | 0.710 | StepOnePlus | A |
| 36 | week 10 | 0.560 | 0.780 | StepOnePlus | A |
| 37 | week 12 | 0.930 | 1.270 | 7500 | A |
| 38 | week 12 | 0.930 | 1.270 | 7500 | A |
| 39 | week 12 | 0.450 | 0.570 | StepOnePlus | A |
| 40 | week 12 | 0.450 | 0.570 | StepOnePlus | A |
| 41 | 6 Months | 0.980 | 1.320 | 7500 | A |
| 42 | 6 Months | 0.770 | 0.980 | 7500 | A |
| (+)3sd | 1.52 | 2.16 | | | |
| (+)2sd | 1.27 | 1.80 | | | |
| (+)1sd | 1.03 | 1.44 | | | |
| Mean | 0.79 | 1.09 | | | |
| SD | 0.24 | 0.36 | | | |
| (−)1sd | 0.55 | 0.73 | | | |
| (−)2sd | 0.31 | 0.37 | | | |
| (−)3sd | 0.07 | 0.02 | | | |

TABLE 34

Figure 7:
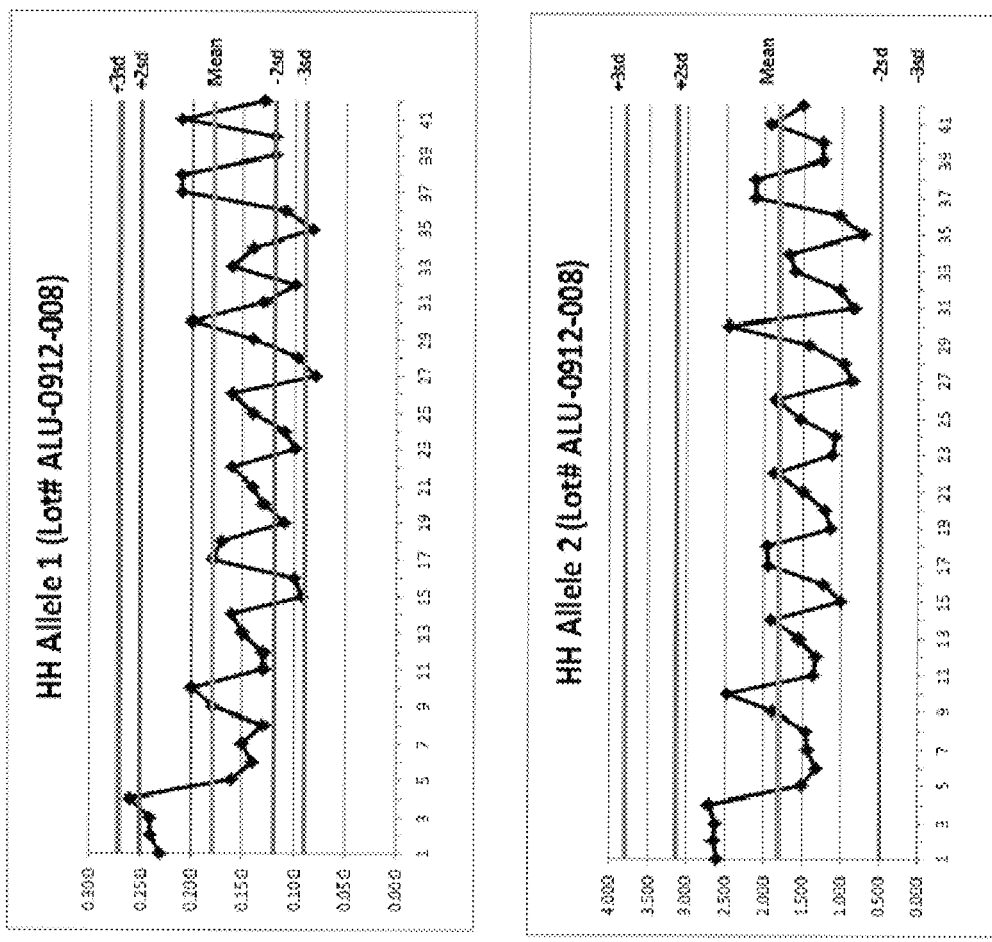
FIG. 7 provides a graph of the control stability results for HH (Lot #ALU912-008) which are shown in Table 34 in Example 7.

HH (Lot # ALU0912-008) - FIG. 7

HH (ALU-0912-008) — Accepted (A)

| No. | Batch Number | Allele 1 (x) | Allele 2 (y) | Instrument | Warning (W) Reject (R) |
|---|---|---|---|---|---|
| 1 | Day 0 | 0.230 | 2.610 | 7500 | A |
| 2 | Day 0 | 0.240 | 2.640 | 7500 | A |
| 3 | Day 0 | 0.240 | 2.620 | 7500 | A |
| 4 | Day 0 | 0.260 | 2.700 | 7500 | W |
| 5 | Day 0 | 0.160 | 1.520 | StepOnePlus | A |
| 6 | Day 0 | 0.140 | 1.330 | StepOnePlus | A |
| 7 | Day 0 | 0.150 | 1.440 | StepOnePlus | A |
| 8 | Day 0 | 0.130 | 1.450 | StepOnePlus | A |
| 9 | week 1 | 0.180 | 1.870 | 7500 | A |
| 10 | week 1 | 0.200 | 2.470 | 7500 | A |
| 11 | week 1 | 0.130 | 1.360 | StepOnePlus | A |
| 12 | week 1 | 0.130 | 1.330 | StepOnePlus | A |
| 13 | week 2 | 0.150 | 1.550 | 7500 | A |
| 14 | week 2 | 0.160 | 1.900 | 7500 | A |
| 15 | week 2 | 0.093 | 1.000 | StepOnePlus | A |
| 16 | week 2 | 0.100 | 1.220 | StepOnePlus | A |
| 17 | week 3 | 0.180 | 1.940 | 7500 | A |
| 18 | week 3 | 0.170 | 1.950 | 7500 | A |
| 19 | week 3 | 0.110 | 1.130 | StepOnePlus | A |
| 20 | week 3 | 0.130 | 1.210 | StepOnePlus | A |
| 21 | week 4 | 0.140 | 1.490 | 7500 | A |
| 22 | week 4 | 0.160 | 1.860 | 7500 | A |
| 23 | week 4 | 0.100 | 1.100 | StepOnePlus | A |
| 24 | week 4 | 0.110 | 1.080 | StepOnePlus | A |
| 25 | week 6 | 0.140 | 1.540 | 7500 | A |
| 26 | week 6 | 0.160 | 1.840 | 7500 | A |
| 27 | week 6 | 0.080 | 0.860 | StepOnePlus | W |
| 28 | week 6 | 0.097 | 0.960 | StepOnePlus | A |
| 29 | week 8 | 0.140 | 1.410 | 7500 | A |
| 30 | week 8 | 0.200 | 2.460 | 7500 | A |
| 31 | week 8 | 0.130 | 0.840 | StepOnePlus | A |
| 32 | week 8 | 0.100 | 1.017 | StepOnePlus | A |
| 33 | week 10 | 0.160 | 1.610 | 7500 | A |
| 34 | week 10 | 0.140 | 1.690 | 7500 | A |
| 35 | week 10 | 0.083 | 0.720 | StepOnePlus | W |
| 36 | week 10 | 0.110 | 1.040 | StepOnePlus | n/a |
| 37 | week 12 | 0.210 | 2.110 | 7500 | n/a |
| 38 | week 12 | 0.210 | 2.110 | 7500 | n/a |
| 39 | week 12 | 0.120 | 1.250 | StepOnePlus | n/a |

TABLE 34-continued

HH (Lot # ALU0912-008) - FIG. 7

| | | HH (ALU-0912-008) | | | Accepted (A) |
|---|---|---|---|---|---|
| No. | Batch Number | Allele 1 (x) | Allele 2 (y) | Instrument | Warning (W) Reject (R) |
| 40 | week 12 | 0.120 | 1.250 | StepOnePlus | n/a |
| 41 | 6 Months | 0.210 | 1.920 | 7500 | n/a |
| 42 | 6 Months | 0.130 | 1.520 | 7500 | n/a |
| (+)3sd | | 0.29 | 3.19 | | |
| (+)2sd | | 0.24 | 2.66 | | |
| (+)1sd | | 0.20 | 2.13 | | |
| Mean | | 0.15 | 1.59 | | |
| SD | | 0.05 | 0.53 | | |
| (−)1sd | | 0.11 | 1.06 | | |
| (−)2sd | | 0.06 | 0.53 | | |
| (−)3sd | | 0.02 | −0.01 | | |

All controls, NN (Lot # ALU-0912-006), HN (Lot # ALU-0912-007), and HH (Lot #ALU-0912-008) had passed all acceptable allele ranges at each time point. Control stability was determined to be 6 months.

Conclusions

The mean results of Allele 1 and Allele 2 were calculated at various storage temperatures. The data verified the following stability claim for each instrument used:

TABLE 35

7500 PCR Instrument

| Material and Storage Conditions | Stability | Freeze/Thaw Cycles |
|---|---|---|
| Extracted DNA at 4° C. | 12 weeks | N/A |
| Extracted DNA at −20° C. | 6 months | 9 |
| Extracted DNA at −80° C. | 6 months | 9 |
| Omega Tissue DNA Kit at Room Temperature | 6 months | N/A |
| TaqMan Genotyping Master Mix at 2° C. to 8° C. | 6 months | N/A |
| Custom TaqMan SNP Genotyping Assays at −25° C. to −15° C. | 6 months | N/A |
| Buccal Swabs at Room Temperature | 1 week | N/A |
| Buccal Swabs at 4° C. Temperature | 3 weeks | N/A |
| Buccal Swabs at −20° C. Temperature | 12 weeks | N/A |
| Buccal Swabs at −80° C. Temperature | 6 months | N/A |

TABLE 36

StepOnePlus PCR Instrument

| Material and Storage Conditions | Stability | Freeze/Thaw Cycles |
|---|---|---|
| Extracted DNA at 4° C. | 12 weeks | N/A |
| Extracted DNA at −20° C. | 12 weeks | 8 |
| Extracted DNA at −80° C. | 12 weeks | 8 |
| Omega Tissue DNA Kit at Room Temperature | 12 weeks | N/A |
| TaqMan Genotyping Master Mix at 2° C. to 8° C. | 12 weeks | N/A |
| Custom TaqMan SNP Genotyping Assays at −25° C. to −15° C. | 12 weeks | N/A |
| Buccal Swabs at Room Temperature | 1 week | N/A |
| Buccal Swabs at 4° C. Temperature | 3 weeks | N/A |
| Buccal Swabs at −20° C. Temperature | 12 weeks | N/A |
| Buccal Swabs at −80° C. Temperature | 12 weeks | N/A |

The data in the following table had verified the following stability claim for each control.

TABLE 37

6 Month Stability for Controls

| Control | Stability | Control Storage Conditions |
|---|---|---|
| NN (Lot # ALU0912-06) | 6 months | −90° C. to −65° C. |
| HN (Lot # ALU0912-07) | 6 months | −90° C. to −65° C. |
| HH (Lot # ALU0912-08) | 6 months | −90° C. to −65° C. |

Example 8: Stability Study at 8 Months

The study described in the example was designed to determine the acceptable stabilities of commercial buccal swabs, DNA extracted from buccal swabs, various reagents, and controls used for testing. This example contains a summary of the stability data generated at 8 months, continued from Examples 5, 6 and 7. This example also includes a summary of the control stability data generated at 8 months.

Buccal Swabs

TABLE 38

Storage Conditions and Collections Days

| Storage | Data Collection Days |
|---|---|
| −20° C. Freezer | 8 months |
| −80° C. Freezer | 8 months |

TABLE 39

Extracted DNA Samples in 96-Well Plate

| Storage | Freeze thaw cycles | Data Collection Days |
|---|---|---|
| −20° C. Freezer | Cycle 1 to until material is used up or failed | 8 months |
| −80° C. Freezer | Cycle 1 to until material is used up or failed | 8 months |

Sequestered reagents were used for the buccal swab and extracted DNA stability test. At the end of this study, the expiration date will be established for the combined use of the listed reagents.

Results

Results from 8 months data points are summarized in the following tables.

8 Months Time Point

TABLE 40

8 Months Time Point PCR Results

| Sample Type | Storage Condition | Instruments (7500 Fast or StepOnePlus) | Avg Allele 1 (Range ≥−2SD 0.44) | Avg Allele 2 (Range ≥−2SD 0.027) | Freeze Thaw Cycle | Pass/Fail |
|---|---|---|---|---|---|---|
| Extracted DNA | 4° C. | 7500 Fast | N/A | N/A | N/A | N/A |
| Extracted DNA | 4° C. | StepOnePlus | N/A | N/A | N/A | N/A |
| Extracted DNA | −20° C. | 7500 Fast | 1.423 | 0.279 | 10 | Pass |
| Extracted DNA | −20° C. | StepOnePlus | N/A | N/A | N/A | N/A |
| Extracted DNA | −80° C. | 7500 Fast | 1.516 | 0.269 | 10 | Pass |
| Extracted DNA | −80° C. | StepOnePlus | N/A | N/A | N/A | N/A |
| Buccal Swabs | −20° C. | 7500 Fast | 1.122 | 0.229 | N/A | N/A |
| Buccal Swabs | −20° C. | StepOnePlus | N/A | N/A | N/A | N/A |
| Buccal Swabs | −80° C. | 7500 Fast | 1.113 | 0.246 | N/A | Pass |
| Buccal Swabs | −80° C. | StepOnePlus | N/A | N/A | N/A | N/A |

8 Months Time Point Conclusion:

All samples ran on the 7500 PCR instrument including Extracted DNA (stored at −20° C. and −80° C.), Buccal Swabs (stored at −20° C. and −80° C.), and reagents yielded reliable results in the various storage conditions for 8 months. Therefore, stability for the 7500 PCR instrument was determined to be 8 months for the DNA extracts stored at −20° C. and −80° C. with 10 Freeze/Thaw Cycles and Buccal Swabs stored at −20° C. and −80° C.

Control Stability

Results at 8 months data points are summarized in the following tables for the 7500 Fast Real-Time PCR System.

All controls, NN (Lot # ALU-0912-006), HN (Lot # ALU-0912-007), and HH (Lot #ALU-0912-008) had passed all acceptable allele ranges at the 8 months time point. Control stability was determined to be 8 months for the 7500 Fast PCR instrument.

Conclusions

The mean results of Allele 1 and Allele 2 were calculated at various storage temperatures. The data verified the following stability claim for each instrument used:

TABLE 41

NN Control - ALU0912-006

| Data Collection Day | Sample Type | Storage Condition | Instruments 7500 Fast | Avg Allele 1 Range: 0.71-1.91 (±2sd) 0.41-2.21 (±3sd) | Avg Allele 2 Range: 0.05-0.27 (±2sd) 0.00-0.34 (±3sd) | Pass/Fail |
|---|---|---|---|---|---|---|
| 8 Months | Extracted DNA | −20° C., −80° C. | 7500 Fast | 1.38 | 0.27 | Pass |

TABLE 42

HN Control - ALU0912-007

| Data Collection Day | Sample Type | Storage Condition | Instruments 7500 Fast | Avg Allele 1 Range: 0.46-1.25 (±2sd) 0.25-1.45 (±3sd) | Avg Allele 2 Range: 0.32-1.85 (±2sd) 0.00-2.23 (±3sd) | Pass/Fail |
|---|---|---|---|---|---|---|
| 8 months | Extracted DNA | −20° C., −80° C. | 7500 Fast | 0.76 | 1.07 | Pass |
| | Buccal Swabs | −20° C., −80° C. | 7500 Fast | 0.74 | 1.11 | Pass |

TABLE 43

HH Control- ALU0912-008

| Data Collection Day | Sample Type | Storage Condition | Instruments 7500 Fast | Avg Allele 1 Range: 0.12-0.25 (±2sd) 0.09-0.27 (±3sd) | Avg Allele 2 Range: 0.50-3.12 (±2sd) 0.00-3.79 (±3sd) | Pass/Fail |
|---|---|---|---|---|---|---|
| 8 months | Extracted DNA | −20° C., −80° C. | 7500 Fast | 0.17 | 1.64 | Pass |
| | Buccal Swabs | −20° C., −80° C. | 7500 Fast | 0.14 | 1.79 | Pass |

TABLE 44

7500 Real-Time PCR System

| Material and Storage Conditions | Stability | Freeze/Thaw Cycles |
|---|---|---|
| Extracted DNA at 4° C. | 12 weeks | N/A |
| Extracted DNA at −20° C. | 8 months | 10 |
| Extracted DNA at −80° C. | 8 months | 10 |
| Omega Tissue DNA Kit at Room Temperature | 8 months | N/A |
| TaqMan Genotyping Master Mix at 2° C. to 8° C. | 8 months | N/A |
| Custom TaqMan SNP Genotyping Assays at −25° C. to −15° C. | 8 months | N/A |
| Buccal Swabs at Room Temperature | 1 week | N/A |
| Buccal Swabs at 4° C. Temperature | 3 weeks | N/A |
| Buccal Swabs at −20° C. Temperature | 8 months | N/A |
| Buccal Swabs at −80° C. Temperature | 8 months | N/A |

TABLE 45

StepOnePlus Real-Time PCR System

| Material and Storage Conditions | Stability | Freeze/Thaw Cycles |
|---|---|---|
| Extracted DNA at 4° C. | 12 weeks | N/A |
| Extracted DNA at −20° C. | 12 weeks | 8 |
| Extracted DNA at −80° C. | 12 weeks | 8 |
| Omega Tissue DNA Kit at Room Temperature | 12 weeks | N/A |
| TaqMan Genotyping Master Mix at 2° C. to 8° C. | 12 weeks | N/A |
| Custom TaqMan SNP Genotyping Assays at −25° C. to −15° C. | 12 weeks | N/A |
| Buccal Swabs at Room Temperature | 1 week | N/A |
| Buccal Swabs at 4° C. Temperature | 3 weeks | N/A |
| Buccal Swabs at −20° C. Temperature | 12 weeks | N/A |
| Buccal Swabs at −80° C. Temperature | 12 weeks | N/A |

The following 7500 instrument data had verified the following stability claim for each control, as shown in Table 46 below.

TABLE 46

Control and Stability Data

| Control | Stability |
|---|---|
| NN (Lot # ALU0912-06) | 8 months for 7500 |
| HN (Lot # ALU0912-07) | 8 months for 7500 |
| HH (Lot # ALU0912-08) | 8 months for 7500 |

Example 9: Stability Study at 10 Months

The study described in the example was designed to determine the acceptable stabilities of commercial buccal swabs, DNA extracted from buccal swabs, various reagents, and controls used for testing. This example contains a summary of the stability data generated at 10 months, continued from Examples 5, 6, 7 and 8. This report also includes a summary of the control stability data generated at 10 months.

Buccal Swabs

TABLE 47

Storage Conditions and Collection Days

| Storage | Data Collection Days |
|---|---|
| −20° C. Freezer | 10 months |
| −80° C. Freezer | 10 months |

TABLE 48

Extracted DNA Samples in 96-Well Plate

| Storage | Freeze thaw cycles | Data Collection Days |
|---|---|---|
| −20° C. Freezer | Cycle 1 to until material is used up or failed | 10 months |
| −80° C. Freezer | Cycle 1 to until material is used up or failed | 10 months |

Reagents

Sequestered reagents were used for the buccal swab and extracted DNA stability test. At the end of this study, the assigned expiration date was established for the combined use of the listed reagents.

Results

Results from 10 months data points are summarized in the following tables.

10 Months Time Point

TABLE 49

10 Months Time Point PCR Results

| Sample Type | Storage Condition | Instruments (7500 Fast) | Avg Allele 1 (Range ≥−2SD 0.44) | Avg Allele 2 (Range ≥−2SD 0.027) | Freeze Thaw Cycle | Pass/Fail |
|---|---|---|---|---|---|---|
| Extracted DNA | 4° C. | 7500 Fast | N/A | N/A | N/A | N/A |
| Extracted DNA | 4° C. | StepOnePlus | N/A | N/A | N/A | N/A |
| Extracted DNA | −20° C. | 7500 Fast | 1.41 | 0.24 | 11 | Pass |
| Extracted DNA | −20° C. | StepOnePlus | N/A | N/A | N/A | N/A |
| Extracted DNA | −80° C. | 7500 Fast | 1.48 | 0.23 | 11 | Pass |
| Extracted DNA | −80° C. | StepOnePlus | N/A | N/A | N/A | N/A |
| Buccal Swabs | −20° C. | 7500 Fast | 0.72 | 0.19 | N/A | Pass |
| Buccal Swabs | −20° C. | StepOnePlus | N/A | N/A | N/A | N/A |
| Buccal Swabs | −80° C. | 7500 Fast | 0.74 | 0.16 | N/A | Pass |
| Buccal Swabs | −80° C. | StepOnePlus | N/A | N/A | N/A | N/A |

10 Months Time Point Conclusion:

All samples ran on the 7500 Fast Real-Time PCR instrument including Extracted DNA (stored at −20° C. and −80° C.), Buccal Swabs (stored at −20° C. and −80° C.), and reagents yielded reliable results in the various storage conditions for 10 months. Therefore, stability for the 7500 Fast Real-Time PCR instrument was determined to be 10 months for the DNA extracts stored at −20° C. and −80° C. with 11 Freeze/Thaw Cycles and Buccal Swabs stored at −20° C. and −80° C.

10 Months Control Stability

Results at 10 months data points are summarized in the following tables for the 7500 Fast Real-Time PCR System.

TABLE 50

NN Control - ALU0912-006

| Data Collection Day | Sample Type | Storage Condition | Instruments 7500 Fast | Avg Allele 1 Range: 0.71-1.91 (±2sd) 0.41-2.21 (±3sd) | Avg Allele 2 Range: 0.05-0.27 (±2sd) 0.00-0.34 (±3sd) | Pass/Fail |
|---|---|---|---|---|---|---|
| 10 Months | Extracted DNA | −20° C., −80° C. | 7500 Fast | 1.51 | 0.24 | Pass |

TABLE 51

HN Control - ALU0912-007

| Data Collection Day | Sample Type | Storage Condition | Instruments 7500 Fast | Avg Allele 1 Range: 0.46-1.25 (±2sd) 0.25-1.45 (±3sd) | Avg Allele 2 Range: 0.32-1.85 (±2sd) 0.00-2.23 (±3sd) | Pass/Fail |
|---|---|---|---|---|---|---|
| 10 months | Extracted DNA | −20° C., −80° C. | 7500 Fast | 0.89 | 1.22 | Pass |
| | Buccal Swabs | −20° C., −80° C. | 7500 Fast | 0.70 | 0.95 | Pass |

TABLE 52

HH Control- ALU0912-008

| Data Collection Day | Sample Type | Storage Condition | Instruments 7500 Fast | Avg Allele 1 Range: 0.12-0.25 (±2sd) 0.09-0.27 (±3sd) | Avg Allele 2 Range: 0.50-3.12 (±2sd) 0.00-3.79 (±3sd) | Pass/Fail |
|---|---|---|---|---|---|---|
| 10 months | Extracted DNA | −20° C., −80° C. | 7500 Fast | 0.17 | 1.63 | Pass |
| | Buccal Swabs | −20° C., −80° C. | 7500 Fast | 0.14 | 1.20 | Pass |

All controls, NN (Lot # ALU-0912-006), HN (Lot # ALU-0912-007), and HH (Lot #ALU-0912-008) had passed all acceptable allele ranges at the 10 month time point. Control stability was determined to be 10 months for the 7500 Fast PCR System.

Conclusions

The mean results of Allele 1 and Allele 2 were calculated at various storage temperatures. The data verified the following stability claim for each instrument used:

TABLE 53

7500 PCR Instrument

| Material and Storage Conditions | Stability | Freeze/Thaw Cycles |
|---|---|---|
| Extracted DNA at 4° C. | 12 weeks | N/A |
| Extracted DNA at −20° C. | 10 months | 11 |
| Extracted DNA at −80° C. | 10 months | 11 |
| Omega Tissue DNA Kit at Room Temperature | 10 months | N/A |
| TaqMan Genotyping Master Mix at 2° C. to 8° C. | 10 months | N/A |

TABLE 53-continued

7500 PCR Instrument

| Material and Storage Conditions | Stability | Freeze/Thaw Cycles |
|---|---|---|
| Custom TaqMan SNP Genotyping Assays at −25° C. to −15° C. | 8 months | N/A |
| Buccal Swabs at Room Temperature | 1 week | N/A |
| Buccal Swabs at 4° C. Temperature | 3 weeks | N/A |
| Buccal Swabs at −20° C. Temperature | 10 months | N/A |
| Buccal Swabs at −80° C. Temperature | 10 months | N/A |

TABLE 54

StepOnePlus PCR Instrument

| Material and Storage Conditions | Stability | Freeze/Thaw Cycles |
|---|---|---|
| Extracted DNA at 4° C. | 12 weeks | N/A |
| Extracted DNA at −20° C. | 12 weeks | 8 |
| Extracted DNA at −80° C. | 12 weeks | 8 |
| Omega Tissue DNA Kit at Room Temperature | 12 weeks | N/A |
| TaqMan Genotyping Master Mix at 2° C. to 8° C. | 12 weeks | N/A |
| Custom TaqMan SNP Genotyping Assays at −25° C. to −15° C. | 12 weeks | N/A |
| Buccal Swabs at Room Temperature | 1 week | N/A |
| Buccal Swabs at 4° C. Temperature | 3 weeks | N/A |
| Buccal Swabs at −20° C. Temperature | 12 weeks | N/A |
| Buccal Swabs at −80° C. Temperature | 12 weeks | N/A |

The following 7500 Fast Real-Time instrument data had verified the following stability claim for each control:

TABLE 55

Control and Stability Time

| Control | Stability |
|---|---|
| NN (Lot # ALU0912-06) | 10 months for 7500 |
| HN (Lot # ALU0912-07) | 10 months for 7500 |
| HH (Lot # ALU0912-08) | 10 months for 7500 |

Example 10: Stability Study at 12 Months

The study described in the example was designed to determine the acceptable stabilities of commercial buccal swabs, DNA extracted from buccal swabs, various reagents, and controls used for testing. This example contains a summary of the stability data generated at 12 months, continued from Examples 5, 6, 7, 8 and 9. This report also includes a summary of the control stability data generated at 10 months.

Results from 12 months data points are summarized in the following tables.

12 Months Time Point

TABLE 56

12 Months Time Point PCR Results

| Sample Type | Storage Condition | Instruments (7500 Fast) | Avg Allele 1 (Range ≥−2SD 0.44) | Avg Allele 2 (Range ≥−2SD 0.027) | Freeze Thaw Cycle | Pass/Fail |
|---|---|---|---|---|---|---|
| Extracted DNA | 4° C. | 7500 Fast | N/A | N/A | N/A | N/A |
| Extracted DNA | 4° C. | StepOnePlus | N/A | N/A | N/A | N/A |
| Extracted DNA | −20° C. | 7500 Fast | 1.37 | 0.21 | 12 | Pass |
| Extracted DNA | −20° C. | StepOnePlus | N/A | N/A | N/A | N/A |
| Extracted DNA | −80° C. | 7500 Fast | 1.40 | 0.19 | 12 | Pass |
| Extracted DNA | −80° C. | StepOnePlus | N/A | N/A | N/A | N/A |
| Buccal Swabs | −20° C. | 7500 Fast | 0.64 | 0.12 | 3 | Pass |
| Buccal Swabs | −20° C. | StepOnePlus | N/A | N/A | N/A | N/A |
| Buccal Swabs | −80° C. | 7500 Fast | 0.94 | 0.23 | 3 | Pass |
| Buccal Swabs | −80° C. | StepOnePlus | N/A | N/A | N/A | N/A |

12 Months Time Point Conclusion:

All samples ran on the 7500 Fast Real-Time PCR instrument including Extracted DNA (stored at −20° C. and −80° C.), Buccal Swabs (stored at −20° C. and −80° C.), and reagents yielded reliable results in the various storage conditions for 12 months. Therefore, stability for the 7500 Fast Real-Time PCR instrument was determined to be 12 months for the DNA extracts stored at −20° C. and −80° C. with 12 Freeze/Thaw Cycles and Buccal Swabs stored at −20° C. and −80° C. with 3 Freeze/Thaw Cycles.

12 Months Control Stability

Results at 12 months data points are summarized in the following tables for the 7500 Fast Real-Time PCR System.

TABLE 57

NN Control - ALU0912-006

| Data Collection Day | Sample Type | Storage Condition | Instruments | Avg Allele 1 Range: 0.71-1.91 (±2sd) 0.41-2.21 (±3sd) | Avg Allele 2 Range: 0.05-0.27 (±2sd) 0.00-0.34 (±3sd) | Pass/Fail |
|---|---|---|---|---|---|---|
| 12 Months | Extracted DNA | −20° C., −80° C. | 7500 Fast | 1.12 | 021 | Pass |

TABLE 58

HN Control - ALU0912-007

| Data Collection Day | Sample Type | Storage Condition | Instruments 7500 Fast | Avg Allele 1 Range: 0.46-1.25 (±2sd) 0.25-1.45 (±3sd) | Avg Allele 2 Range: 0.32-1.85 (±2sd) 0.00-2.23 (±3sd) | Pass/Fail |
|---|---|---|---|---|---|---|
| 12 months | Extracted DNA | −20° C., −80° C. | 7500 Fast | 0.66 | 0.90 | Pass |
|  | Buccal Swabs | −20° C., −80° C. | 7500 Fast | 0.70 | 1.03 | Pass |

TABLE 59

HH Control- ALU0912-008

| Data Collection Day | Sample Type | Storage Condition | Instruments 7500 Fast | Avg Allele 1 Range: 0.12-0.25 (±2sd) 0.09-0.27 (±3sd) | Avg Allele 2 Range: 0.50-3.12 (±2sd) 0.00-3.79 (±3sd) | Pass/Fail |
|---|---|---|---|---|---|---|
| 12 months | Extracted DNA | −20° C., −80° C. | 7500 Fast | 0.10 | 0.95 | Pass |
|  | Buccal Swabs | −20° C., −80° C. | 7500 Fast | 0.08 | 1.24 | Pass |

All controls, NN (Lot # ALU-0912-006), FIN (Lot # ALU-0912-007), and HH (Lot #ALU-0912-008) had passed all acceptable allele ranges at the 12 month time point. Control stability was determined to be 10 months for the 7500 Fast PCR System.

Conclusions

The mean results of Allele 1 and Allele 2 were calculated at various storage temperatures. The data verified the following stabilities.

TABLE 60

7500 PCR Instrument

| Material and Storage Conditions | Stability | Freeze/Thaw Cycles |
|---|---|---|
| Extracted DNA at 4° C. | 12 weeks | N/A |
| Extracted DNA at −20° C. | 12 months | 12 |
| Extracted DNA at −80° C. | 12 months | 12 |
| Omega Tissue DNA Kit at Room Temperature | 12 months | N/A |
| TaqMan Genotyping Master Mix at 2° C. to 8° C. | 12 months | N/A |
| Custom TaqMan SNP Genotyping Assays at −25° C. to −15° C. | 12 months | N/A |
| Buccal Swabs at Room Temperature | 1 week | N/A |
| Buccal Swabs at 4° C. Temperature | 3 weeks | N/A |
| Buccal Swabs at −20° C. Temperature | 12 months | N/A |
| Buccal Swabs at −80° C. Temperature | 12 months | N/A |

TABLE 61

StepOnePlus PCR Instrument

| Material and Storage Conditions | Stability | Freeze/Thaw Cycles |
|---|---|---|
| Extracted DNA at 4° C. | 12 weeks | N/A |
| Extracted DNA at −20° C. | 12 weeks | 8 |
| Extracted DNA at −80° C. | 12 weeks | 8 |
| Omega Tissue DNA Kit at Room Temperature | 12 weeks | N/A |
| TaqMan Genotyping Master Mix at 2° C. to 8° C. | 12 weeks | N/A |
| Custom TaqMan SNP Genotyping Assays at −25° C. to −15° C. | 12 weeks | N/A |
| Buccal Swabs at Room Temperature | 1 week | N/A |
| Buccal Swabs at 4° C. Temperature | 3 weeks | N/A |
| Buccal Swabs at −20° C. Temperature | 12 weeks | N/A |
| Buccal Swabs at −80° C. Temperature | 12 weeks | N/A |

The following 7500 Fast Real-Time instrument data had verified the following stability claim for each control:

TABLE 62

Control and Stability Time

| Control | Stability |
|---|---|
| NN (Lot # ALU0912-06) | 12 months for 7500 |
| HN (Lot # ALU0912-07) | 12 months for 7500 |
| HH (Lot # ALU0912-08) | 12 months for 7500 |

REFERENCES

All headings and section designations are used for clarity and reference purposes only and are not to be considered limiting in any way. For example, those of skill in the art will appreciate the usefulness of combining various aspects from different headings as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed:

1. A method for preparing genomic DNA (gDNA) samples, the method comprising:
   (A) providing a sample of buccal epithelial cells from a subject, the buccal epithelial cells adhered to at least a part of a substrate;
   (B) agitating, for no more than 45 seconds, said at least a part of the substrate with the adhered epithelial cells in a first lysis solution capable of lysing buccal cells adhered to the substrate;
   (C) removing the substrate from the first lysis solution upon completion of the agitating (B) said at least a part of the substrate in the first lysis solution;
   (D) performing an extraction incubation of gDNA in the first lysis solution by incubating the first lysis solution at a temperature of 45±3° C. for 45±15 minutes after removing (C) the substrate from the first lysis solution to prepare a first gDNA sample;
   (E) agitating said at least a part of the substrate, after removing (C) the substrate from the first lysis solution, in a second lysis solution capable of lysing buccal cells adhered to the substrate;
   (F) removing the substrate from the second lysis solution; and
   (G) performing an extraction incubation of second gDNA in the second lysis solution by incubating the second lysis solution at a temperature of 45±3° C. for 45±15 minutes after removing (F) the substrate from the second lysis solution to prepare a second gDNA sample.

2. The method of claim 1, further comprising:
   after removing (C) the substrate from the first lysis solution,
   (H) freezing the substrate; and,
   prior to agitating (E) the substrate,
   (I) thawing the substrate.

3. The method of claim 1, further comprising:
   (J) isolating genomic DNA from the first lysis solution, the second lysis solution, or both the first lysis solution and the second lysis solution, after the respective incubating (D), (G), or (D) and (G) at a temperature of 45±3° C. for 45±15 minutes, in a respective first gDNA solution, a second gDNA solution, or a first gDNA solution and a second gDNA solution.

4. The method of claim 3, wherein the first gDNA solution, the second gDNA solution, or the first gDNA solution and the second gDNA solution each have a respective volume of between 10 μL and 200 μL.

5. The method of claim 3, further comprising:
   (K) detecting the presence of an allele in the subject's DNA by real-time PCR analysis of a sample of the first gDNA solution, a sample of the second gDNA solution, or a sample of the first gDNA solution and a sample of the second gDNA solution.

6. The method according to claim 5, wherein the sample of the first gDNA solution, the sample of the second gDNA solution, or the sample of the first gDNA solution and the sample of the second gDNA solution used for the real-time PCR analysis each have a respective volume of no more than 2 μL.

7. The method of claim 5, wherein the real-time PCR analysis includes performing 40 cycles of a method including steps:
   (1) denaturing double-stranded nucleic acids;
   (2) annealing a forward primer, a reverse primer, and a detection probe to genomic DNA from the respective gDNA solution; and
   (3) synthesizing second-strand DNA from the annealed forward primer and the annealed reverse primer.

8. The method of claim 7, wherein denaturing (1) double-stranded nucleic acids includes incubation at 95° C. for 3 seconds.

9. The method of claim 1, wherein the temperature of the lysis solution remains between 15° C. and 30° C. during the agitating (E) said at least a part of the substrate.

10. The method of claim 1, wherein the temperature of the lysis solution remains between 18° C. and 25° C. during the agitating (E) said at least a part of the substrate.

11. The method of claim 1, wherein said at least a part of the substrate is agitated (E) in the second lysis solution for no more than 45 seconds.

12. The method of claim 1, wherein the second lysis solution has a volume of between 100 μL and 200 μL.

13. The method according to claim 1, wherein the temperature of the lysis solution is maintained at between 15° C. and 30° C. during the agitating (B) said at least a part of the substrate.

14. The method according to claim 1, wherein the temperature of the lysis solution is maintained at between 18° C. and 25° C. during the agitating (B) said at least a part of the substrate.

15. The method according to claim 1, wherein said at least a part of the substrate is agitated (B) in the first lysis solution for no more than 30 seconds.

16. The method of claim 1, wherein the first lysis solution has a volume of between 100 μL and 200 μL.

17. The method according to claim 1, comprising:
(L) determining an identity of a nucleotide present in the TGFβI gene, the nucleotide located at a position of the TGFβI gene corresponding to a C(G/A)C single nucleotide polymorphism (SNP) associated with Avellino corneal dystrophy.

18. The method according to claim 17, wherein the determining comprises amplifying the nucleotide using a forward PCR primer having a nucleotide sequence consisting of SEQ ID NO:1 and a reverse PCR primer having a nucleotide sequence consisting of SEQ ID NO:2.

19. The method according to claim 17, wherein the determining comprises detecting the nucleotide using a wild type detection probe having a nucleotide sequence consisting of SEQ ID NO:25 and a mutant detection probe having a nucleotide sequence consisting of SEQ ID NO:26.

20. The method according to claim 17, wherein the buccal epithelial cells are adhered to a tip of the substrate.

21. A method for preparing genomic DNA (gDNA) samples for detection of a single nucleotide polymorphism, the method comprising:
(A) providing a sample of buccal epithelial cells from a subject, the buccal epithelial cells adhered to a tip of a substrate;
(B) agitating, for no more than 45 seconds, the tip of the substrate with the adhered epithelial cells in a first lysis solution capable of lysing buccal cells adhered to the substrate;
(C) removing the substrate from the first lysis solution upon completion of the agitating (B) the tip of the substrate in the first lysis solution;
(D) performing an extraction incubation of gDNA in the first lysis solution by incubating the first lysis solution at a temperature of 45±3° C. for 45±15 minutes after removing (C) the substrate from the first lysis solution to prepare a first gDNA sample;
(E) agitating the tip of the substrate, after removing (C) the substrate from the first lysis solution, in a second lysis solution capable of lysing buccal cells adhered to the substrate;
(F) removing the substrate from the second lysis solution; and
(G) performing an extraction incubation of second gDNA in the second lysis solution by incubating the second lysis solution at a temperature of 45±3° C. for 45±15 minutes after removing (F) the substrate from the second lysis solution to prepare a second gDNA sample.

\* \* \* \* \*

SEQUENCE LISTING

<160> NUMBER OF SEQ ID NOS: 42

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tccaccacca ctcagctgta                                                      20

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
ccatctcagg cctcagctt                                                       19

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
tgcagcccta ccactctcaa                                                      20

<210> SEQ ID NO 4
<211> LENGTH: 16
<212> TYPE: DNA
<213> ORGANISM: Artificial Sequence
<220> FEATURE:
<223> OTHER INFORMATION: primer

<400> SEQUENCE: 4
aggcctcgtt gctagg                                                          16

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tagtctctta ttctaataga                                                      20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
gctgcagact ctgtgtttaa                                                      20

<210> SEQ ID NO 7
<211> LENGTH: 22
<212> TYPE: DNA
<213> ORGANISM: Artificial Sequence -continued

```
<220> FEATURE:
<223> OTHER INFORMATION: primer

<400> SEQUENCE: 7
ccatccctcc ttctgtcttc tg                                              22

<210> SEQ ID NO 8
<211> LENGTH: 16
<212> TYPE: DNA
<213> ORGANISM: Artificial Sequence
<220> FEATURE:
<223> OTHER INFORMATION: primer

<400> SEQUENCE: 8
cgggcccctc catctc                                                     16

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
cagagaaggg agggtgtggt t                                               21

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
gggcgaagat ggtgaagct                                                  19

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
tcctcgtcct ctccacctgt a                                               21

<210> SEQ ID NO 12
<211> LENGTH: 17
<212> TYPE: DNA
<213> ORGANISM: Artificial Sequence
<220> FEATURE:
<223> OTHER INFORMATION: primer

<400> SEQUENCE: 12
agctggcaag gaggccc                                                    17

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
tttgggcttt cccacatgc                                                  19
```

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ggcagacgga ggtcatctca                                                    20

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
gtagtaccgt gctctctg                                                      18

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
agttccccat aagaatcccc c                                                  21

<210> SEQ ID NO 17
<211> LENGTH: 17
<212> TYPE: DNA
<213> ORGANISM: Artificial Sequence
<220> FEATURE:
<223> OTHER INFORMATION: primer

<400> SEQUENCE: 17
ggctggaccc ccagagg                                                       17

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
acccctcggg gaagtaagg                                                     19

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
aacctttacg agaccctggg a                                                  21

<210> SEQ ID NO 20
<211> LENGTH: 20
<212> TYPE: DNA
<213> ORGANISM: Artificial Sequence
<220> FEATURE:
<223> OTHER INFORMATION: primer

```
<400> SEQUENCE: 20
gactcccatc catcatgccc                                                   20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
agtcgttgga tccaccacca                                                   20

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
gacgtcattt cctactgttt cagg                                              24

<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23 cccccagaa acagcctg                                                      18

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
ttctaagggg ttaaggagaa agctt                                             25

<210> SEQ ID NO 25
<211> LENGTH: 15
<212> TYPE: DNA
<213> ORGANISM: Artificial Sequence
<220> FEATURE:
<223> OTHER INFORMATION: probe

<400> SEQUENCE: 25
cacggaccgc acgga                                                        15

<210> SEQ ID NO 26
<211> LENGTH: 15
<212> TYPE: DNA
<213> ORGANISM: Artificial Sequence
<220> FEATURE:
<223> OTHER INFORMATION: probe

<400> SEQUENCE: 26
cacggaccac acgga                                                        15

<210> SEQ ID NO 27
```

```
<211> LENGTH: 14
<212> TYPE: DNA
<213> ORGANISM: Artificial Sequence
<220> FEATURE:
<223> OTHER INFORMATION: probe

<400> SEQUENCE: 27
acacggaccg cacg                                                      14

<210> SEQ ID NO 28
<211> LENGTH: 14
<212> TYPE: DNA
<213> ORGANISM: Artificial Sequence
<220> FEATURE:
<223> OTHER INFORMATION: probe

<400> SEQUENCE: 28
acacggacca cacg                                                      14

<210> SEQ ID NO 29
<211> LENGTH: 13
<212> TYPE: DNA
<213> ORGANISM: Artificial Sequence
<220> FEATURE:
<223> OTHER INFORMATION: probe

<400> SEQUENCE: 29
tacacggacc gca                                                       13

<210> SEQ ID NO 30
<211> LENGTH: 13
<212> TYPE: DNA
<213> ORGANISM: Artificial Sequence
<220> FEATURE:
<223> OTHER INFORMATION: probe

<400> SEQUENCE: 30
tacacggacc aca                                                       13

<210> SEQ ID NO 31
<211> LENGTH: 18
<212> TYPE: DNA
<213> ORGANISM: Artificial Sequence
<220> FEATURE:
<223> OTHER INFORMATION: probe

<400> SEQUENCE: 31
ctgtacacgg accgcacg                                                  18

<210> SEQ ID NO 32
<211> LENGTH: 18
<212> TYPE: DNA
<213> ORGANISM: Artificial Sequence
<220> FEATURE:
<223> OTHER INFORMATION: probe

<400> SEQUENCE: 32
ctgtacacgg accacacg                                                  18

<210> SEQ ID NO 33
<211> LENGTH: 21
<212> TYPE: DNA
<213> ORGANISM: Artificial Sequence
<220> FEATURE:
<223> OTHER INFORMATION: probe

<400> SEQUENCE: 33
```
ctgtacacgg accgcacgga g                                           21

<210> SEQ ID NO 34
<211> LENGTH: 21
<212> TYPE: DNA
<213> ORGANISM: Artificial Sequence
<220> FEATURE:
<223> OTHER INFORMATION: probe

<400> SEQUENCE: 34
ctgtacacgg accacacgga g                                           21

<210> SEQ ID NO 35
<211> LENGTH: 24
<212> TYPE: DNA
<213> ORGANISM: Artificial Sequence
<220> FEATURE:
<223> OTHER INFORMATION: probe

<400> SEQUENCE: 35
gctgtacacg gaccgcacgg agaa                                        24

<210> SEQ ID NO 36
<211> LENGTH: 24
<212> TYPE: DNA
<213> ORGANISM: Artificial Sequence
<220> FEATURE:
<223> OTHER INFORMATION: probe

<400> SEQUENCE: 36
gctgtacacg gaccacacgg agaa                                        24

<210> SEQ ID NO 37
<211> LENGTH: 15
<212> TYPE: DNA
<213> ORGANISM: Artificial Sequence
<220> FEATURE:
<223> OTHER INFORMATION: probe

<400> SEQUENCE: 37
accgcacgga gaagc                                                  15

<210> SEQ ID NO 38
<211> LENGTH: 15
<212> TYPE: DNA
<213> ORGANISM: Artificial Sequence
<220> FEATURE:
<223> OTHER INFORMATION: probe

<400> SEQUENCE: 38
accacacgga gaagc                                                  15

<210> SEQ ID NO 39
<211> LENGTH: 21
<212> TYPE: DNA
<213> ORGANISM: Artificial Sequence
<220> FEATURE:
<223> OTHER INFORMATION: probe

<400> SEQUENCE: 39
accgcacgga gaagctgagg c                                           21

<210> SEQ ID NO 40
<211> LENGTH: 21
<212> TYPE: DNA

```
<213> ORGANISM: Artificial Sequence
<220> FEATURE:
<223> OTHER INFORMATION: probe

<400> SEQUENCE: 40
accacacgga gaagctgagg c                                              21

<210> SEQ ID NO 41
<211> LENGTH: 24
<212> TYPE: DNA
<213> ORGANISM: Artificial Sequence
<220> FEATURE:
<223> OTHER INFORMATION: probe

<400> SEQUENCE: 41
accgcacgga gaagctgagg cctg                                           24

<210> SEQ ID NO 42
<211> LENGTH: 24
<212> TYPE: DNA
<213> ORGANISM: Artificial Sequence
<220> FEATURE:
<223> OTHER INFORMATION: probe

<400> SEQUENCE: 42
accacacgga gaagctgagg cctg                                           24
```